US012569447B2

(12) United States Patent
Bradbury et al.

(10) Patent No.: US 12,569,447 B2
(45) Date of Patent: Mar. 10, 2026

(54) SYSTEM AND METHOD FOR ADDITIVE MANUFACTURING USING AN OMNIDIRECTIONAL MAGNETIC MOVEMENT APPARATUS

(71) Applicant: APRECIA PHARMACEUTICALS LLC, Blue Ash, OH (US)

(72) Inventors: Thomas J. Bradbury, Yardley, PA (US); Scott N. Danhof, Columbus, OH (US); Jared T. Emerson, Columbus, OH (US); Thomas D. Haubert, Columbus, OH (US); Jeffrey R. Held, Columbus, OH (US); Steven Van Cleve Korol, Dundee, OR (US); Grace M. Lillie, Columbus, OH (US); James A. Prescott, Columbus, OH (US); Jake M. Pyzza, Columbus, OH (US); Steven M. Risser, Columbus, OH (US); Kenneth B. Scott, Columbus, OH (US); Frederick A. Sexton, Stuart, FL (US); Kyle Edward Smith, Blue Ash, OH (US); John P. Tallarico, Columbus, OH (US); Jaedeok Yoo, Princeton, NJ (US); Kevin L. Yugulis, Columbus, OH (US)

(73) Assignee: APRECIA PHARMACEUTICALS LLC, Mason, OH (US)

( * ) Notice: Subject to any disclaimer, the term of this patent is extended or adjusted under 35 U.S.C. 154(b) by 0 days.

(21) Appl. No.: 18/647,296

(22) Filed: Apr. 26, 2024

(65) Prior Publication Data

US 2024/0269080 A1 Aug. 15, 2024

Related U.S. Application Data

(63) Continuation of application No. 18/704,601, filed as application No. PCT/US2023/018495 on Apr. 13, 2023, now abandoned.

(Continued)

(51) Int. Cl.
*A61K 9/20* (2006.01)
*B29C 64/227* (2017.01)
(Continued)

(52) U.S. Cl.
CPC ............ *A61K 9/2095* (2013.01); *B33Y 30/00* (2014.12); *B33Y 40/20* (2020.01); *B33Y 50/02* (2014.12);
(Continued)

(58) Field of Classification Search
CPC ... B29C 64/227; B29C 64/245; B29C 64/165; B29C 64/264; B29C 64/30;
(Continued)

(56) References Cited

U.S. PATENT DOCUMENTS 4,825,227 A    4/1989  Fischbeck et al.
4,875,619 A    10/1989 Anderson et al.
(Continued)

FOREIGN PATENT DOCUMENTS

CA        3083701 A1    12/2020
KR    20110045955 A  *  5/2011  ....... H01L 21/67784
(Continued)

OTHER PUBLICATIONS

KR-20110045955-A Espacenet Machine Translation (Year: 2024).*
(Continued)

*Primary Examiner* — Seyed Masoud Malekzadeh
(74) *Attorney, Agent, or Firm* — Daniel F. Nesbitt; Nesbitt IP LLC

(57) ABSTRACT

A process system and method for the making of articles, using an omnidirectional magnetic movement system with a transport surface and fabrication modules having a formation surface that can be transported omnidirectionally over the transport surface under the control of a movement controller. An article forming system provides process unit (Continued)

operations for forming articles onto the formation surface as the fabrication modules are moved asynchronously between a plurality of processing positions on the transport surface, and features a depositing device for placing a construction material onto the formation surface and one or more processing devices to form the construction material into the article.

27 Claims, 16 Drawing Sheets

Related U.S. Application Data

(60) Provisional application No. 63/455,281, filed on Mar. 29, 2023, provisional application No. 63/416,585, filed on Oct. 16, 2022, provisional application No. 63/330,667, filed on Apr. 13, 2022.

(51) Int. Cl.

| | |
|---|---|
| B29C 64/245 | (2017.01) |
| B33Y 30/00 | (2015.01) |
| B33Y 40/20 | (2020.01) |
| B33Y 50/02 | (2015.01) |
| B65G 54/02 | (2006.01) |

(52) U.S. Cl.
CPC .......... *B29C 64/227* (2017.08); *B29C 64/245* (2017.08); *B65G 54/02* (2013.01)

(58) Field of Classification Search
CPC ..... B29C 64/112; B29C 64/35; A61K 9/2095; B65G 54/02; B65G 35/06; B33Y 30/00; B33Y 40/00; B33Y 70/00; B33Y 80/00; B33Y 40/20; B33Y 10/00; B33Y 50/02; B23K 26/08; B23K 26/144; B23K 26/342; A61J 3/10; H01L 21/67709; H01L 21/67742; H01L 21/02288; H01L 21/288; H01L 21/6715; H01L 21/70; H01L 27/00; H01L 21/00; H01L 21/67173; H01L 21/67178; H01L 21/67184; H01L 21/67196; H01L 21/67703; H02N 15/00; B22F 10/25; B22F 10/00; B22F 10/14; B22F 2999/00; B28B 1/001; B29L 2031/34; B41J 2/16517
See application file for complete search history.

(56) References Cited

U.S. PATENT DOCUMENTS

| | | | |
|---|---|---|---|
| 4,883,219 A | 11/1989 | Anderson et al. | |
| 4,937,598 A | 6/1990 | Hine et al. | |
| 5,387,380 A | 2/1995 | Cima et al. | |
| 5,659,346 A | 8/1997 | Moynihan et al. | |
| 5,757,391 A | 5/1998 | Hoisington | |
| 5,781,212 A | 7/1998 | Burr et al. | |
| 5,977,780 A | 11/1999 | Herrmann | |
| 6,069,418 A | 5/2000 | Tanaka | |
| 6,070,107 A | 5/2000 | Lombardi et al. | |
| 6,097,114 A | 8/2000 | Hazelton | |
| 6,258,381 B1 | 7/2001 | Luber et al. | |
| 6,305,565 B1* | 10/2001 | Boyd ............... | H01L 21/67196 |
| | | | 220/676 |
| 7,428,446 B2 | 9/2008 | Crowder et al. | |
| 8,101,244 B2 | 1/2012 | Clarke et al. | |
| 8,252,234 B2 | 8/2012 | Clarke et al. | |
| 8,313,768 B2 | 11/2012 | Kriksunov et al. | |
| 8,888,480 B2* | 11/2014 | Yoo ....................... | B33Y 40/00 |
| | | | 425/375 |
| 9,202,719 B2 | 12/2015 | Lu et al. | |

| | | | |
|---|---|---|---|
| 9,217,700 B2 | 12/2015 | Zhou et al. | |
| 9,381,154 B2 | 7/2016 | Zhou et al. | |
| 9,475,233 B2* | 10/2016 | Schmehl ............... | B29C 64/393 |
| 9,511,028 B2 | 12/2016 | Chen et al. | |
| 9,725,247 B2 | 8/2017 | Trebbi et al. | |
| 10,008,915 B2 | 6/2018 | Lu et al. | |
| 10,059,057 B2* | 8/2018 | Schirtzinger ......... | B29C 70/688 |
| 10,106,331 B2 | 10/2018 | Radak et al. | |
| 10,118,775 B2 | 11/2018 | Walter et al. | |
| 10,239,707 B2 | 3/2019 | Caveney | |
| 10,246,266 B2 | 4/2019 | Weber et al. | |
| 10,250,176 B2 | 4/2019 | Faschang et al. | |
| 10,259,164 B2 | 4/2019 | Bader et al. | |
| 10,272,492 B2* | 4/2019 | Gibson ................. | B29C 64/147 |
| 10,312,787 B2 | 6/2019 | Paweletz et al. | |
| 10,370,195 B2 | 8/2019 | Huber | |
| 10,421,265 B2 | 9/2019 | Houben et al. | |
| 10,454,355 B2 | 10/2019 | Weber et al. | |
| 10,476,413 B2 | 11/2019 | Weber et al. | |
| 10,493,026 B2 | 12/2019 | Koll et al. | |
| 10,532,891 B2 | 1/2020 | Walter et al. | |
| 10,554,102 B2 | 2/2020 | Weber et al. | |
| 10,554,111 B2 | 2/2020 | Weber et al. | |
| 10,562,059 B2 | 2/2020 | Beck et al. | |
| 10,594,245 B2 | 3/2020 | Plainer et al. | |
| 10,608,518 B2 | 3/2020 | Brucker et al. | |
| 10,618,750 B2 | 4/2020 | Brucker et al. | |
| 10,622,921 B2 | 4/2020 | Weber et al. | |
| 10,826,370 B2 | 11/2020 | Huber et al. | |
| 10,848,047 B2 | 11/2020 | Weber et al. | |
| 10,850,236 B2 | 12/2020 | Paschkewitz et al. | |
| 10,889,133 B2 | 1/2021 | Jackson et al. | |
| 10,913,362 B2 | 2/2021 | Holzleitner et al. | |
| 10,917,027 B2 | 2/2021 | Weber et al. | |
| 10,923,997 B2 | 2/2021 | Hoeck et al. | |
| 10,926,418 B2 | 2/2021 | Lu et al. | |
| 10,933,636 B2 | 3/2021 | Volkel et al. | |
| 10,978,969 B2 | 4/2021 | Weber et al. | |
| 10,994,943 B2 | 5/2021 | Huber et al. | |
| 11,142,353 B2 | 10/2021 | Parietti et al. | |
| 11,146,160 B2 | 10/2021 | Frangen | |
| 11,161,202 B2 | 11/2021 | Shibazaki | |
| 11,161,700 B2 | 11/2021 | Weber | |
| 11,161,701 B2 | 11/2021 | Weber | |
| 11,193,812 B2 | 12/2021 | Derrick | |
| 11,196,329 B2 | 12/2021 | Lu | |
| 11,229,577 B2 | 1/2022 | Schiller et al. | |
| 11,383,440 B2 | 7/2022 | Jackson et al. | |
| 11,413,790 B2 | 8/2022 | Swartz et al. | |
| 11,430,683 B2 | 8/2022 | Raatz et al. | |
| 11,434,032 B2 | 9/2022 | Sanmartin | |
| 11,451,169 B2 | 9/2022 | Wierzbicki et al. | |
| 11,465,354 B2* | 10/2022 | Sinha .................... | B29C 64/188 |
| 11,685,118 B2* | 6/2023 | Plummer ............... | B22F 12/52 |
| | | | 425/78 |
| 11,796,981 B2* | 10/2023 | Sennoun ............... | B33Y 50/02 |
| 12,358,049 B2* | 7/2025 | Myerberg ............... | B22F 10/20 |
| 2002/0182782 A1* | 12/2002 | Farnworth .......... | H01L 23/3121 |
| | | | 438/114 |
| 2007/0238056 A1 | 10/2007 | Baumann et al. | |
| 2009/0022571 A1 | 1/2009 | Krupyshev et al. | |
| 2009/0060983 A1 | 3/2009 | Bunick et al. | |
| 2010/0123764 A1* | 5/2010 | Slotto .................. | B41J 2/17593 |
| | | | 347/90 |
| 2011/0025153 A1 | 2/2011 | Simeray | |
| 2012/0092416 A1 | 4/2012 | Platt et al. | |
| 2013/0069449 A1 | 3/2013 | Pharand et al. | |
| 2014/0065194 A1* | 3/2014 | Yoo ........................ | B29C 64/106 |
| | | | 425/375 |
| 2015/0035206 A1 | 2/2015 | Maggiore | |
| 2015/0333291 A1 | 11/2015 | van Lammeren et al. | |
| 2016/0236419 A1* | 8/2016 | Griffin .................. | B29C 64/141 |
| 2016/0342769 A1 | 11/2016 | DeCiccio et al. | |
| 2017/0128601 A1 | 5/2017 | DeCiccio et al. | |
| 2017/0239892 A1* | 8/2017 | Buller ................ | B28B 17/0081 |
| 2017/0304947 A1 | 10/2017 | Shibazaki | |
| 2018/0120260 A1* | 5/2018 | Goldfine ............ | G01N 27/9046 |
| 2018/0290386 A1 | 10/2018 | DeCiccio et al. | |
| 2019/0374471 A1 | 12/2019 | Basit et al. | |

(56) References Cited

U.S. PATENT DOCUMENTS

| | | | | |
|---|---|---|---|---|
| 2020/0001521 A1* | 1/2020 | Yoo | ........................ | B33Y 10/00 |
| 2020/0028427 A1 | 1/2020 | Hoeck et al. | | |
| 2020/0030995 A1 | 1/2020 | Lu et al. | | |
| 2020/0031591 A1 | 1/2020 | Huber et al. | | |
| 2020/0036276 A1 | 1/2020 | Huber et al. | | |
| 2020/0108553 A1* | 4/2020 | Rogren | ................. | B33Y 50/02 |
| 2020/0287493 A1 | 9/2020 | Flixeder et al. | | |
| 2020/0391437 A1 | 12/2020 | Stirling | | |
| 2021/0003444 A1 | 1/2021 | Derrick | | |
| 2021/0036583 A1 | 2/2021 | Forthuber | | |
| 2021/0124337 A1 | 4/2021 | Zehnder et al. | | |
| 2021/0152062 A1 | 5/2021 | Stuart | | |
| 2021/0155422 A1 | 5/2021 | Kastinger et al. | | |
| 2021/0167713 A1 | 6/2021 | Kaufleitner et al. | | |
| 2021/0196572 A1 | 7/2021 | Huang et al. | | |
| 2021/0205176 A1 | 7/2021 | Huang et al. | | |
| 2021/0205228 A1 | 7/2021 | Huang et al. | | |
| 2021/0213678 A1 | 7/2021 | Huang et al. | | |
| 2021/0221008 A1 | 7/2021 | Lu et al. | | |
| 2021/0237981 A1 | 8/2021 | Huber et al. | | |
| 2021/0265188 A1* | 8/2021 | Moura | ................... | G05D 3/125 |
| 2021/0331392 A1 | 10/2021 | Herzog et al. | | |
| 2021/0331878 A1 | 10/2021 | Hauer et al. | | |
| 2021/0336522 A1 | 10/2021 | Flixeder et al. | | |
| 2021/0348314 A1 | 11/2021 | Jarrell et al. | | |
| 2021/0376777 A1 | 12/2021 | Lu et al. | | |
| 2022/0048108 A1 | 2/2022 | Oohashi | | |
| 2022/0062180 A1 | 3/2022 | Slocum et al. | | |
| 2022/0088871 A1 | 3/2022 | Kim et al. | | |
| 2022/0184891 A1 | 6/2022 | Novick | | |
| 2022/0266371 A1* | 8/2022 | Kruer | ..................... | B23K 9/167 |
| 2022/0306406 A1 | 9/2022 | Flixeder et al. | | |
| 2023/0129915 A1* | 4/2023 | Young | ..................... | B22F 10/38 |
| 2023/0191543 A1* | 6/2023 | Feied | ..................... | B23P 23/02 |
| | | | | 29/33 R |
| 2023/0373158 A1* | 11/2023 | Steege | ................. | B29C 64/165 |
| 2023/0420289 A1* | 12/2023 | Leeser | .............. | H01L 21/68735 |
| 2024/0051695 A1 | 2/2024 | Mondini et al. | | |
| 2024/0326328 A1 | 10/2024 | Bromberg et al. | | |

FOREIGN PATENT DOCUMENTS

| | | | | | |
|---|---|---|---|---|---|
| KR | 20110045955 | * | 6/2011 | ............. | B61B 13/00 |
| WO | 2005123569 | A2 | 12/2005 | | |
| WO | 2005124297 | A2 | 12/2005 | | |
| WO | 2006058247 | A2 | 6/2006 | | |
| WO | 2014039378 | A1 | 3/2014 | | |
| WO | 2014071135 | A1 | 5/2014 | | |
| WO | 2014143935 | A1 | 9/2014 | | |
| WO | 2014144512 | A1 | 9/2014 | | |
| WO | 2014144661 | A1 | 9/2014 | | |
| WO | 2015143553 | A1 | 10/2015 | | |
| WO | 2015159300 | A1 | 10/2015 | | |
| WO | 2016038356 | A1 | 3/2016 | | |
| WO | 2017034951 | A1 | 3/2017 | | |
| WO | 2017190994 | A1 | 11/2017 | | |
| WO | 2018096363 | A1 | 5/2018 | | |
| WO | 2018176137 | A1 | 10/2018 | | |
| WO | 2018206497 | A2 | 11/2018 | | |
| WO | 2020073118 | A1 | 4/2020 | | |
| WO | 2020081561 | A1 | 4/2020 | | |
| WO | 2020240028 | A1 | 12/2020 | | |
| WO | 2020240029 | A1 | 12/2020 | | |
| WO | 2020240030 | A1 | 12/2020 | | |
| WO | 2020243814 | A1 | 12/2020 | | |
| WO | 2021115887 | A1 | 6/2021 | | |
| WO | 2021119819 | A1 | 6/2021 | | |
| WO | 2021198308 | A1 | 10/2021 | | |
| WO | 2021211898 | A2 | 10/2021 | | |
| WO | 2021263132 | A1 | 12/2021 | | |
| WO | 2022094376 | A2 | 5/2022 | | |
| WO | 2023094674 | A1 | 6/2023 | | |

OTHER PUBLICATIONS

Beckhoff, "XPlanar—Planar motor system", first accessible May 28, 2022 according to Wayback machine, Beckhoff Automation LLC, https://www.beckhoff.com/en-us/products/motion/xplanar-planar-motor-system/ (4 pages).

Festo, "SupraMotion", first accessible Dec. 8, 2021 according to Wayback machine, Festo Corporation, https://www.festo.com/us/en/e/about-festo/research-and-development/supramotion-id_9881/ (5 pages).

Festo South Africa, "Motion Cube for individualised mass production", May 2016, South African Instrumentation and Control, Technews Publishing Pty Ltd, https://www.instrumentation.co.za/54427n (2 pages).

Castelo, "Festo Motion Cube, excerpt", Oct. 19, 2015, YouTube, https://youtu.be/RKkZuEB9jBk?si=gfrxhvrM3xSLj6Yh (1 page).

International Search Report and Written Opinion dated Dec. 4, 2024 in related International Application No. PCT/US2024/052019 filed Oct. 18, 2024 (10 pages).

Wikipedia, Process analytical technology, https://en.wikipedia.org/wiki/Process_analytical_technology, Sep. 2006, Veion as of Dec. 2023 submitted (4 pages).

Wahl, DI Patrick, Dissertation "Measuring and Controlling Critical Process Parameters of Pharmaceutical Manufacturing by PAT", Research Center Pharmaceutical Engineering, TU Graz, Mar. 2014, (165 pages).

Tan et al., "Pilot-scale binder jet 3D printing of sustained release solid dosage forms", Int'l Journal of Pharmaceutics, Dec. 23, 2022, vol. 631, No. 122540 (8 pages).

* cited by examiner

SYSTEM AND METHOD FOR ADDITIVE MANUFACTURING USING AN OMNIDIRECTIONAL MAGNETIC MOVEMENT APPARATUS

CROSS-REFERENCE TO EARLIER FILED APPLICATIONS

The present application is a continuation of U.S. application Ser. No. 18/704,601 filed Apr. 25, 2024, now abandoned, which is a national stage entry of International Application No. PCT/US2023/018495 filed Apr. 13, 2023, which claims the benefits of U.S. Provisional Application No. 63/330,667 filed Apr. 13, 2022, U.S. Provisional Application No. 63/416,585 filed Oct. 16, 2022, and U.S. Provisional Application No. 63/455,281 filed Mar. 29, 2023, the entire disclosures of which are hereby incorporated by reference.

FIELD OF THE INVENTION

The present invention relates to the use of an omnidirectional magnetic movement apparatus for forming articles, such as dosage forms using additive manufacturing techniques.

BACKGROUND OF THE INVENTION

The industrial manufacture of pharmaceutical dosage forms is well-known in the art and has been practiced for over 100 years. The current state of the art in oral solid dose pharmaceutical unit operation manufacturing is to incorporate a series of independent activities, which can be run either in batch mode or continuously in series, using a variety of different process unit operations, including powder dispensing, powder blending, powder milling, granulation by either wet or dry means, compression or encapsulation, coating, and packaging of dosage forms. The process unit operations are carried out on large-scale equipment independently operated and often in large physical spaces located proximately or distant from one another and utilizing linear and/or circuitous, intermittent, or continuous processes. This traditional alignment or relationship between operations has resulted in a need to build separate pieces of equipment, rooms, and, in some instances, entire facilities for production of new or generic pharmaceutical dosage forms.

Magnetic movement apparatuses are well known in the prior art. For example, U.S. Pat. No. 9,202,719, the disclosure of which is incorporated by reference in its entirety, discloses the basic structure and mode of operation of an omnidirectional magnetic movement apparatus, also known as a planar motor. An omnidirectional magnetic movement apparatus or system enables the asynchronous and/or random movement, positioning, and orientation of one or more shuttles, by the guidance system along and over the planar transport surface of the stator. WO 2018/176137 A1, the disclosure of which is incorporated by reference in its entirety, discloses a magnetic movement apparatus with numerous differently designed shuttles and stators, and teaches how to secure the stator with guideways in a transfer region between a stator of the magnetic movement apparatus and a statorless transport system (e.g., a conveyor belt, robot gripper or similar), so that the shuttle is first floated from the stator into the guideway, then slides on the guideway (e.g., on rollers) and is moved along by the statorless transport system when it has left the region of the magnetic action of the stator.

SUMMARY OF THE INVENTION

The present invention provides a processing system and a method for forming articles or for processing of materials or components of articles, including by, though not limited to, additive manufacturing (including three-dimensional printing, or "3DP") that includes one or more process unit operations, an omnidirectional magnetic movement apparatus that includes a magnetic field-generating stator having a planar transport surface, and one or more fabrication modules that incorporate one or more magnetic field-actuated shuttles that move by magnetic levitation over the planar transport surface in six degrees of movement, including in a horizontal direction in the x,y axes and in a vertical direction in the z axis. A movement controller comprising one or more processors and one or more sensors controls movement omnidirectionally of the one or more shuttles over the planar transport surface. A controller system provides a method for monitoring and controlling the processing of materials, including the quality of the processes, the quality and characteristics of the build material inputs, and the quality and characteristics of the articles produced by the unit operations and the processing system.

The maneuvering of one or more substrates being carried by a fabrication module and moved by one or more shuttles enables an asynchronous and/or selective movement, positioning, and orientation of the one or more substrates to and between one or more process unit operations, and the forming or processing of one or more articles upon a substrate. The incorporation of one or more, and typically a plurality of, process unit operations with an omnidirectional magnetic movement system can provide a means for optimizing the size, production speed, and flexibility to manufacture individual articles, for a non-limiting example, pharmaceutical dosage forms, at a rate and capacity equivalent to, or higher than, that achieved through traditional process unit operations.

In various embodiments, the process unit operation system is designed and constructed to enable and optimize flexibility in the number and type of individual process unit operations and operation equipment deployed with the omnidirectional magnetic movement system, at a given time. By way of example, the process system can provide and incorporate multiple construction materials at one time, using material deposition modules. The modules function to deposit the same or equivalent construction materials, or different construction materials, which may vary in physical state, from solid particles, semi-solid solution or suspensions, liquids, or any combination thereof.

Similarly, the apparatus can be designed and constructed to deploy a variety of liquid dispensing and/or printing technologies used in the formation of an article, for example, piezo ink jet printing, material jetting, fused deposition, extrusion, and hot melt extrusion.

Similarly, the apparatus can be designed and constructed to deploy a variety of process analytical technologies used in the instantaneous, continuous, or intermittent monitoring and control, including closed loop feedback control of the quality and consistency of processes and outputs from same, for example, Near IR (NIR) and Short Wave IR (SWIR) spectrometers, 2D and 3D cameras which may incorporate artificial intelligence (AI) and machine learning functionality.

The modular design enables rapid, instantaneous, change in process unit operation utilization, functionality and maintenance without or with less time-consuming disassembly and reassembly of the equipment and assemblies typically associated with traditional individual, serial and parallel processing technology product manufacturing assemblies. Further, the modular design of the processing system of the present invention can be used for development, simulation, testing, experimentation, and similar activities on a smaller, more efficient production scale, which allows qualification of processes on equipment or modules of equipment that may be the exact same equipment of modules deployed in pilot or commercial scale manufacturing. The modularity allows for thorough and systematic testing and development of process and operating conditions of an equipment or module of equipment, before installing the same equipment or module of equipment into a GMP-rated pilot or manufacturing facility. The modularity also allows an equipment or module of equipment to be withdrawn from a GMP-rated pilot or manufacturing facility and placed into the processing facility for dynamic simulation of the process on the smaller scale to aid in processing adjustments and troubleshooting of process anomalies, and returning the same equipment or module of equipment to the pilot or manufacturing facility.

A non-limiting variety of sub-processing systems can include systems for processing gaseous, particular, solid or liquid materials and compositions by one or more of conveying, mixing, blending, dispensing, printing, leveling, irradiating, heating, boiling, cooling, freezing, evaporating, pressurizing, vacuuming, blanketing with a gas, sealing (of one element to another), dehumidifying, venting or purging of a gas or vapor, and other process unit operations for forming of an article upon or within a substrate.

In various embodiments, the one or more process unit operations include a deposition system for a construction material, and a phase modification system for forming the construction material into an article. The one or more process unit operations can include a three-dimensional printing (3DP) or other additive manufacturing process operation. An article can be any solid, semi-solid, semi-liquid or liquid product, and can include a medicament form, a pharmaceutical or medicament dosage form, and a household, industrial or commercial product.

Non-limiting examples of a substrate on or within which an article can be formed can include a tray, a container, a sheet, a mold part, and a package material, more particularly a blister card.

The present invention provides a process system for making an article, comprising: i) an omnidirectional magnetic movement apparatus comprising a transport surface; ii) one or more fabrication modules comprising a) at least one shuttle, and b) at least one substrate comprising one or more formation surface; iii) an article forming system comprising: a) at least one depositing device for placing a construction material onto at least one of the one or more formation surfaces when the shuttle is positioned at a deposition position of the transport surface; and b) at least one processing device for performing a process unit operation on the construction material when the shuttle is disposed at a processing position of the transport surface; and iv) a movement controller to control the transportation omnidirectionally and asynchronously of the one or more fabrication modules over the transport surface between at least the deposition position and the at least one processing position for forming the article.

The present invention also provides one or more additional processes or procedures for efficiently and effectively forming the articles of the invention. In some embodiments, the process system includes an inspection system positioned over one or more inspection stations, the one or more inspection systems including one or more sensors or detectors, each of which may be AI and/or machine learning based. The method of forming an article can include performing an in-line, instantaneous analytical evaluation of a physical and/or chemical property of an article (for example, a tablet form) and the intermediate forms, and either confirming the acceptability of a completely or partially formed article or product, or determining the necessity of re-working of a step or unit operation process of the completely or partially formed article, to create an acceptable completed article or product. In some embodiments, the inspection method and system can detect physical properties of an article, such as an article (for example, tablet) or of an intermediate form thereof, or can detect processing conditions and parameters, such as liquid deposition positioning, specific compound content or uniformity, individual layer or total dosage spatial volume, residual solvent/moisture content, and fractured or damaged dosage forms. Non-limiting examples of a process performed on an article or intermediate form thereof can include tamping, compacting, etching, engraving, labeling, coloring, and visible printing. Following an inspection and evaluation of the inspection result, the fabrication module with the substrate and processed article, and as an example of asymmetric processing, can be directed back to one of the unit operation stations for further processing in accordance with the inspection result.

Once the unit operation processing is entirely completed, the fabrication module with the substrate and article can be moved under the control of both the process unit operations controller and the movement controller to exit the unit operation processing system, and moved off the magnetic movement apparatus for further processing, inspection, packaging, handling, and distribution.

The omnidirectional magnetic movement system provides a trackless conveying system that allows the flexible integration of a series of process unit operations performed by devices and apparatus. The omnidirectional magnetic movement apparatus comprises a plurality of areal tile segments, typically a square shape of uniform dimension, arranged side by side with one or more adjacent tile segments. Various layouts and patterns of the tile segments of the magnetic movement apparatus provide flexible and instantaneous changes in process unit operations that are unavailable with a linear track or conveyor system. In some embodiments, the transport surface of the magnetic movement apparatus or system is an enlarged open area, such as in the shape of a square or rectangle, or circle or oval, and control of the movement of shuttles is controlled to restrict or prevent movement of the shuttles into specified areas above the actuation coils. In other embodiments, the tile segments can be arranged into a variety of patterns to provide an island or a peninsula of non-tiled area within or internal to the outer periphery of the tiled pattern, which movement of shuttles is prohibited. For example, the tile pattern can include a main elongated zone and a plurality of tiled segments that extend laterally from the main elongated zone.

The movement controller of the omnidirectional magnetic movement system comprises one or more processors and one or more sensors for detecting the real-time position of the one or more shuttles, each having a unique identification address, and moving the one or more shuttles over the planar transport surface in accordance with instructions provided by a processing controller to form articles upon a substrate associated with the one or more shuttles.

The incorporation of the dosage-forming process unit operations of a construction material dispensing system and a phase modification system, with an omnidirectional magnetic movement system, provides a means for optimizing the size, production speed, and flexibility to manufacture individual articles, for example, pharmaceutical dosage forms, at a rate and capacity equivalent to, or higher than, that achieved through traditional process unit operations.

The process system moves formation substrates with their construction material and/or intermediate articles intelligently and efficiently under the control of a process unit operations controller and the movement controller of the omnidirectional magnetic movement system to enable an asymmetric processing of articles, by the movement of the shuttles carrying the substrates to a precise and sometime asynchronous location, position and orientation, and at a precise and sometimes asynchronous time needed for processing. The process system and its controllers maneuver multiple independent fabrication modules through the process unit operation systems while maintaining continuous and/or efficient utilization of each individual process unit operation. The process system and its controllers enable, as may be required, a rework of certain articles on certain fabrication modules simultaneously with the programmed processing routines for other fabrication modules.

Association of the fabrication modules, with the control systems, and each individual substrate (e.g., blister card) and/or formation surface (e.g., depression) with its respective shuttle, allows the system sensors and controllers to track and record historically and precisely the movements of the fabrication modules and its respective shuttle, substrate and formation surface, over the transport surface to process positions of equipment, and the process unit operations performed thereon. Movement of the shuttles and their respective formation modules are controlled to move independently between unit operation positions on the transport surface based on calculated available space around other fabrication modules moving on the transport surface, travel speed, planned unit operation duration(s), and other factors, to determine and execute through the movement controller the optimal pathway over the transport surface to each process station while avoiding collision with other shuttles and fabrication modules, and to maximize the article fabrication throughput from the process system.

The present invention also provides a production system comprising one or more, and typically a plurality of, production modules, the one or more production modules utilizing an omnidirectional magnetic movement system. One non-limiting example of a production module is a substrate forming system for forming a substrate from a stock material, and placing or positioning the formed substrate onto a carrier. Another non-limiting example of a production module is a packaging module for applying one or more packaging elements onto an article-loaded substrate, and/or placing of the article-loaded substrate into an outer packaging material. Another non-limiting example of a production module is separate processing system for performing one or more process unit operation in concert with an article-forming process system, a non-limiting example of which is system and method for printing or placing an identification marking onto a substrate or a formation surface of a substrate.

The present invention also provides a containment system and associated equipment including a containment housing to provide a containment zone above the transport surface of the stator. The containment housing has one or more transport openings within a sidewall of the containment housing to provide entry and/or egress for a fabrication module into and out of the containment zone, and one or more sealable openings through a ceiling or sidewall of the containment housing, to provide unit operation processing equipment access to the production system and the fabrication modules within the containment zone. The containment housing can also have one or more airflow openings to allow ambient air, or conditioned gases or air (hereinafter referred to as "outside air") from outside the containment housing, to pass into and through the containment zone (referred to within the containment housing as "process air"). The one or more airflow openings are placed at various positions along the containment housing to control where and how much outside air is drawn into the containment housing, and where and how the process air passes through the containment zone. An air handling and filtration system that includes an air handling and filtration apparatus (hereinafter, "air processing apparatus") draws outside air into the containment zone and the process air through the containment zone. The process air can contain air-borne, entrained and suspended particles, dust, and liquid droplets. The air handling apparatus is configured and operated to maintain a negative air pressure within the containment housing that ensures that any exchange of air will be from outside the containment housing to inside the containment housing, and from inside the containment housing through the air processing apparatus.

In various embodiments, the containment housing is designed and constructed to have a vertical height sufficient to allow movement of the fabrication modules over the transport surface and beneath the process unit operation equipment that penetrate the ceiling and/or sidewalls of the containment housing. In some embodiments, the air flow velocity within the containment zone, particularly a horizontal airflow velocity, is controlled in the containment housing to provide effective entrainment and collection of droplets, particulates, and a mixture thereof, without affecting the process unit operations or the articles being formed on the substrates of the formation modules. In some embodiments a ratio of the vertical height (or the average vertical height) of the containment housing to the area of the containment housing is typically at least 0.1 $cm/m^2$, and up to 100 $cm/m^2$, while a ratio of the vertical height (or the average vertical height) to the width (shorter lateral dimension) of the containment housing is at least 0.5 cm/m, and up to 20 cm/m.

<1a> A non-limiting embodiment of the invention provides a process system for making an article, comprising: i) an omnidirectional magnetic movement apparatus comprising a transport surface and a stator disposed on an underside of the transport surface and comprising a plurality of actuation coil that exerts a primary magnetic field through the transport surface in response to a controlled current through an actuation circuit; ii) one or more fabrication modules comprising a) at least one shuttle comprising a planar body and one or more magnetic components that respond to the primary magnetic field exerted by the plurality of actuation coils to levitate and transport the at least one shuttle omnidirectionally above and over the transport surface, and b) at least one substrate comprising one or more formation surface; iii) a movement controller for sending a controlled current through one or more of the plurality of actuation coils to control the levitation and transportation of the one or more fabrication module; and iv) an article forming system comprising: a) a depositing device for placing a construction material onto at least one of the one or more formation surfaces when the fabrication module is positioned at a deposition position of the transport surface; and b) a phase modifying device for forming at least a portion of the deposited construction material into an article within the at least one of the one or more formation surfaces when the fabrication module is positioned at a phase modification position on the transport surface. In some embodiments, the movement controller is configured to include one or more steps of transporting the one or more fabrication module asynchronously between at least the deposition position and the phase modification position, for forming the article.

<1b> A non-limiting embodiment of the invention provides a process system for making an article, comprising: i) an omnidirectional magnetic movement apparatus comprising a transport surface and a stator disposed on an underside of the transport surface; ii) one or more fabrication modules comprising a) at least one shuttle, and b) at least one substrate comprising one or more formation surfaces; iii) an article forming system comprising: a) at least one depositing device for placing a construction material onto at least one of the one or more formation surfaces when the shuttle is disposed at a deposition position of the transport surface; and b) at least one processing device for performing a process unit operation on the construction material when the shuttle is disposed at a processing position of the transport surface; and iv) a movement controller to control the transportation of the one or more fabrication modules over the transport surface asynchronously between at least the deposition position and the at least one processing position for forming the article. The stator comprises a plurality of actuation coils that exert a primary magnetic field through the transport surface in response to a controlled circuit current through an actuation circuit. The shuttle comprises a planar body and one or more magnetic components that respond to the primary magnetic field exerted by the plurality of actuation coils to levitate and transport the at least one shuttle omnidirectionally above and over the transport surface.

<1c> A non-limiting embodiment of the invention provides a processing system comprising: i) an omnidirectional magnetic movement apparatus comprising a transport surface; ii) one or more fabrication modules comprising a) at least one shuttle comprising a planar body and one or more magnetic components that interact with the magnetic movement apparatus to levitate and transport the at least one shuttle omnidirectionally above and over the transport surface, and b) at least one substrate comprising one or more formation surfaces; iii) an article-forming system comprising: a) a depositing device for placing a construction material onto at least one of the one or more formation surfaces when the shuttle is positioned at a deposition position of the transport surface; and b) a phase modifying device for forming at least a portion of the deposited construction material into an article within the at least one of the one or more formation surfaces when the shuttle is positioned at a phase modification position on the transport surface; and iv) a control system for controlling the depositing device and the phase modifying device of the article-forming system and the movement of the one or more fabrication module over the transport surface of the omnidirectional magnetic movement apparatus, wherein the movement controller is configured to include one or more steps of transporting the one or more fabrication modules asynchronously between at least the deposition position and the phase modification position, for forming the article.

<1d> In some embodiments, the present invention provides a process system for the manufacture of an article, including by one or more process unit operations. The AM system comprises: i) a horizontal planar transport surface having a periphery that extends in a first direction and a transverse second direction, and having an upper transport side and an underside; ii) a stator disposed on the underside of the transport surface, comprising a plurality of primary pairs of a primary actuation circuit and a primary actuation coil that exerts a primary magnetic field through the transport surface and to the upper transport side, in response to a controlled current through the actuation circuit; iii) one or more fabrication modules comprising a) at least one shuttle comprising a planar body and one or more magnetic components that interact with the plurality of actuation coils to levitate and transport the at least one shuttle omnidirectionally above and over the transport surface, and b) at least one substrate comprising one or more formation surfaces; iv) a movement controller for sending the controlled current through one or more of the plurality of actuation coils to control the levitation and transportation of the one or more fabrication modules, the transporting of the shuttle including: a) a movement of the shuttle in the first direction, the second direction, or a combination thereof, between two or more positions upon the transport surface, b) a rotation of the shuttle around at least one orthogonal axis of the shuttle, and c) a combination thereof; v) an article-forming system comprising: a) a depositing device for placing a construction material onto at least one of the one or more formation surfaces when the shuttle is positioned at a deposition position of the transport surface; and b) a phase modification device for forming at least a portion of the deposited construction material into an article form within the at least one of the one or more formation surfaces when the shuttle is positioned at a phase modification position on the transport surface; wherein the movement controller is configured to include one or more steps of transporting the one or more fabrication modules asynchronously between at least the deposition position and the phase modification position, for forming the article.

<1e> An embodiment of the invention provides a process system for making an article, comprising: i) an omnidirectional magnetic movement apparatus comprising a transport surface and a stator disposed on an underside of the transport surface and comprising a plurality of actuation coils that exerts a primary magnetic field through the transport surface in response to a controlled current through an actuation circuit; ii) one or more fabrication modules comprising a) at least one shuttle comprising a planar body and one or more magnetic components that respond to the primary magnetic field exerted by the plurality of actuation coils to levitate and transport the at least one shuttle omnidirectionally above and over the transport surface, and b) at least one substrate comprising one or more formation surfaces; iii) a movement controller for sending a controlled current through one or more of the plurality of actuation coils to control the levitation and transportation of the one or more fabrication modules; and iv) an article forming system comprising: a) a depositing device for placing a construction material onto at least one of the one or more formation surfaces when the fabrication module is positioned at a deposition position of the transport surface; and b) a phase modification device for forming at least a portion of the deposited construction material into an article within the at least one of the one or more formation surfaces when the fabrication module is positioned at a phase modification position on the transport surface; wherein the movement controller is configured to include one or more steps of transporting the one or more fabrication module asynchronously between at least the deposition position and the phase modification position, for forming the article.

<1> An embodiment of the invention can include any of features <1a> through <1e>.

<2> In any of the embodiments of features <1a> through <2>, the movement controller is configured to include one or more steps of transporting the one or more fabrication module asynchronously between at least the deposition position and the phase modification position, for forming the intermediate or finished article.

<3> In any of the embodiments of features <1a> through <3>, the transport surface comprises a non-conductive contiguously-formed sheet, wherein the sheet can be made of a material selected from the group consisting of a polymer, glass, titanium, and stainless-steel.

<4> In any of the embodiments of features <1a> through <3>, the transport surface is a rectangular area including a central area and a peripheral area, and optionally, the transport surface is a rectangular area including a central area and a peripheral area and such area may have its surface temperature controlled by circulation of appropriate heat transfer medium through the interior regions of the stator to control and maintain the temperature of the transport surface, and the peripheral area has a width dimension that is at least a width of the fabrication module, and central area is at least a width of the fabrication module.

In any of the embodiments of features <1a> through <4>, the stator includes a set of a plurality of second pairs of a second actuation circuit and a second actuation coil that exerts a second magnetic field through the transport surface and to the upper transport side, in response to a controlled current through the actuation circuit, a force of the second magnetic field being greater than the first magnetic field.

<5> In any of the embodiments of features <1a> through <5>, the one or more fabrication modules further comprises a carrier for fixing the substrate onto the at least one shuttle.

<6> In any of the embodiments of features <1a> through <5>, the one or more formation surfaces comprises one or more depressions.

In any of the embodiments of features <1a> through <6>, the step of transporting of the shuttle further includes a pivoting of the shuttle around a horizontal axis through the shuttle, a vertical axis through the shuttle, or a combination of both horizontal and vertical axes, sufficient to effect a change in the distribution of the deposited construction material onto the one or more formation surfaces, and preferably comprises leveling of the deposited construction material to a uniform thickness by controlling at least one or more of the factors of pivot angle, acceleration, and frequency.

In any of the embodiments of features <1a> through <6>, the movement of each of the plurality of fabrication modules to and from each of the deposition position and the phase modification position is independent and selective, to provide for the capability of asynchronous forming of the dosage forms on the at least one substrate of two different fabrication modules.

In any of the embodiments of features <1a> through <6>, the depositing device places the construction material onto the one or more formation surfaces based on at least one of volume and mass.

<7> In any of the embodiments of features <1a> through <6>, the one or more fabrication modules comprises a plurality of fabrication modules, and the movement of each of the plurality of fabrication modules to and from each of the deposition position and the phase modification position is independent and selective, to provide for the capability of asynchronous forming of the articles on the at least one substrate of two different fabrication modules <8> In any of the embodiments of features <1a> through <7>, the process system or sub-process system further includes a means for leveling of the deposited construction material to a uniform thickness.

<9> In any of the embodiments of features <1a> through <8>, the process system or sub-process system further includes one or more additional processing devices selected from the group consisting of a drying device, a construction material leveling device, a surface finishing apparatus, a substrate loading device, a substrate unloading device, and a combination thereof.

<10> In any of the embodiments of features <1a> through <9>, the process system or sub-process further includes a surface finishing apparatus for surface finishing an upper surface of at least one of the deposited construction material or the solid dosage form within the formation surface when the shuttle is positioned at a surface finishing position on the transport surface.

<11> In any of the embodiments of features <1a> through <10>, the process system or sub-process further includes a deposition sensing device for detecting the uniformity of distribution of the deposited construction material to one or more formation surfaces.

<12> In any of the embodiments of features <1a> through <11>, the construction material can comprise an ingestible powder material; the construction material or the ingestible powder material can comprise an active agent, a non-limiting example of which is an API, a biological material, or medicament. The article can be a solid dosage form and the phase modification device comprises a means for dispersing a binding liquid that forms the ingestible powder material into a bound-powder material comprising an interconnected matrix of the ingestible powder material. The build powder material can comprise a particulate binder. The binding liquid can comprise an active agent, a non-limiting example of which is an API or medicament. The binding liquid can comprise a soluble binder material. The interconnected matrix of the build powder material can be porous, and in some embodiments is rapidly orodispersive. The construction material can comprise at least one thermofusable powder material, and the phase modification device can comprise a means for at least partially melting the thermofusable material.

In any of the embodiments of features <1a> through <11>, the process system or sub-process system further includes a device, apparatus, or sub-system for storing, delivering, and/or depositing an auxiliary active agent onto a construction material or phase-modified construction material. A non-limiting example of an active agent is an API or medicament, and/or a material with specific function designed to impart a targeted site or rate of release of a biologically active agent. The auxiliary active agent can optionally be a solid, particulate material or a liquid material, and in either a particulate or liquid form, along with one or more optional solvent, free-flow aid, diluent, and carrier material.

The present invention also provides a method using the omnidirectional magnetic movement system, using a guidance system for transporting a shuttle or shuttles over the stator. The omnidirectional magnetic movement system provides for synchronous and/or asynchronous movement of the shuttle or shuttles, to transport and optimize positional orientation of the shuttle or shuttles transporting the substrate to and between the unit operation processing devices, which, in an example of asynchronous processing, perform corresponding process unit operations upon the substrates in series, in parallel, and/or simultaneously, to optimize processing efficiency and process utilization.

The method and system for movement of the substrate omnidirectionally and asynchronously to and between processing devices provides for processing simultaneously and selectively of one or more articles with one or more process unit operations within small space and in less time than conventional processing systems for the same article.

<13> An embodiment of the present invention provides a method for using of a planar motor system for transporting of one or more fabrication modules through a plurality of process unit operations utilized in the additive manufacture of dosage forms, the transporting controlled (explicitly, or via machine learning, artificial intelligence or other positional scheduling approach) to effect asynchronous, synchronous, and randomized positioning and orientation, to thereby effect asynchronous and simultaneous utilization of the process unit operations in the forming of the dosage forms.

<14> In the embodiment of feature <13>, the plurality of process unit operations includes dispensing of a mass quantity of a construction material onto one or more formation surfaces of a fabrication module, and phase modifying the mass quantity of the construction material disposed on the one or more formation surfaces of the fabrication module into a solid dosage form.

<15> In either of the embodiments of features <13> or <14>, the plurality of process unit operations further includes one or more process unit operations selected from the group consisting of mixing of two or more different construction materials, leveling an upper surface of the mass quantity of the construction material, finishing an outer surface of the solid dosage form, inspecting of one or more physical properties of a material, and cleaning of a contaminated device or equipment used in the method.

<16> In any of the embodiments of features <13> through <15>, the construction material is an ingestible powder material, the phase modifying comprises printing of a liquid material comprising a solvent or other volatile compound onto a layer of the ingestible powder material, and optionally drying of an excess of the solvent or the other volatile compound from a wetted powder layer.

<17> In any of the embodiments of features <13> through <16>, the plurality of process unit operations includes dispensing of a mass quantity of an ingestible powder onto one or more formation surfaces of a fabrication module, leveling an upper surface of the mass quantity of the ingestible powder disposed on the one or more formation surfaces of the fabrication module to form a powder layer, printing of a liquid material comprising a solvent or other volatile compound onto the upper surface of the mass quantity of the disposed powder to form a wetted powder layer on the one or more formation surfaces of the fabrication module, and optionally drying of an excess of the solvent or the other volatile compound from a wetted powder layer.

<18> In any of the embodiments of features <13> through <17>, the method further includes a process unit operation of printing of a liquid material comprising a solvent onto a surface of one or more formation surfaces of the substrate, prior to dispensing of the ingestible powder.

<19> In any of the embodiments of features <13> through <18>, the additive manufacturing of dosage forms is selected from the group consisting of binder jetting, material jetting, stereo lithography, fused deposition, laser sintering, and extrusion.

<20> In any of the embodiments of features <13> through <19>, the cleaning of a device or equipment comprises positioning a cleaning substrate, in sufficient proximity to a specific process unit operation, and spatially manipulating at least one of the cleaning substrates and the contaminated device or equipment, to clean one or more surfaces of the contaminated device or equipment.

DETAILED DESCRIPTION OF THE INVENTION

Definitions

An "active agent" can include, but is not limited to, one or more of a drug, an active pharmaceutical agent (API), a nutritional agent, a pharmaceutically-acceptable agent, a bioactive agent, a therapeutic agent, a diagnostic agent, and an antiseptic or sterilizing agent. An active agent can include a compound or composition that provides a biologic activity within a mammalian or non-mammalian species; for example, a pharmacological activity or other direct effect in the diagnosis, cure, mitigation, treatment, or prevention of disease, or to affect the structure and function of the mammalian or non-mammalian species. A diagnostic agent can include an imaging agent and/or a radioactive labeled compound. An active agent can be a small molecule therapeutic, a peptide, and/or a protein.

As used herein, an "article" is an object or a composition of matter. A non-limiting example of an object is a tablet or an implant. Non-limited examples of a composition of matter are a liquid, a semi-solid, or a solid matter.

As used herein, a "construction material" is a material (a solid, semi-solid, liquid or liquified gas), or a portion thereof, that becomes a part or portion of an article or composition of matter, or an intermediate thereof.

As used herein, a "process unit operation" includes, though not by limitation, a process involving the supply, delivery and dispensing of a construction material or an intermediate article for an article, or a material or composition involved in the processing of an article or intermediate article, or a process involving a physical change or chemical transformation of a compound, composition, or a material, including a construction material, and can include a unit operation as further described herein.

<Omnidirectional Magnetic Movement Apparatus>

Figure 1:
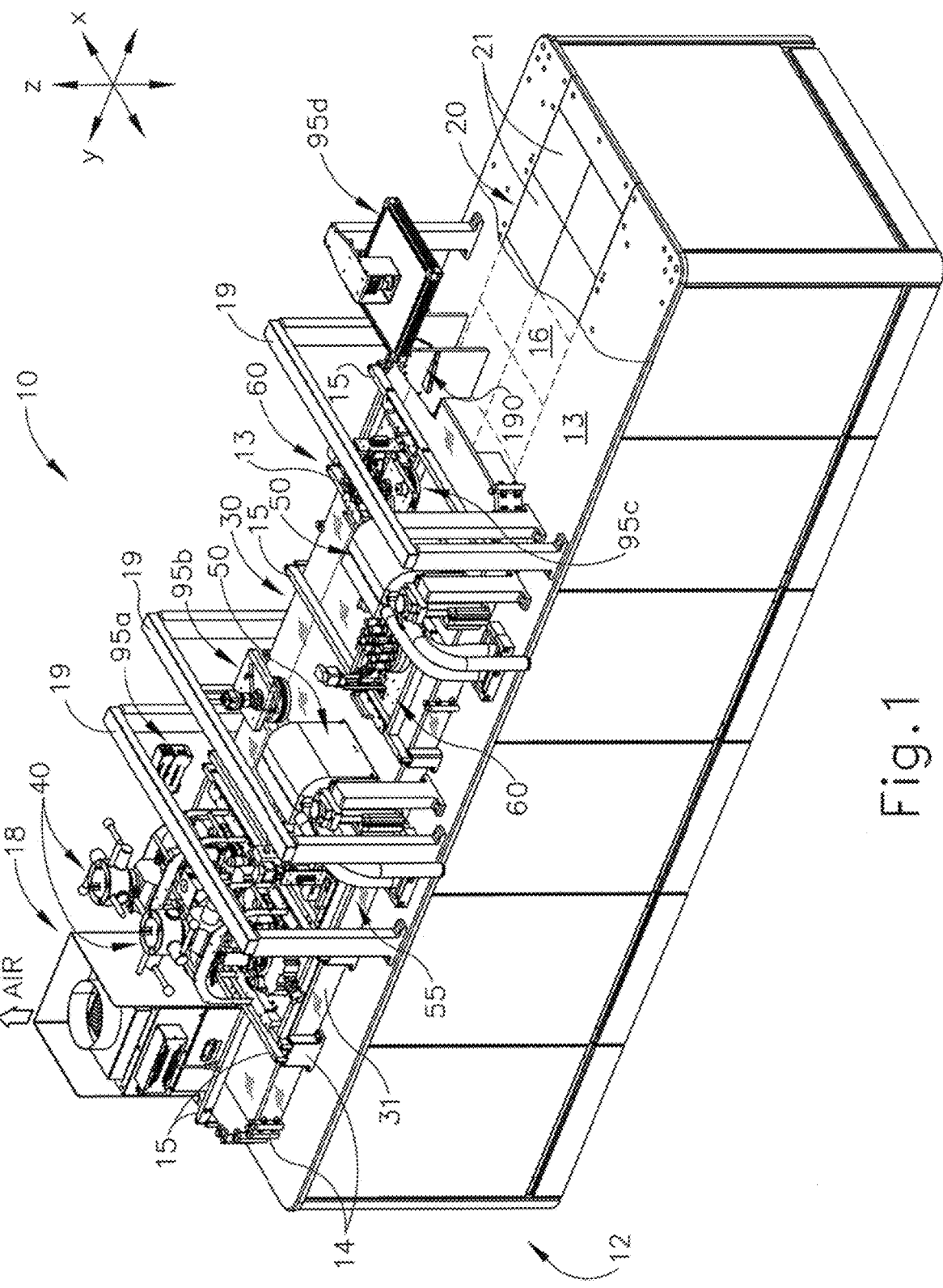
FIG. 1 illustrates a process system having an omnidirectional magnetic movement apparatus, containment system, and several process unit operation systems for forming an article on a transport module.

Referring to FIG. 1, an omnidirectional magnetic movement apparatus 20 has a horizontal and planar (x-y coordinate) transport surface 16 along and above which one or more transport units comprising a permanent (or electro) magnet, identified herein as shuttles, can be transported in the horizontal plane in an x-y direction, to a specified x-y position with a specified x-y orientation. Drive coils positioned below the transport surface, referred to as stators, are controlled by a control unit to generate a changeable and adjustable magnetic field through the transport surface, to levitate and move the one or more shuttles over the transport surface in a desired horizontal direction. Details of the design and construction of an omnidirectional magnetic movement apparatus and system are described in International Patent Publications WO 2018/176137, WO 2020/073118, WO 2020/243814, and WO 2021/119819, the disclosures of which are incorporated by reference in their entireties.

Alternatively, the stators can consist of permanent magnets and the shuttles can be equipped to generate a controlled magnetic field for levitated movement over the stators. However, in connection with the present disclosure, the stators shall be referred to as the assembly of stationary and controllable electromagnets, and the transport unit shall be referred to as the permanent- (or electro-) magnet shuttle moveable over the stator, regardless of the mode of operation.

Figure 2:
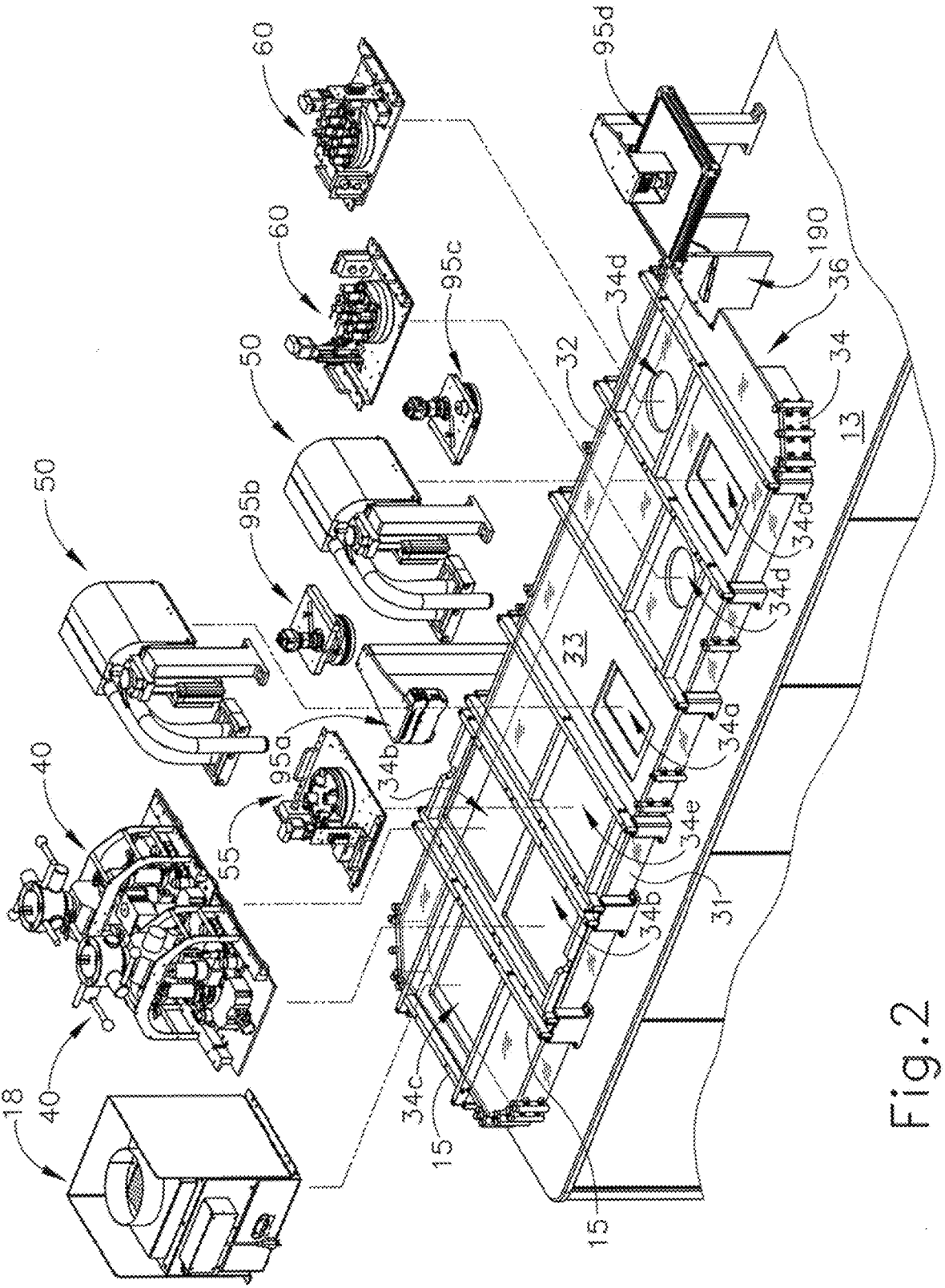
FIG. 2 illustrates the containment housing having access ports for the positioning of process equipment over the transport surface.
Figure 3:
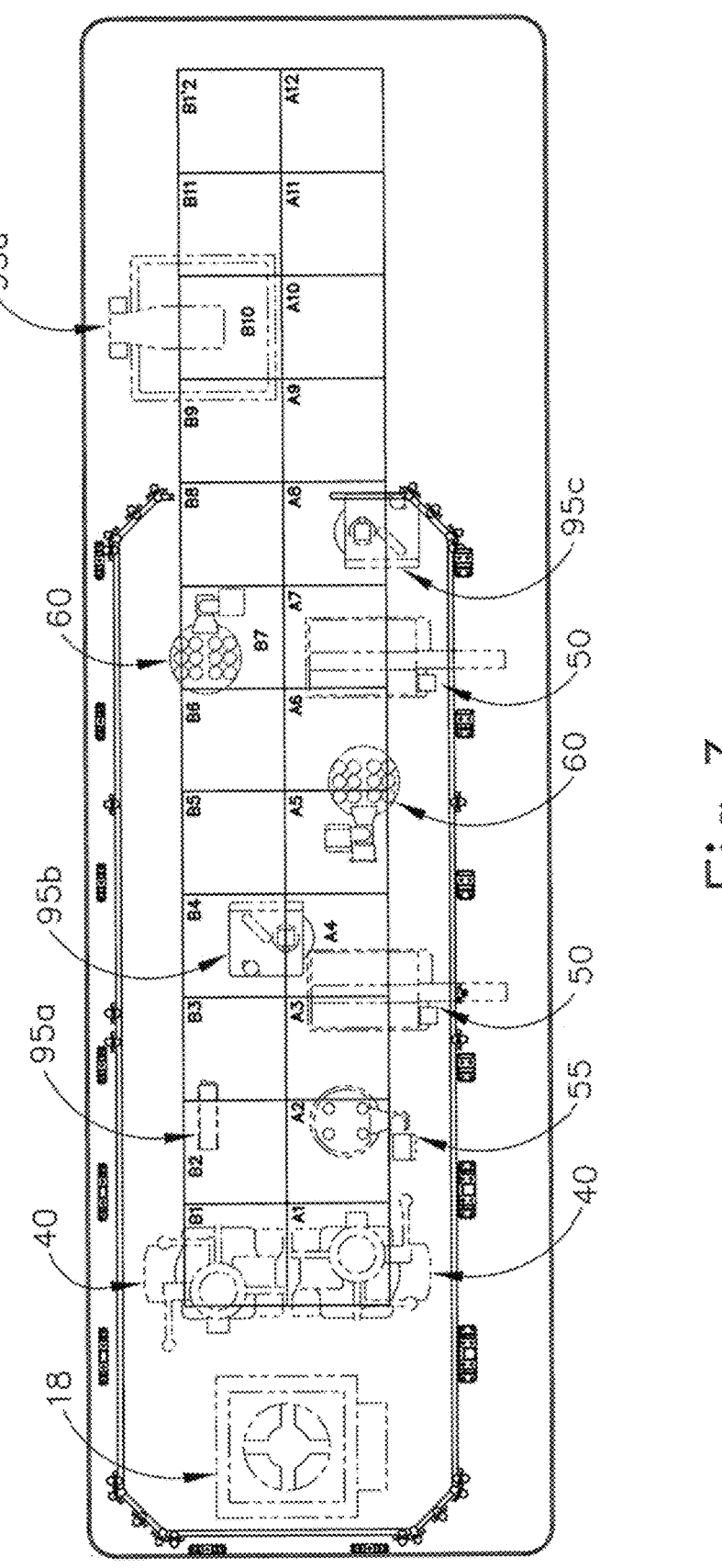
FIG. 3 illustrates a plan view of a transport surface of the omnidirectional magnetic movement apparatus showing individual tile segments and unit operation processing stations, between which a group of transport modules can be moved and positioned.

FIGS. 1 through 3 illustrate a process facility 10 that includes an omnidirectional magnetic movement apparatus 20, also referred to hereinafter as a process movement apparatus 20, integrated with one or more, and typically several, process unit operations. The process facility 10 includes a process platform 12 that contains or houses the omnidirectional magnetic movement apparatus 20, as well as electronic and electrical connections, and utility processes, for operation of the process facility including the process movement apparatus. The process facility 10 also includes a platform surface 13 that covers the process platform 12. A portion of the platform surface 13 includes a transport surface 16 that has the omnidirectional magnetic movement apparatus 20 there beneath.

The process movement apparatus 20 includes a magnetic movement stator 21 that includes a plurality of magnetic movement sub-units, or tile segments 22, each tile segment consisting of a stator or unitary group of stators enclosed within a housing. The tile segments 22 are joined edge-to-edge and integrated to form a matrix of tile segments, each tile segment being a square of about 9 inches (22 cm) square, and alternatively about 1 foot (30 cm) square. The integrated tile segments 22 can be oriented in a wide variety of formations. In the illustrated embodiment, the integrated tile segments are arranged two (2) tile segments wide by twelve (12) tile segments long. A platform surface 13 is placed over the top surfaces of the housings of the integrated tile segments 22, with the portions thereof positioned directly over the integrated tile segments providing the transport surface 16. The platform surface 13, and in particular the portion thereof over the integrated tile segments, is a thin, non-magnetic sheet, for example a non-magnetic stainless-steel plate. In the embodiment shown in FIG. 1, the platform surface 13 has a rectangular area of 4 feet wide and 13 feet long.

The transport surface 16 can have one or more processing stations, at and above which unit operation processing equipment can be positioned, and one or more inspection stations, at or above which an inspection device can be positioned. As described herein, the shuttles can be moved to a processing station and positioned and oriented beneath processing equipment, or can be moved to an inspection station and positioned and oriented beneath an inspection device.

<Shuttle>

A plurality of driven magnets (permanent magnets or electromagnets) is arranged within a plane on-board the planar body of a shuttle, and covered or encased by a stainless steel, durable plastic or similar continuous material. The magnet fields of the on-board driven magnets interact with the generated and controlled magnetic fields of the stator so that a drive force is exerted on the shuttle in the intended and instructed direction to move the shuttle along, and to move the shuttle per se above, the transport surface. The shuttle can move over the transport surface in the three positional rotations (pitch, roll and yaw) and through the three orthogonal movement directions, including the horizontal directions of x and y, and in a vertical direction z.

Thus, the plurality of drive coils of the stator and the plurality of driven magnets of the shuttle are arranged to enable movement of the shuttle in all six degrees of motion, providing for the simplest of movements to very complex movements of a shuttle with high precision.

The omnidirectional magnetic movement system can also include one or more sensors for sending a position of a shuttle. In some embodiments, using the real-time position of the shuttle, the movement controller can activate the one or more stator driving circuits to drive the actuation coil assembly to thereby interact with the one or more magnets of the shuttle to move the shuttle over the transport surface.

Each shuttle of the omnidirectional magnetic movement system is provided a unique shuttle identification code. A shuttle (magnetic mover) also comprises at least one shuttle identification device, while a stator comprises at least one stator identification device operable to interact with the at least one shuttle identification device to associate the unique shuttle identification code with that particular shuttle, and one or more sensors for sensing a position of a particular shuttle. The control system can continuously follow the position and the generated magnetic fields in the stator to transport, position, and orient the shuttle as instructed and desired.

Figures 4, 5, 6:
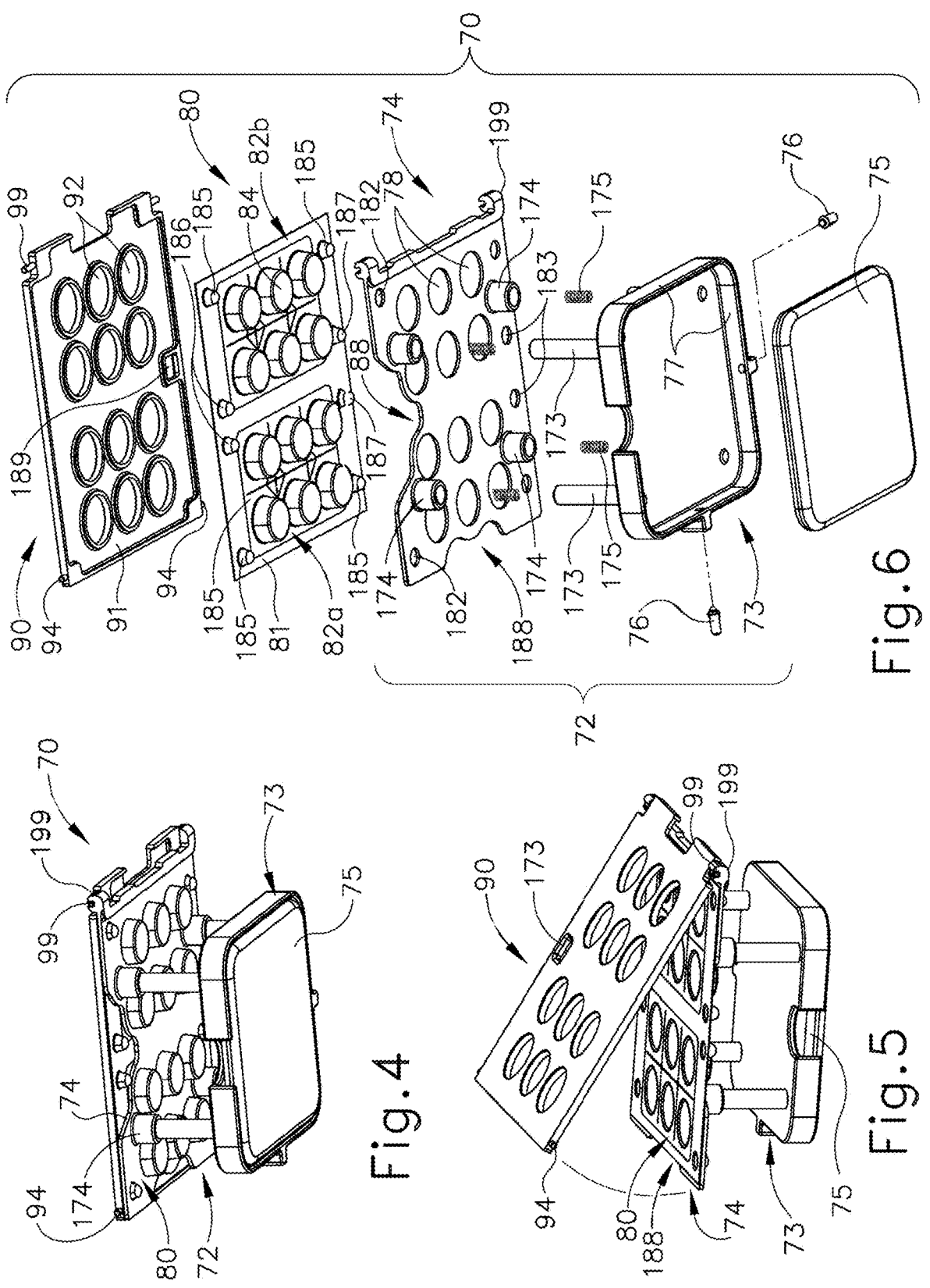
FIG. 4 illustrates a bottom perspective view of a fabrication module that includes a shuttle, a carrier, and a substrate.
FIG. 5 illustrates a top perspective view of the fabrication module of FIG. 4, and a mask that is positionable over the substrate.
FIG. 6 illustrates an exploded view of the elements of the fabrication module of FIG. 4.

The present invention provides for a process system and method to use an omnidirectional magnetic (process) movement apparatus as a means for transporting a substrate through a production process employing one or more, and preferably a plurality of, process unit operations. FIGS. 4 through 6 show a fabrication module 70 incorporating a shuttle for placement and movement of the fabrication modules over the transport surface 16 of the omnidirectional magnetic movement apparatus 20. The twenty-four tile segments 22 shown (segments A1-A12 and B1-B12) integrate into a unitary stator 21 that underlies and forms a unitary transport surface 16 portion of the platform surface 13.

A shuttle typically has a square planar shape (though other shapes could be made) with a peripheral edge, and has a cover of hard, durable plastic. Alternatively, the shuttle may have a continuous, seam-free stainless steel cover. The features of the shuttle allow for attachment to its upper surface or around its periphery a carrier that permits the shuttle to transport the carrier and any material or objects placed on the carrier.

In various embodiments, the system can include a sub-system and process performed for delivering a shuttle to a process movement apparatus, and associating said shuttle having a unique identification address with the process movement apparatus.

<Transport Modules and Fabrication Modules>

A transport module is a magnetically movable device that includes at least one shuttle and, in various embodiments, a carrier. The carrier is a structural device having a lower portion that is configured to attach to a surface of a shuttle in a predetermined orientation, and an upper portion that supports or has attached thereto a substrate. Typically, the carrier is fastened or secured to the shuttle. While a transport module can have a single shuttle, two or more shuttles can be combined as a unitary transport module. The structural device of the carrier can be any suitable construction material, such as a plastic, ceramic, metallic, or composite material thereof. The carrier interfaces a substrate with the at least one shuttle.

A fabrication module, as described herein, is the transport module having a substrate attached or secured to the carrier. A substrate can be any device or material upon which is placed or deposited a component material of an article, such as a solid, solid particulate, semi-solid or liquid, or an ingredient, component or reactant to a process or unit operation for making an article. An example of a fabrication module 70 is illustrated in FIGS. 4-6.

The movement and positioning of the fabrication modules by the process movement apparatus is important to the operation of the process unit operation equipment that will associate or interact with the fabrication modules. For example, after the fabrication module has been moved to, and positioned and oriented properly with, the construction material dispensing device, the movement controller can send an instruction to a process unit operations controller to inform or confirm that the particular fabrication module is properly positioned and oriented, with which the process unit operations controller can proceed with process unit operation and control of the unit operation device or apparatus. In some process unit operations, the process proceeds while the fabrication module is stationary in position and orientation, while in others, the process unit operation proceeds while the fabrication module is moving. In some embodiments, the fabrication module moves with movement of the shuttle in any one or a combination of the sixth degrees of freedom of motion; for example, in a horizontal (x,y) direction; in a vertical (z) direction, in a rotational motion through the vertical axis normal to the planar body of the shuttle, or a combination thereof. In some embodiments, the shuttle can oscillate either or both of the horizontal axes through the planar body of the shuttle, to effect an oscillating movement of the shuttle and a vibration at the same frequency of the fabrication module fixed thereto.

The tracking of movement and position of the fabrication modules by the process movement controller through the one or more unit operations shall enable sufficient control over the article fabrication process to allow for individual or multiple articles to be produced, on a personalized basis, for a single, unique customer or patient.

<Substrate>

A substrate is a device or formed material upon which is placed or deposited a component material of an article, or reactant to a process unit operation for making an article. Non-limiting examples of a component material is a solid, solid particulate, semi-solid, liquid or liquified gas component of an article being made on the process facility 10.

A substrate may be formed in an integrated substrate forming system and process, or more typically formed separate and away from the process system where the article or intermediate of an article is processed and formed. The formed substrate is then delivered to the omnidirectional magnetic movement system and/or containment system for further processing. The substrate forming system can include a substrate forming apparatus that forms a substrate from a stock material (for example, a thermoplastic film), a stock film supply apparatus for feeding the stock material to the substrate forming apparatus, and a loading system for positioning and placing the formed substrate onto a carrier of a transport module. The substrates can be formed on-demand when needed, or can be pre-formed in advance and stacked or grouped for use. In the latter embodiments, the process system can include a substrate staging area, and include a device for retrieving a stacked substrate using a combination of vertical-lifting arm and a de-stacking mechanism (to separate a single top substrate from the stack of substrates) for placing the unstacked substrate onto the transport module, and more specifically, onto the carrier of the transport module.

In some embodiments, a substrate can be a planar surface, and one or more articles can be formed onto an upper planar surface. In other embodiments, a substrate can be a container for one or more materials. In some embodiments, the container can be a molding form having one or more depressions, in which an article is made by process unit operations, and then released or ejected from the one or more depressions. In some embodiments, the depression(s) of the molding form have a shape of a tablet or other dosage form, non-limiting examples being cylindrical or oblong.

In one particular embodiment, and in various embodiments of processes for forming an article on a substrate using the process facility 12, a substrate is a blister card having one or more, and typically a plurality of, depressions arranged in an array, which provides both a molding form for the processing of the article and the packaging thereof.

A blister card can have any usable areal shape or dimension, and number of blister depressions as desired or needed. In various embodiments, a blister card with a single formation surface formed as a depression can be at least 1 centimeter (cm) and up to several centimeters in length and in width. A blister card typically has several, and up to dozens or more of, formation surfaces formed as depressions, and can be about 5 cm to 20 cm in each of the length and width dimensions. A stock roll of a blister card, which is typically separated into a plurality of individual blister cards, can have hundreds or thousands, or more, formation surfaces formed as depressions. In one non-limiting example, a blister card is about 10-15 cm in width to about 16-20 cm in length, and has from 2-40 formation surfaces formed as depressions. In one embodiment, the blister card is about 20 cm long and 13 cm wide, with 24 (6×4 layout) pre-formed depressions. In another embodiment, the blister card is about 13 cm long and 10 cm wide, with 12 (6×2 layout) pre-formed depressions. An example of a blister card 80 is illustrated in FIG. 6.

Non-limiting examples of substrate can include a blister tray and 3D-printed support structure having a planar structure and connecting members that connect detachably to a 3D-printed tablet, as described in US Patent Application Publication 2021/0205228, the disclosure of which is incorporated by reference in its entirety.

In some embodiments, a substrate forming system and process includes a marking system for marking (for example by printing) of a unique identification code, such as a lot number, digital address code, 2D barcode, DataMatrix or QR ("quick response") code, onto a substrate, including onto a formation surface of the substrate. The marking can be a visible marking, or an invisible marking that cannot be seen by the unaided eye, using a suitable visible or invisible ink. In various embodiments, the marking is formed on one or more surfaces of a substrate (for example, a top surface and bottom surface of the blister card), or on each of the formation surfaces (for example, a top surface of the base of the depression and/or a bottom surface or underside of the base of the depression of each blister depression). The marking can be detected and read by a scanner or imaging system, and the unique identification code communicated and entered into the controller of the process control system. The process control system associates the unique identification code of that physical substrate with the unique shuttle identification code of the specific shuttle that transports the fabrication module on which the physical substrate is carried. When a fabrication model carrying a substrate has been moved under control of the movement controller to a unit operation processing station, the process unit operations controller associates the substrate's unique identification code with the unit operation process and creates a record of the execution and completion of the unit operation process with the same substrate unique identification code. This control and recording process can be repeated at each unit operation processing station and inspection station employed in the making of the product.

In some embodiments, a substrate forming system and process can also include a substrate movement system that consists of an omnidirectional magnetic movement system that is dedicated to the substrate forming system. The substrate forming system, including the substrate forming apparatus, the stock film supply apparatus, and the loading system, are positioned over a transport surface of the substrate movement apparatus. A transport module (a shuttle with its carrier) can be positioned adjacent to the loading system for positioning and placing of a formed substrate onto the carrier to provide a fabrication module. A marking system can also be included to mark the formed substrate as described above. A scanning system can also be included to detect the identification codes of the respective marked substrate and the carrier of the transport module. The fabrication module can then move along the transport surface of the substrate movement apparatus under the control of a movement controller to an exit. In various embodiments, the substrate movement apparatus can be integrated with the process movement apparatus for seamless movement of the transport modules and fabrication modules there between.

<Substrate Mask>

A mask having one or more openings can be placed over an upper surface of a substrate, with the one or more openings in registry with the one or more formation surfaces of a substrate. In one embodiment, the mask is a sheet having a peripheral shape and dimensions that overlap or register with the periphery of a blister card substrate, and the mask sheet has a plurality of openings that register with the corresponding openings to the depressions of the blister card. In some embodiments, the mask sheet can have one or more openings of any regular, irregular, or geometric shape as desired or needed, including, by non-limiting example, circular, oval, and elliptical, that may be required to achieve functional performance or design aesthetics of the article. Conventional blister cards typically have circular depression and openings, so a typical mask will have a plurality of circular openings that register with a circular opening of the depressions.

In some embodiments, the mask can have one or more portions of the sheet removed, typically along an edge of the substrate (blister card), to form an opening or window that registers with a unique identification code printed on the substrate. This allows the unique identification code of the substrate to be exposed for scanning and/or imaging, to identify and register the specifically identified substrate with the processing system and the movement control system, for subsequent movement, tracking, and positioning of the blister card throughout the unit operations processing.

In various embodiments, the mask includes a means for releasably attaching to the upper surface or portion of the carrier, to inhibit or prevent movement or separation of the blister card from the carrier, and to cover the upper planar surface of the film of the blister card in the continuous areas that surround the depression(s), and block and prevent the depositing of construction materials and phase modifying liquids onto the upper planar surface of the film which will subsequently be contacted and sealed with a sealing film. An example of a mask 90 is illustrated in FIG. 6.

The fabrication module illustrated in FIGS. 4-6 includes a transport module consisting of a shuttle 75 that can be moved over the transporting surface by the stator, a carrier 72, and a substrate 80. The carrier 72 has a base 73 that has a planar cavity within which the shuttle 75 exactly fits. The base 73 is oriented onto the shuttle 75 with a pair of securements, shown as threaded screws 76 that pass through positioned holes 77 in adjacent sidewall of the base 73 and impinge against the sides of the shuttle 75. Four support posts 173 extend vertically from the four corners of the base 73. The carrier 72 also has an upper portion, called a nest 74, that has four support retainers 174 consisting of short hollow cylinders into which the upper ends of the four support posts 173 extend, forming the semi-rigid structure of the carrier, with a spring 175 in between each post 173 and support retainer 174. Spring(s) 175 is selected to provide flexibility, and some "give" when the nest 74 passes beneath equipment within the containment zone. One function of the spring(s) is to suspend the nest 74 above the posts 173 so that the top ends of the posts 173 maintain a clearance space with, and do not contact and dead-end into, the support retainer 174 of the nest 74.

The nest 74 has a plurality of openings 78 formed through its upper surface to register with and accommodate all of the depressions of the blister card. The substrate 80 is a dual-tray blister card having a first and second six-depression blister cards 82a and 82b within a blister frame 81. The blister frame 81 has a general retaining pin at each corner of blister frame 81, that register in any orientation of the blister frame 81 with corresponding general retaining slots 182 in the upper surface of the nest 74. The nest 74 and the blister frame 81 also have a means for positioning the blister frame 81 on the nest 74 in only one orientation. The blister frame includes a pair of close-spaced orientation pins 186 on the opposite longitudinal (or lateral) end, and a pair of far-spaced orientation pins 187 on one longitudinal (or lateral) end. The close-spaced orientation pins 186 of the blister frame 81 register and fit into only the close-spaced orientation slots 183 of the nest 74, and the far-spaced orientation pins 187 of the blister frame 81 register and fit into only the far-spaced orientation slots 184 of the nest 74.

A mask 90 is placed over the blister frame 81 to protect the un-formed film portions of the blister cards 82 (the film portions that surround the depressions) from contact with and soiling by construction material and processing materials. Over-spraying of printing liquid outside of the depression and onto the un-formed film portions can interfere with proper securement of a sealing film over the formed dosage forms of a blister card. As shown in FIGS. 5 and 6, the mask 90 has a planar frame 91 having a plurality of circular openings 92 that correspond to and register with the openings into the plurality of depressions 84 of the blister cards 82a, 82b when oriented with the nest 74. The mask includes a pair of lifting pins 94 extending from the opposite sides of the frame 91 at a front end of the mask, and a hinging member, illustrated as a pair of hinge pins 99 extending from the opposite sides of the frame 91 at a rear end of the mask, to engage with a pair of hinging members at the opposite sides of the frame 91 at a rear end of the nest 74, illustrated as a pair of clamps 99 having a slot to receive respectively the pair of hinge pins 99 to form a pair of hinges, which allows the front end of the mask 90 to pivot upward and away from the nest 74.

The nest 74 also has a front edge having a recess 188 that has an undercut pattern at the front end of a blister card 80 so that a user's fingers or other implement can be placed in registry with the recess to raise the front end of the blister card when removing the blister card 80 from the nest 74. A similar recess 88 is formed into a side edge of the nest 74 that has an undercut pattern at the side edge of a blister card 80 so that a user's fingers or other implement can be placed in registry with the recess to raise the front end of the blister card when removing the blister card 80 from the nest 74.

<Module Movement>

Each independent transport or fabrication module can be moved independently of other transport or fabrication modules, and can be moved in different directions and patterns than other transport or fabrication modules. Transport or fabrication modules can move over the transport surface at speeds up to 2 m/sec, and typically between 0.1 to 0.75 m/sec, and can accelerate up to 5 m/sec$^2$.

The movement of a shuttle can be configured to operate under the control of the movement controller with a substrate fixed to the carrier and with the carrier secured to the shuttle. Once a substrate is detached from the carrier, the shuttle can move automatically under the control of the movement controller to a staging area remote from the dosage forming system.

The shuttle is typically magnetically levitated above the transport surface to an elevation of up to about 4 mm, more typically up to about 3.5 mm, and can be controlled at an elevation of about 0.1-3.5 mm. More specifically, the planar undersurface of the shuttle is elevated above, and parallel to, the planar transport surface. After a fabrication module is positioned and oriented at a process station, elevation of the shuttle vertically enables raising the substrate, affixed to the carrier transported by a shuttle, into contact with, or a closer non-contacting position with, a unit operation equipment or apparatus, to provide improved processing accuracy and efficiency, and reduced loss of powder or droplet material into the airspace of the containment zone.

Each shuttle can include a plurality of movement signalers that communicate with one or more of a plurality of static detectors within the stator, for communicating the position and orientation of the shuttle at any moment, and the movement of the shuttle across the transport surface. The precision resolution is typically about 0.2 mm or less, including about 0.02 or less, and for example, about 5 microns, and the refreshed interval (or delay) of less than 100 msec.

Each independent fabrication module can be independently moved to and positioned at a processing station or an inspection station of the process platform 12, in order to correspondingly position and/or orient a substrate and the one or more formation surfaces thereof, beneath or relative to a processing equipment or an inspection device, respectively.

<Containment System>

The process system can include a containment system. The containment system provides a containment zone comprising, and typically consisting, of a volumetric airspace boundaried by and between the upper surface of the transport surface of the stator, and a containment housing. The containment housing includes one or more transport openings and one or more sealable openings.

A transport opening can include an opening or port through a sidewall of the containment housing that extends from the transport surface into the sidewall to provide entry and/or egress for a fabrication module into and out of the containment zone. The lateral dimensions and height dimensions of the transport opening are sufficient for the need, and are typically sized to allow one or more shuttles (including the respective substrate and an article formed thereon) to pass simultaneously through the transport opening. A transport opening can also be used to provide an inlet for airflow to pass into the containment zone from the outside. The inflow of air over and through the fabrication module as it exits can enhance removal of loose particulate. In some embodiments, a closure can be placed temporarily and sealed over a transport opening, and can be hingedly connected or removable.

A sealable opening can include an opening or port through a ceiling panel or a sidewall of the containment housing, which is typically sealed during operation of the process system or sub-process system. A unit operation processing equipment is positioned within one of the sealable openings in the containment housing for processing a unit operation within the containment zone. Typically the sealable openings have a similar or uniform size. The unit operation processing equipment typically has a processing portion that extends vertically into the containment zone, and an external portion that extends outside the containment zone, which can be accessed or controlled from outside the containment housing. The processing portion that extends within the containment zone can be an element for dispensing a compound or process material, such as a powder dosing port or a liquid nozzle, a texturing element for tamping or manipulating the constructions material or phase-modified material, and an implement such as a probe element for contacting with the construction material or the substrate to maneuver or move the construction material and/or a phase modified or processed material. Each unit operation processing equipment can be fitted with a seal adapter plate, if necessary, having an inner seal portion attached sealably to the processing equipment, and an outer seal portion positionable sealably within the sealable opening, for example, with conventional or quick-disconnect fasteners.

The containment housing can also have one or more airflow openings to allow air, for example conditioned air or ambient air, from outside to pass through the containment housing and into the containment zone, optionally including a closure for sealing off the air opening when desired. Airflow openings can be placed at various positions along the containment housing to allow better control of where and how much air is drawn into the containment housing.

Figure 7A:
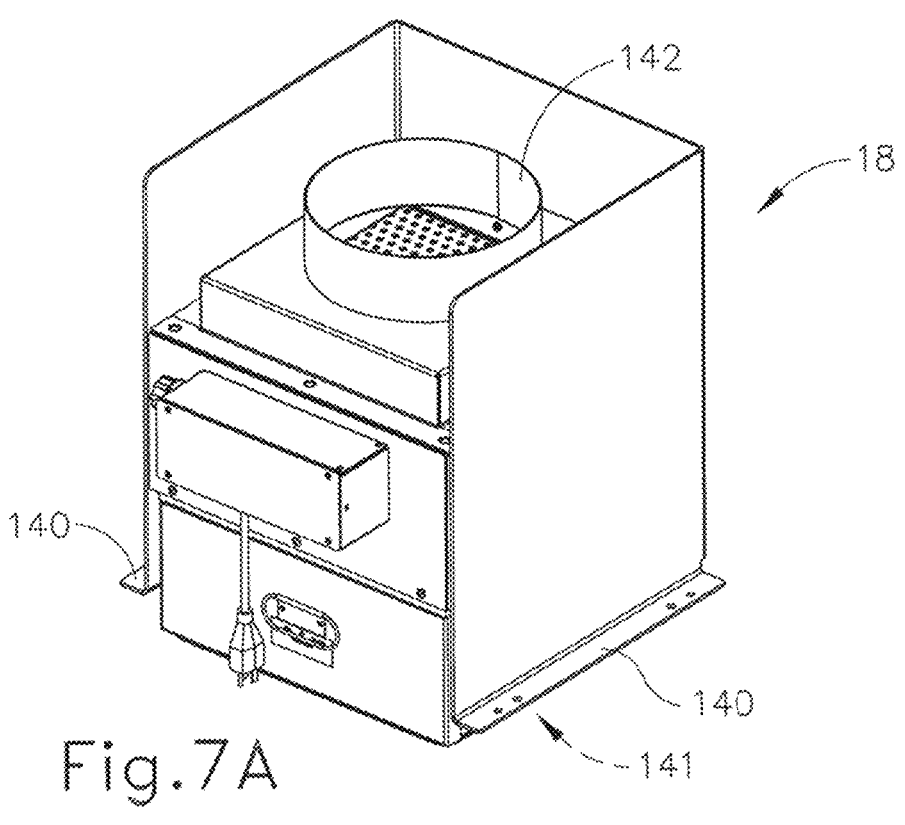
FIGS. 7A and 7B illustrate an air handling and filtration apparatus that provides air handling and air-borne particle and droplet separation.
Figure 7B:
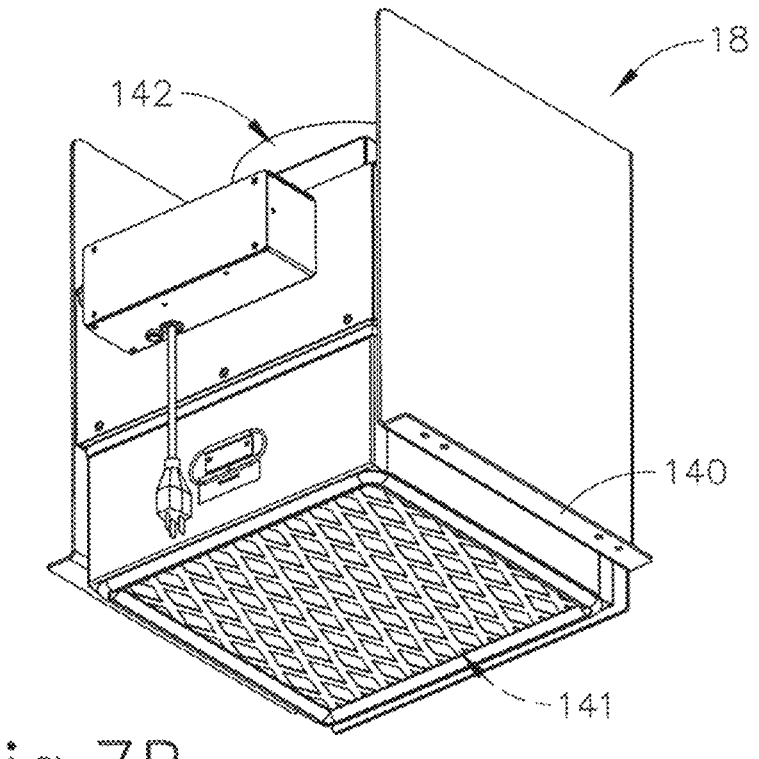

The containment system also includes an air handling and filtration apparatus, for example, a high efficiency particulate air (HEPA) filter apparatus that provides air handling and air-borne particle and droplet separation. An example of a commercially-available HEPA filter apparatus 18 is shown in FIGS. 7A and 7B. One of the sealable openings 34 can be configured for installation of the HEPA filter that includes supports 140 for mounting to the ceiling panel 33 of the containment housing, an air-inlet port 141 disposed within the containment housing, a particulate separation means (for example, a filter and/or cyclone separator) and an air exhaust port. The HEPA filter apparatus 18 is configured to pull a flow of outside air, and typically a predetermined and/or continuous flow of outside air, into the containment zone, and into and through the particulate collection apparatus, to ensure that a construction or process material, including drug or active particulate and droplets, cannot leave the containment zone and escape into the outside environment. Air within the containment zone, which may contain airborne particles and/or droplets, is drawn into the air-inlet port 141 by an air blower of the HEPA filter apparatus, filtered to separate and isolate the particles and/or droplets, and expelled as filtered air to atmosphere. Outside air is drawn into the containment housing through the transport opening 36, and flows along or through containment zone past the areas of the process unit operations and equipment (for example, a powder-material depositing device and/or a phase modification device).

In various embodiment, the containment system, including the design of the containment housing and the HEPA filter system, is configured to maintain at all times a negative air pressure within the containment housing relative to the environment outside the containment housing. This ensures that any exchange of air will be from outside the containment housing to inside the containment housing, and that any air passing from inside the containment housing to the outside will pass through the HEPA filter apparatus.

An example of a containment system is shown in FIG. 2. Containment housing 30 includes a plurality of fixed panels, typically transparent panels, and optionally a support frame.

The plurality of panels includes one or more upper ceiling panels 33, and a plurality of sidewall panels, typically a series of sidewall panels including first sidewall panel 31 and second sidewall panel 32 on opposite sides of the containment housing 30, that provide a peripheral boundary. A transport opening 36 in the periphery boundary is disposed at a forward end of the containment housing 30. The transport opening 36 extends from the transport surface 16 to the ceiling panel 33, and is boundaried by opposed panels 35. The transport opening 36 provides both an entryway and egress for the movement of fabrication modules into and out of the containment zone, as described herein, as well as an inlet for airflow.

The ceiling panel 33 and sidewall panels 31, 32, 35 are typically transparent or translucent, preferably transparent, to enable viewing of the movement of the fabrication modules at and between the processing stations from outside the containment system, and can be constructed of sheets of a transparent polymer material, such as polycarbonate (Lexan®), acrylic (Plexiglas®), tempered glass, sapphire, or polyvinylchloride (PVC), of sufficient thickness to provide stability and support. A framework for the ceiling panels and sidewall panels can be made by conventional framing construction and of a conventional framing material, a non-limiting example of which is aluminum or a thermoplastic. In some embodiments, the framework provides rigidity and support for the ceiling and sidewall panels. In various embodiments, equipment supports to supporting the process unit operation equipment over the transport surface 16 and above the containment housing 30 can include lateral equipment supports 15 that span the width of the containment housing, elevated with support brackets 14.

In various embodiments, the containment housing is configured to minimize the number of equipment devices within its airspace, and to minimize the exposure of the components of equipment devices within its airspace. Minimizing the exposure of the components of equipment devices within its airspace also aids in reducing the airflow velocity, by reducing the obstacles that the airflow must flow around, which can cause the airflow to increase in velocity when passing around the obstacle.

In various embodiments, the containment housing is designed to provide a containment zone of the smallest volume, sufficient to perform some or all of the process unit operations upon the construction material deposited and/or phase modified upon or within a substrate.

In various embodiments, the vertical height of the containment housing is minimized to a height sufficient to move the substrate and its deposition surface over the transport surface, and beneath the components of the apparatuses performing the series of process unit operations. The process unit operation equipment communicates with the fabrication modules through the ceiling panels and/or the sidewall panels of the containment housing, to transfer or deposit construction material and/or perform phase modification operations. For example, each of the powder deposition equipment and the binding liquid dispenser can deposit corresponding powder and binder liquid amounts thorough the discharge nozzle, printhead, or ports extending through the ceiling and/or sidewall panels of the contaminant housing.

In various embodiments, only the portions or components of the unit operation equipment necessary for performing the process unit operations extend vertically through an upper (ceiling) panel of the containment housing, and into its volume, thereby minimizing or limiting contact of air-borne particulate to the remaining portions or components of the unit operation equipment. By way of example, a powder deposition apparatus that deposits a construction material, such as a bindable powder material, onto an upper deposition surface of a substrate, such as into the depressions of a blister sheet, is configured to extend only the outlet or deposition ports at the lower end of the equipment through the ceiling panel of the containment housing, and into its volume. By minimizing the vertical height of the containment housing, and its volume, less mass or volume of air is required for efficient and effective collection and withdrawal of airborne particles and droplets from within the containment zone.

The containment housing openings and the positioning of the process unit operation equipment within the containment housing are designed, positioned and oriented to avoid excessive containment airflow velocity, particularly horizontal airflow velocity, which can affect the efficacy of the unit operations being performed by the equipment upon the articles being formed on the substrates.

In some embodiments, the lateral airflow velocity within the containment housing can be up to 10 m/sec. A minimum air flow velocity into the air inlet opening is controlled to at least 0.5 m/sec to ensure that particulate within the containment zone cannot migrate or escape out of the containment zone via the opening. In various embodiments, the design of the containment system and the positioning of the process unit operation equipment provides an average airflow through the containment system of less than 5 m/sec, more typically less than 2 m/sec, in the airspaces immediately surrounding and adjacent to the unit operation process, and in particular, the powder deposition equipment, and the binding liquid printing system.

For example, in the depositing of a particular construction material onto a substrate, air can flow horizontally between the deposition device (for example, a powder deposition equipment) and the substrate on which the construction material (for example, the dosed powder) is being deposited, or in the phase modification of the construction material by a phase modification device (for example, the depositing of a binding liquid onto a dosed powder disposed on the substrate), air can flow horizontally between the liquid dispensing nozzles and the powder material disposed onto the substrate. Excessive airflow through the containment system, and directed between the unit process equipment and the substrate can affect the precision and accuracy of placement of a powder onto the substrate, and/or a liquid onto the powder and/or the substrate.

In particular, errors in the accuracy of placement of the dispensed liquid from printing nozzles can be affected by the linear velocity at which the transport module carries the substrate (and the article being formed thereon) beneath stationary printing nozzles. In general, a linear airflow velocity of 1.0 meters per second (m/s) or less, and preferably 0.6 m/s or less, is used to minimize errors in liquid droplet position and phase modification quality. Droplet placement accuracy can also be improved by reducing the clearance distance between the printing nozzle plate and the substrate, and/or by increasing the droplet velocity, to minimize the liquid droplet flight time. The clearance distance between the printing nozzle plate and the substrate, for example, a blister card or a protective mask covering a blister card as described herein, is less than 1 cm, and more typically about 8 mm or less, or 6 mm or less, for example, about 5-8 mm, and is incrementally and/or infinitely controllable by the movement controller.

In some embodiments, to prevent or limit the interference of the airflow upon the depositing of powder material onto the substrate, and the printing of binding liquid onto the layer of powder material, a barrier such as one or more baffles, interior walls, or air curtain can be installed around the printing nozzle or equipment and/or the powder deposition equipment to reduce or prevent airflow and air vortices across the surface of the substrate and between the surface of the substrate and the process equipment.

In various embodiments, the ratio of the vertical height (or the average vertical height) of the containment housing to the area of the containment zone (typically determined by the peripheral sidewalls of the containment housing) is between 0.1-100 cm height per square meter (cm/m$^2$), more typically 0.5-20 cm/m$^2$, and even more typically 5.0 to 10.0 cm/m$^2$. In one non-limiting example, a containment housing covers an area of 20 square feet (about 1.8 m$^2$) and has an interior height of about 12.5 cm, providing a ratio of about 7 cm/m$^2$.

In other embodiments, the ratio of the vertical height (or the average vertical height) to the width (shorter lateral dimension) of the containment zone is between 0.5-20 cm/m, more typically 2-10 cm/m, and even more typically 4 to 8 cm/m. The height of the containment housing, from the transport surface of the stator to the ceiling panel, is preferably less than 50 cm, more preferably less than 15 cm.

Within the volumetric space of the containment housing are the fabrication modules that are levitated above the transport surface of the stator and "float" through the airspace within the containment housing. Typically the height of the carrier and the substrate while moving and operating within the containment housing is less than the height of the containment system in the space of operation. In a typical arrangement, the bottom of a shuttle of a fabrication module rides about 1-5 mm, for example, about 1.5-3.5 mm, above the transport surface of the stator. The shuttle is typically 1-2 cm in thickness. The carrier, which is fixed to and transported by the shuttle, can have a vertical height at least 1 cm, and preferably at least 5 cm, and up to about 20 cm, and preferably about 10 cm from the top surface of the shuttle. In some circumstances, a carrier can have a greater vertical height, provided that it operates with sufficient headspace when within a containment housing. To optimize the amount of airflow needed for air-borne particle control, the vertical height of a containment housing can be minimized, and is typically about 20-30 cm in height, preferably about 15 cm or less, and for example about 10 cm or less.

<Process Unit Operations>

The present invention also provides that one or more process unit operations can be performed interactively with the omnidirectional magnetic movement system that includes an omnidirectional magnetic movement apparatus, a shuttle, a carrier associated with a shuttle, and a substrate. The one or more process unit operations can be a coordinated plurality of unit operations.

Each process unit operation is positioned in the vicinity and typically directly above a corresponding unit operation station that consists of an area of the process movement apparatus designated for positioning and orientation of a fabrication module, for conducting the unit operation process at or onto prescribed one or more formation surfaces of the substrate. Under the control of the movement controller, each fabrication module can be positioned and oriented precisely so that each fabrication surface of the fabrication module is positioned beneath a processing apparatus in order to initiate a predetermined process operation. In some embodiments, the predetermined process operation can be performed while the fabrication module, and the one or more formation surfaces thereon, are fixed and stationary in position on the process movement apparatus; for example, a stationary position and/or orientation for stationary processing while levitated above the transport surface. Alternatively, the same fixed and stationary fabrication module can be lowered onto the physical platform surface (non-levitating) while performing a process operation. In another embodiment, the predetermined process operation can be performed while the fabrication module is moved horizontally under the control of the movement controller along the upper surface of the transport surface within the unit operation station while a process operation is performed; for example, a changing position and/or orientation for dynamic processing while levitated above the transport surface.

Figure 8A:
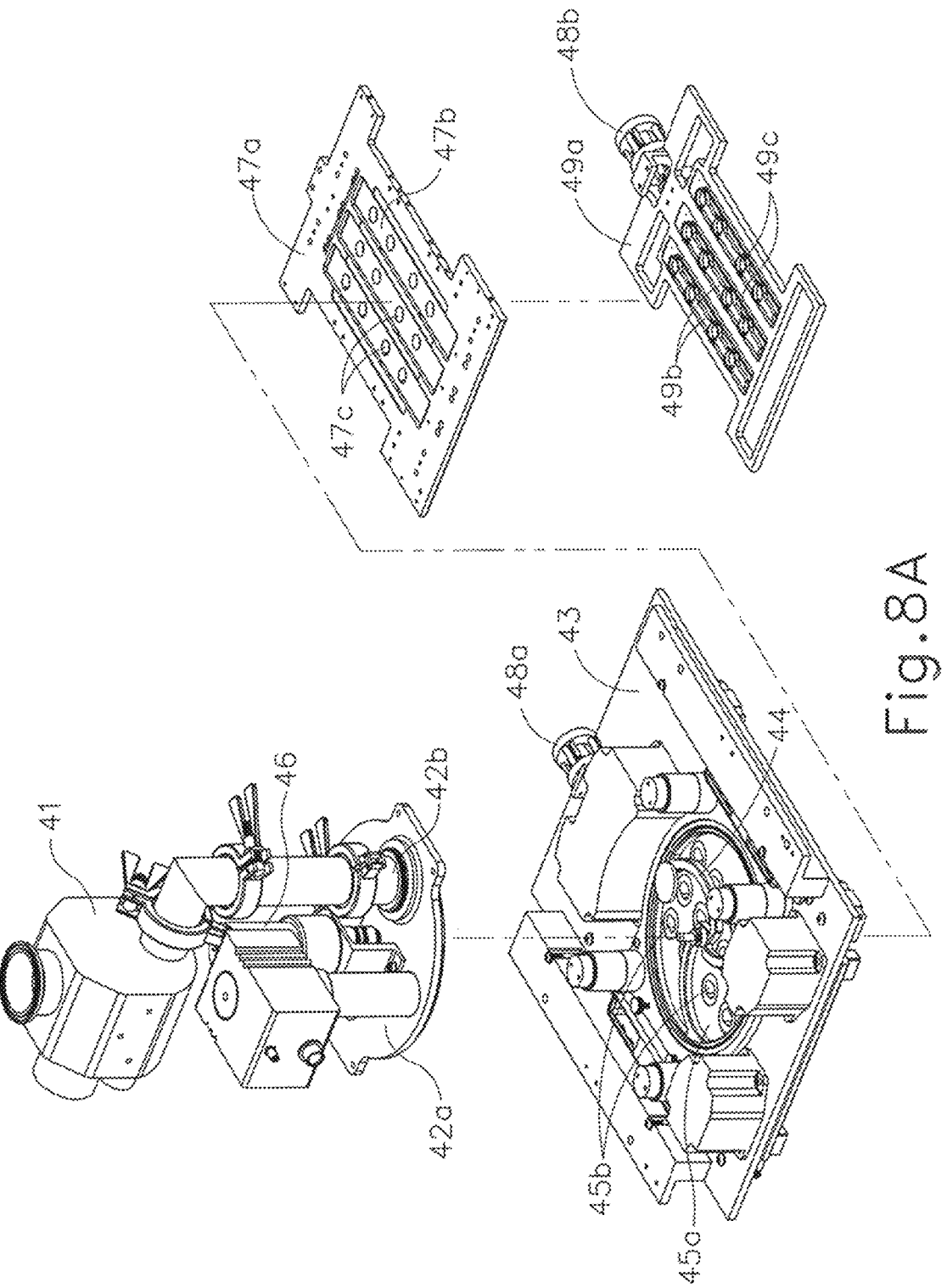
FIG. 8A illustrates a top perspective view of a powder dosing apparatus for dispensing a powder material to individual formation surfaces of a substrate.
Figure 8B:
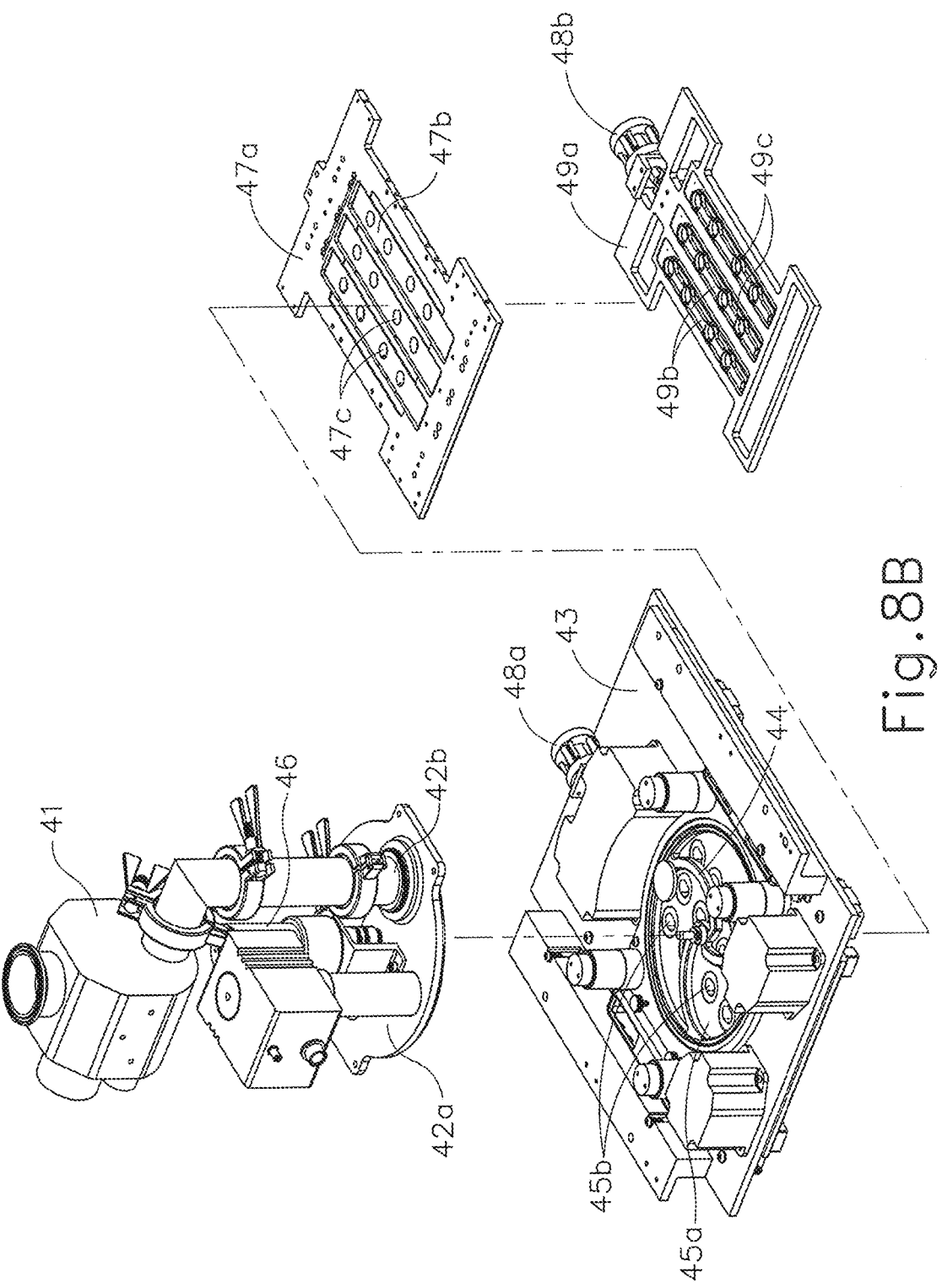
FIG. 8B illustrates an exploded view of the elements of the powder dosing apparatus of FIG. 8A.

For example, at a powder dosing (unit operation) station, the levitated fabrication module and its one or more formation surfaces (such as a blister card and its depressions) can be positioned and oriented (in the x,y plane) with the depressions positioned directly beneath and coaxial with the discharge ports of a powder dosing apparatus, and the blister card surface is spaced a minimal vertical clearance distance beneath the discharge ports of a powder dosator, within a range of up to 10 mm, for example, about 6 mm. With the fabrication module fixed and levitated in position, the powder dosator can deposit from each of the discharge ports a dose of a powder material down and into the corresponding depressions of the blister card substrate. The minimum vertical clearance minimizes the vertical drop distance of the powder dose, and therefore the risk of forming dust clouds and splashing of the powder outside the depression(s). An example of a powder dosing apparatus is shown in FIGS. 8A and 8B.

In another example, at a powder leveling (unit operation) station, the fabrication module, its one or more formation surfaces, and a dose of powdered construction material (such as, the blister card and its depressions containing a dose pile of powder material) can be positioned and oriented (in the x,y plane) beneath a powder leveling apparatus. With the fabrication module fixed and grounded upon the transport surface (not levitated), one or more vibration probes of a vibratory leveling apparatus are lowered until a distal end contacts an upper surface of the fabrication module and/or substrate (such as, the blister film web between adjacent depressions), and an energy wave (for example, an acoustic wave) of a predetermined frequency and amplitude are passed axially from the distal ends of the probes onto and into the substrate, which causes the dose pile of powder material to disperse and spread within the cavity of the depression(s) to reduce the unevenness of the surface of the powder material and form a powder layer with a more planar surface.

In another example, at a liquid printing (unit operation) station, the levitated fabrication module, its one or more formation surfaces, and a construction material therein (such as, the blister card and its depressions containing a layer of powder material), can be first positioned and oriented (in the x,y plane) so that the formation surfaces are disposed outside of the target line of one or more rows of printing nozzles. Each printing nozzle selectively and independently dispenses a printing liquid at a predetermined volumetric rate within a unit target area below said nozzle. The levitated fabrication module is then passed beneath the printing nozzles and into and through the target line of the one or more rows of printing nozzles, while respective printing nozzles independently dispense a curtain of the printing liquid onto the powder material layer, but not on the area of the substrate outside the powder layer, in a predetermined printing pattern, under the control of the processing controller.

A process unit operation can include, and not in any particular sequence or priority delivery and association of a shuttle to an omnidirectional magnetic movement apparatus; delivery, association and orientation of a carrier with a shuttle; formation of a substrate from a stock material, including the formation of the formation surfaces such as wells, cavities, penetrations, protrusions or other geometric modifications, onto which a construction material may be deposited; delivery, association and orientation of a substrate with a carrier; delivering and dispensing a construction material to a substrate, which can include a powder or particulate material and a liquid material; leveling of a powder or particulate construction material upon a substrate; delivering and dispensing of a processing material to a substrate for phase modification of or processing of a construction material; sanitization or sterilization of substrates or their stock material, construction materials, processing or phase modification liquids, and articles and intermediates thereof, using electromagnetic spectrum emissions or chemical reactants; surface modification of an article or intermediate thereof formed from a construction material, for example, removing excess solidified materials, including by subtractive manufacturing methods; electromagnetic (EM) irradiation; thermal phase change; evaporation and drying; sanitizing; article and processing inspection and quality control; article marking and identification; unloading of completed articles from a substrate; and post-formation handling and packaging of an article-containing substrate to form an integral primary package unit.

The use described herein of an omnidirectional movement system for moving a plurality of fabrication module between two, and typically more, unit operation stations, allows for asymmetrical processing of intermediate and finish products to provide either capability or advantages that are impractical if not impossible using conventional processing systems. In one example, an asynchronous movement of numerous fabrication modules allows each fabrication module to dwell at a particular unit operation station for as long as needed to execute the unit operation process, without interfering with the other fabrication modules to move to other unit operation stations.

In another example, the ability to adjust the position, orientation and movements of each fabrication module independently allows for adjustments in the unit operation processing of a particular fabrication module completely independent of other fabrication modules. In one non-limiting example, the passing of a substrate under a liquid spraying unit operation to wet a layer of powder material disposed within one or more depressions of the substrate can be altered with each successive passing, by changing the orientation of the fabrication module so that the dispersing of liquid is applied onto a successive layer of powder at a different angle (for example, at 90 degrees or transverse) than that applied to the previous powder layer, which conventional conveying systems are not known to do or be capable of doing.

In another example, an inspection system can include one or more inspection devices to detect deficiencies or errors in an intermediate or finished product on a specific fabrication module, or even a specific at a specific fabrication position on a specific fabrication module, and can instruct the specific fabrication module to move back to one of the unit operation stations for further processing to correct the deficiency or error, on a priority basis, even interrupting temporarily that unit operation process scheduled to be performed on other fabrication modules. This can be particular important where a series of fabrication modules are being processed as a specific and unique batch, and the required further processing would, with a conventional production system, require inserting the specific fabrication module into the queue of a conveying system ahead of the unit operation process, ahead of other fabrication modules in the queue, and then extracting the same fabrication module from the conveying system after the unit operation, to return the same to its batch mates.

<Construction Material>

A construction material can include any liquid, liquified gas, semi-solid, or solid material that can be formed, transformed, reacted upon, mixed or combined into an article. A construction material can be an ingredient, including one of two or more ingredients of an article. A construction material can also be a (solid, semi-solid, or liquid) intermediate or unfinished article (for example, a tablet body) that is pre-formed and further processed within the process system to form a finished article or product. A solid construction material can be a powder comprising one or more particulate compounds or compositions. Non-limiting examples of a form of the powder can be amorphous or crystalline fine particles, granules, pulverulent, agglomerates, coated (shell and core) particles, and nuggets.

A liquid construction material can be a free-flowing liquid or a viscous or gel material, including materials containing suspensions or dispersions of a solid particle or particulate. Non-limiting examples of the liquid construction material are aqueous and non-aqueous liquids, organic and inorganic liquids, creams, lotions, pastes, gels, and monomer compounds.

A construction material can be one or more construction materials, and can be a single compound or composition, or two or more distinct and separate compounds or compositions, as well as blends or mixtures of two or more compounds and/or compositions.

In some embodiments, a material or a component of the material (for example, one or more component compounds of a composition) can be a construction material, as well as an element or component of a phase modification system. In a non-limiting example, a binding liquid for a base powder can comprise a binding material and solvent (by non-limiting example, water or an alcohol such as ethanol or isopropanol), wherein the binding material and a portion of the water or other solvent can become component compounds of the resulting bound-powder dosage form, as well as components of the phase modification system for the base powder which is bound together both by the binding material and the wetting of the base powder to form a bound-powder matrix of the dosage form.

In various embodiments, a construction material can comprise an active agent, and by non-limiting example, an API, in either a powder or particulate form, or in a liquid form.

A construction material or a component thereof or a component of a processing material can be a functional ingredient of the resulting article. Non-limiting examples of functional ingredients, for example in a tablet or medicament, can include fillers, diluents, binders, suspension agents, viscosity agents, polymers including release positioning polymers or release modifying polymers, coatings, flavorants, disintegrants, sweeteners, preservatives, colorants, lubricant and glidants. Non-limiting examples of the compounds or components of such ingredients can include inorganic salts, acidic compounds, organic compounds such as sugars and sugar alcohols, modified starches and starches, cellulose ethers and esters, microcrystalline cellulose, carboxymethyl cellulose, croscarmellose Na, glycols such as polyethylene glycol and propylene glycol, povidone, mineral hydrocarbons, and oleochemicals such as fatty alcohols, mineral stearates, glycerol, and lipids.

In various embodiments, a construction material or its component elements can be changed into a different form by a mechanical process (by non-limiting example, by compression, pulverization, or by dissolving or suspension into a second liquid material) and/or can be transformed into a different physical state or phase (for example by heating or cooling a material that results in evaporation, or by sublimation, solidification, freezing, melting, spray drying, spray congealing, or condensation), and/or into a different chemical structure, for example by chemical reaction with another compound, or by irradiation, curing, or polymerizing. Any one or more of these process unit operations can require the use of a process equipment integrated into the process system, including into the omnidirectional magnetic movement system and controller, the containment system, and the process unit operations controller.

In some embodiments, the powder material comprises a thermoformable powder that when exposed to heat and elevated temperature softens and/or melts, and when cooled, solidifies the build material. Non-limiting examples of a thermoformable powder material, and processes, equipment and systems for making dosage forms, are described in US Patent 2009/0060983 (Bunick et. al), U.S. Pat. No. 6,258, 381 (Luber et. al), U.S. Pat. No. 8,313,768 (Kriksunov et. al), U.S. Pat. No. 9,511,028 (Chen et al), U.S. Pat. No. 10,493,026 (Koll et. al) and WO 2018/096363 (UCL Business PLC), the disclosures of which are incorporated by reference in their entireties. A thermoformable powder material comprising the thermoformable compound or material can be deposited within a depression and leveled into a single layer with uniform thickness. Typically, a leveling step comprises moving the powder material deposited within a depression to form a layer of the powder material having an even or flat upper surface. The variation in the height of the upper surface is less than 20% of the diameter of the depression, more preferably less than 10%, or less than 5%, and even more preferably than 2%. After the layer of powder material is formed, it is exposed to a phase modification system to form a solidified porous or non-porous solid article, for example a dosage form. The phase modification system can comprise a thermal heating by conduction, convection or radiation, using an electromagnetic (EM) spectrum system as described below. The thermoformable materials within the powder material soften and partially melt to adhere to other particulate of the powder material. After cooling, the adhered thermoformable material solidifies and bonds the particulate of the powder material together to form a bound powder material.

In other embodiments, a thermoformable powder can be deposited, leveled and thermoformed as described above, two or more times within a depression to form a multi-layer article. Each of the layers of thermoformable powder can have the same composition and ingredients, optionally including an active, or different compositions that optionally include an active.

<Dispensing of Construction Material>

In various embodiments, the construction material is supplied to and stored at the process system, and in particular, to the omnidirectional magnetic movement system and/or containment system, by conventional means, including pumps, conveyors, tanks, and bins, depending on its form (for example, a liquid or a solid). The construction material can be dispensed or deposited onto a substrate of the fabrication module by well-known means, depending on the chemical type of construction material and its condition.

Typical kinds of equipment for dispensing or depositing construction material, or for dispensing or depositing a material used in a phase modification system. Powder construction materials can be stored in tanks or other containers in bulk, and can be delivered to the process system by air conveying or gravity feed through a fixed or flexible piping, tubing or hose. Equipment for dispensing or depositing powders and other pulverulent materials can include iris valves, rotary valves, butterfly valves, augers, screw conveyors, belt conveyors, tubular drag conveyors (for example, US Patent Application Publication 2022-0184891 to Hewlett-Packard Development Corporation, L.P., the disclosure of which is incorporated by reference in its entirety), and powder dosators. In various embodiments, the equipment for supplying and dispensing of depositing powder materials can include modular containers of the powder material, including feedback-controlled instantaneous and continuous mixing systems, which enable easy and rapid changing of the supply of a powder material to the process equipment.

Liquid forms of construction materials, as described herein earlier can be stored in tanks or other containers in bulk, and can be delivered to the process system by gravity feed, pumps, hydraulic and pneumatic pressure, and through a fixed or flexible piping, tubing or hose.

In various embodiments, a construction material dispensing module can include a probe for continuous and/or intermittent sampling of a construction material to measure, record and report the compositional uniformity of the construction material. The controller system can include a process that incorporates intelligent data processing algorithms, including artificial intelligence (AI) where appropriate, to analyze and assess if a phase modification dispensing process is in control or not, and to implement corrective action or other control.

<Powder Dosator>

In some embodiments, the construction material dispensing equipment is a powder dosator, for delivering a predetermined mass or volume or "dose" of a flowable powder material to one deposition site or to multiple deposition sites of a substrate. The substrate can be a blister card, and the one or multiple deposition sites can be the one or more depressions formed into the blister card. The powder dosator delivers the predetermined mass (or volume) of the flowable powder material into one, more, or all of the depressions in the blister card. In various embodiments, a predetermined mass of the powder material deposited into any one depression can be about 1 mg or less, or at least about 1 mg, preferably from about 15 mg to about 375 mg, and up to about 5 gm. Non-limiting examples of a dosator are described in PCT Publications WO 2020/081561 and WO 2021/21189, the disclosures of which are incorporated by reference in their entireties.

In various embodiments, the dosator deposits, or is configured to deposit, a consistent volume of the powder material. The consistent depositing of a uniform volume of powder material preferably delivers a powder material at a uniform volumetric density, to achieve a uniform, repeatable mass dosage.

In various embodiments, a plurality of doses of a powder material are dispensed simultaneously and separately onto a corresponding plurality of deposition surfaces, and in particular, a plurality of depressions. Ideally, the respective volumetric amounts of the deposited powder material in all the plurality of depressions would be identical, or at least having a statistically narrow variance; for example, a variance of about 3% or less, including about 2% or less, or 1% or less. Under the presumption that the mass density of the powder filling each of the depressions is constant and the same, then the mass dosage of powder deposited into every depression would be the same or within a statistically narrow variance.

In various embodiments, the dosator system can include an integrated near infrared (NIR) spectra sensor. NIR spectroscopy uses light transmission and absorption to measure various constituents in a sample material, such as moisture, starch, protein, fat and oils. NIR can be used to detect these specific elements, understand the concentration of the elements and/or to detect changes in the overall composition. Because NIR penetrates deeper into bulk material than mid-infrared, it provides better, more reliable measurement on a production line. In one embodiment, the NIR sensor can emit electromagnetic waves in a range of, but not limited to, 780-2500 nanometers. The NIR light waves illuminate the surface of the powder material passing through a passageway within the dosator assembly.

The NIR sensor may be used, but not limited, to detect and monitor the uniformity of one or more compounds, including one or more active drugs and pharmaceutical ingredients, blended into a batch with other excipient powders, to detect variation in the quantity of the compound within the powder material, and correspondingly, to detect a variation of the compound in a volume of powder material being dosed onto the substrate surface or depression. The detection and monitoring allow programming of the process system to terminate or modify the processing in the event that the concentration of the compound, such as one or more active drugs and pharmaceutical ingredients, is detected to be too high or too low, and outside a target acceptable range.

In other embodiments, the dosator deposits, or is configured to deposit, an invariant or statistically-narrow variant mass of the powder material. Various means for controlling the mass of the powder material can be employed. In various embodiments, a weight scale (loadcell) can be disposed under the bulk powder hopper or an intermediate bulk powder feeder to measure or monitor the weight of powder dispensed onto the substrate. In some embodiments, a weight scale can be disposed within the carrier or under the substrate to detect an absolute or differential mass amount of powder material dosed into a particular formation surface (depression) or onto the entire substrate (blister card). In some embodiments, a controlled weight scale that ensures a consistent mass of the powder material is prepared for depositing into a particular depression.

In various embodiments, the dosator device provides an assembly of components that delivers a predetermined dose amount of the powder material onto (or into) one, or more, or all the deposition surfaces of the substrate. When multiple dosator devices are deployed in parallel each independent dosator device may be assembled with components that delivers a different predetermined dose amount of the powder material onto (or into) one, or more, or all the deposition surfaces of the substrate and the combination of these one or more dosator devices provides greater and nearly infinite control over the amount of powder material dosed onto (or into) one, or more, or all the deposition surfaces of the substrate.

The undersurface of the deposition portion of the dosator is positioned to provide a clearance above the substrate of not more than 1 cm, preferably not more than 6 mm, and more preferably not more than 3 mm.

Typically powder typically has a bulk density of 0.2 to 1.5 $gm/cm^3$, more typically 0.4 to 1.0 $gm/cm^3$, which can be determined by well-known methods.

Typical deposition of powder from a supply bin can include a means for assisting or maintaining powder flow and maintaining consistent powder density from the supply bin through a discharge port. A non-limiting example of such means is a volumetric feeder, such as a metering screw feeder. Another non-limiting example of such means is a vibrating device, which should be isolated from the supply bin. Additionally, a powder stirrer and or spreader can be utilized and include a roller, a blade, or another type of material spreading and stirring device.

In various embodiments, a powder flow aid can be used to improve the processibility of a powder material when used at mass levels of about 0.05 to 5%. Examples of powder flow aids are fumed silicas, stearates, tricalcium phosphate, calcium silicates, aluminum oxide, magnesium oxide, and zinc oxide. By way of example, fumed silica is supplied by Degussa AG with the trademark AEROSILR).

FIGS. 8A and 8B illustrate a non-limiting example of a volumetric powder dosing apparatus, or powder dosator 40, configured for depositing equal volumes of powder material into each of the depressions of a blister tray, with minimal deviation. Build powder material from a supply container (not shown) feeds into a metering screw feeder 41 to connected to respective connection ports 42*b* of a feed base 42*a*. The feed base 42*a* is secured to frame 43 having a cylindrical cavity. A circular distribution plate 44 is positioned rotatably within the cylindrical cavity, and has a plurality of openings extending to its periphery, to distribute powder into the dose fill cavities below. Positioned directly beneath the distribution plate 44 is a stock plate 45*a* having a plurality of conical stock ports 45*b* for holding a volume of material. The number of conical ports 45*b* is selected and configured into an array to register with the fabrication surfaces of a substrate, for example, the depressions of a blister card. Electrical drive 46 effects rotation of the distribution plate within the cavity of the frame. Mounted beneath frame 43 is an upper dose fill frame 47*a* and a lower dose discharge frame 49*a*. The upper dose fill frame 47*a* has three dose fill plates 47*b* arranged in parallel, each having a row of precisely machined and formed dose fill cavities 47*c*. The upper dose fill frame 47*a* is driven by drive 48*a* between a fill position in which the dose fill cavities 47*c* register and align with the stock ports 45*b* of the stock plate 45*a*, to fill dose fill cavities 47*c* with powder, and a dispense position.

The lower dose discharge frame 49*a* has three dose dispensing plates 49*b* arranged in parallel and aligned with the three dose fill plates 47*b* of the upper dose fill frame 47*a*. Each dose dispensing plate 49*b* has a row of dispensing ports 49*c*. The lower dose discharge frame 49*a* is driven by drive 48*b* between a fill position in which the dose dispensing plates 49*b* block the bottom openings of the dose fill cavities 47*c* of upper dose fill frame 47*a*, and a dispense position in which the dispensing ports 49*c* axially align with the dose fill cavities 47*c*, to dispense the powder from the dose fill cavities 47*c* into the depressions of the blister card.

<Leveling>

Leveling is a process unit operation of moving the particles of a mass or dose of construction material, deposited into a pile onto or within a depression of a substrate, into a layer of the powder that is more level, and preferably a layer of powder with a flat surface. In some embodiments, the layer of powder provides a construction material layer with an upper planar surface. Subsequent processing of the leveled construction material layer by a phase modification process forms a solidified, unitary layer of the construction material.

In some embodiments, the construction material can be a powder, particulate or pulverulent material, and the subsequent phase modification process forms a unitary bound-powder matrix having the upper planar surface.

In various embodiments, leveling can be accomplished using the movement of the fabrication module, either by vibration or pitching of the shuttle around an axis through the shuttle, or by lateral acceleration of the shuttle over and along the transport surface. Under the control of the movement controller of the omnidirectional magnetic movement apparatus, the movement stator can be actuated to cause a fabrication module, through the magnetic forces on the shuttle, to oscillate and/or vibrate the shuttle at a frequency and magnitude to form the deposited powder into a layer of powder having a substantially uniform thickness and substantially even, level upper surface within the depression. In some embodiments, a cycle of oscillations or vibrations can move the body of the shuttle in rotation about a vertical axis through the shuttle, and/or angular or pitch motion through a horizontal axis or line through the shuttle. The cycle time needed to effect leveling of the powder dose is less than 10 seconds; for example, and typically, less than 5 seconds, or 2 seconds or less, and more typically 1 second or less.

In various embodiments, leveling of a dose of powder on or within a cavity of a substrate can be accomplished at a separate processing station that includes a means for vibrating the substrate, for example a blister card having a plurality of depressions, to effect leveling of a dose amount of a loose powder dispensed therein. In some embodiments, a powder leveling apparatus vibrates the blister card with an amplitude and frequency to transforming a pile of powder dispensed into a cavity of a blister card into a layer of the powder with a level, or more level, upper surface, and more preferably a flat surface. A non-limiting example of a vibration leveling apparatus uses voice coil actuators to generate vibrations that are passed onto the blister card to effect a movement of a powder material disposed with the depressions.

Figures 9A, 9B:
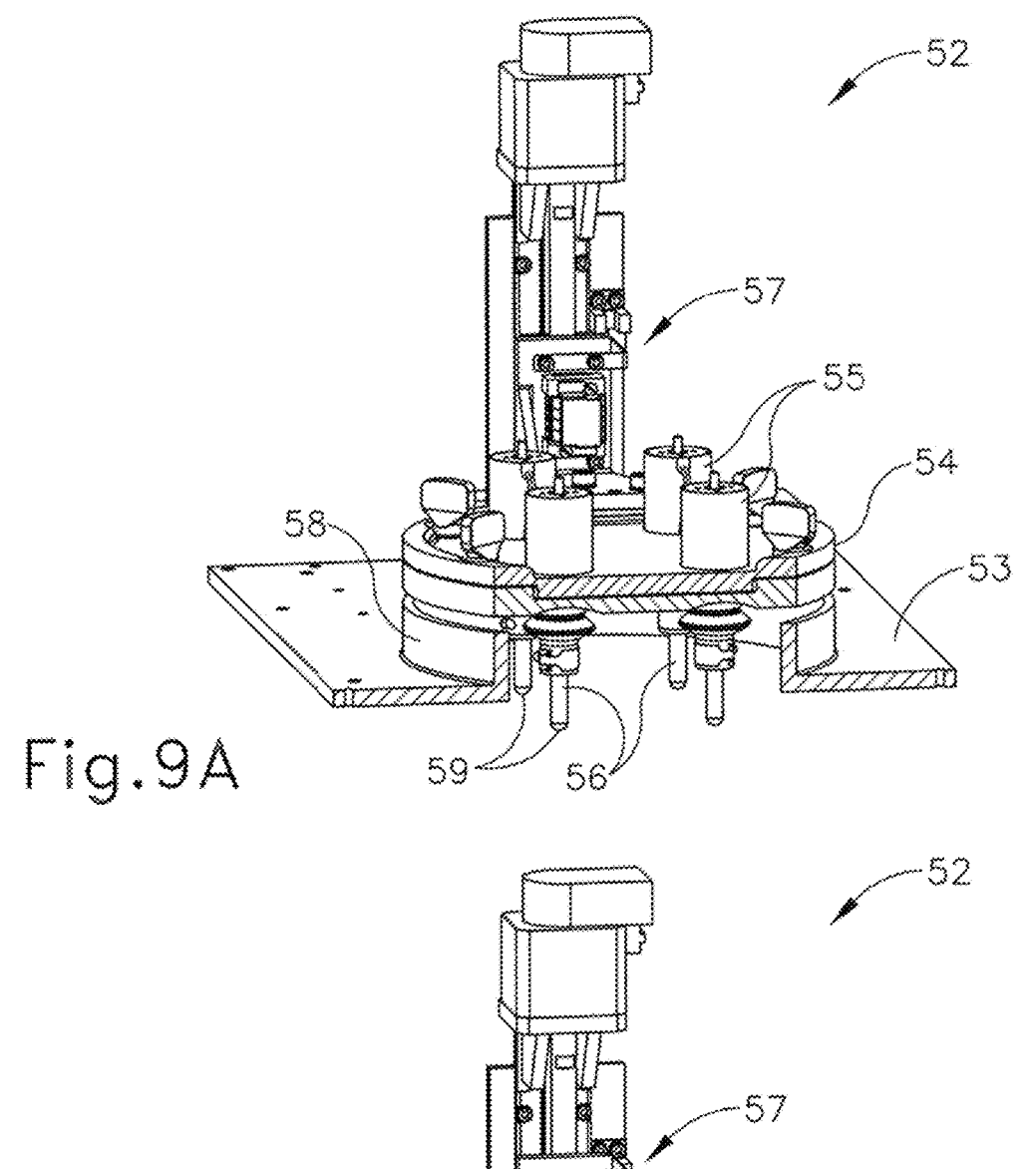
FIG. 9A illustrates a partial cut-away of a perspective view of a powder leveling apparatus, positioned in a raised position.
FIG. 9B illustrates the powder leveling apparatus of FIG. 9A positioned in a lowered position.

FIGS. 9A and 9B illustrate a vibration leveling apparatus 52 useful for leveling a powder material on or within a substrate, such as the depressions of a blister card, by passing vibrations onto the blister card to effect a movement of a powder material disposed with the depressions. The vibration leveling apparatus 52 includes a base 53, and an activator manifold 54, that support positioned voice coil actuators (VCA) 55. Each actuator 55 includes an elongated, rigid probe 56 that extends axially beneath the actuator and reciprocates axially when actuated by the VCA. The rigid probe 56 has a tipping made of a resilient material that transmits the vibrations of the probe 56 into the substrate. The base 53 is configured for sealable attachment to and easy removal from the ceiling panels 33 of the containment housing. The vibration leveling apparatus 52 includes a lift mechanism 57 attached rigidly to the activator manifold 54 that vertically lowers and raises the activator manifold 54. In the raised position shown in FIG. 9A, the distal ends of the probes 56 are raised up into collar 58 of the base 53, which protects the probes 56 when installing and removing the vibration leveling apparatus 52 from the containment housing, and also avoids the probes from extending into the containment zone. In the lowered position shown in FIG. 9B, the activator manifold 54 is lowered so that the distal ends of the probes 56 are lowered to extend below the ceiling 33 and into the containment zone. In the lowered position, the distal ends of the probes contact the upper surface of a fabrication module 70 (shown in FIG. 4) that has been positioned and oriented beneath the vibration leveling apparatus 52, and more specifically contact the substrate 80 (blister card(s)), or alternatively the mask 90 positioned over the substrate or any other part of the nest that is in direct contact with the substrate. In various embodiments, two or more VCAs are positioned in the activator manifold 54 so that the distal ends of the probes 56 contact the upper surface of the substrate at symmetrical locations on the top surface of the substrate or mask. After the probes have contacted the substrate (or mask) the VCA is activated to transmit vibrations to into the body substrate. In some embodiments, a VCA transmits a vibration in a frequency range from about 1-100 Hz at an amplitude powered at 1-10 volts, for example, 40 Hz with a 1-volt amplitude. Vibration of the substrate, for example a blister card, or the mask contacting the upper surface of the substrate, vibrates the powder material within the depression into a layer of powder having a uniform thickness and an even, level upper surface within the depression. The operation takes less than a second, and typically 0.1 second or less.

In various embodiments, the spring(s) are selected to provide a spring constant k that supports the weight of the nest 74, the substrate 80 (for example, blister card 82) and any construction material (for example, build powder and binder liquid), and the mask 90, with a natural frequency of vibration that matches or estimates the vibration frequency transmitted by the VCA.

In various embodiments, then the fabrication module has been positioned at the leveling station, the movement controller will cause the shuttle element of the fabrication module to descend and settle onto the process surface 16, and remain there while the vibration leveling apparatus lowers the probes and during the leveling process. After the actuation of VCA and the leveling process has been completed, the vibration leveling apparatus lifts the probes and returns to the raised position, and the fabrication module is raised off the process surface 16 and moves out of the leveling station under the control of the movement controller.

In various embodiments, the leveling means can be employed simultaneously with depositing the dosage amount of the powdered construction material.

Non-limiting examples of devices for level of volume of powder material within the depressions of a blister tray can be found in PCT Publications WO 2020/081561 and WO 2021/211898, the disclosures of which are incorporated by reference in their entireties.

<Liquid Dispensing>

Equipment for dispensing or dispersing of liquids including aqueous and non-aqueous liquids, organic and inorganic liquids, solutions, suspensions, creams, lotions, pastes, gels, and monomer compounds can include pumps (including piston pumps, gear pumps, positive-displacement pumps, peristaltic pumps, and progressive cavity pumps), gravity fed dispensing valves, spray nozzles (including single fluid, dual fluid, ultrasonic atomizers, and printing nozzles. The type of equipment used for a liquid can be selected based on the type, dosing amount, and properties of the liquid, including temperature, density, viscosity, vapor pressure, and surface tension. The equipment can deliver construction material to a substrate to form a single article (for example a single dosage form) or to form multiple articles, sequentially or simultaneously.

Liquid construction materials can be stored in tanks or other containers in bulk, and can be delivered to the process system by pumping or gravity feed through a fixed or flexible piping, tubing or hose. In some embodiments, a construction liquid or other processing liquid can be stored in a modular container. The modular container has an interior space to hold a volume of liquid, and includes a filling port for loading the volume of liquid into the interior space, and a dispensing port for discharging liquid from the interior space. The discharge port typically includes a quick-connecting feature, such as a bayonet type connector and a sealing element that mate with a corresponding receiving port of a liquid dispensing equipment, so that a spent or empty liquid container can be quickly replaced, or a different liquid material exchanged.

Liquids can contain an active agent or compound. In some embodiments, the liquid is an aqueous liquid containing an API. In some embodiments, the active-containing liquid is dispensed on powder construction material in a process of phase modifying the powder into a solid form. In some embodiments, the active-containing liquid is dispensed onto an intermediate or unfinished article (for example, a tablet body) that is further processed, for example, by drying off volatile components of the liquid, leaving the API to form a finished article or product.

<Liquid Spraying and Printing>

Aqueous liquids and solvents can be dispersed by a liquid printing apparatus as a multiplicity of streams or droplets, either to dispense the liquid onto a substrate or to apply the liquid onto a mass or layer of a powder material, generally by a nozzle. Non-limiting examples of a nozzle for forming a stream or droplets of a liquid can include a single or dual fluid nozzle, an ultrasonic atomizer, a thermal inkjet nozzle, and a piezoelectric inkjet nozzle. Large droplets can be dispensed by a nozzle in the order of milliliters and micro-liters. A printhead or printhead nozzle can dispense a liquid in droplet sizes in the volume order of microliter, nanoliter or picoliter droplets. A person of skill can select a printhead or printhead nozzle based on the dosing amount of the liquid, the process parameters including temperature and pressure, and the properties of the liquid including density, viscosity, vapor pressure and surface tension.

Figure 10:
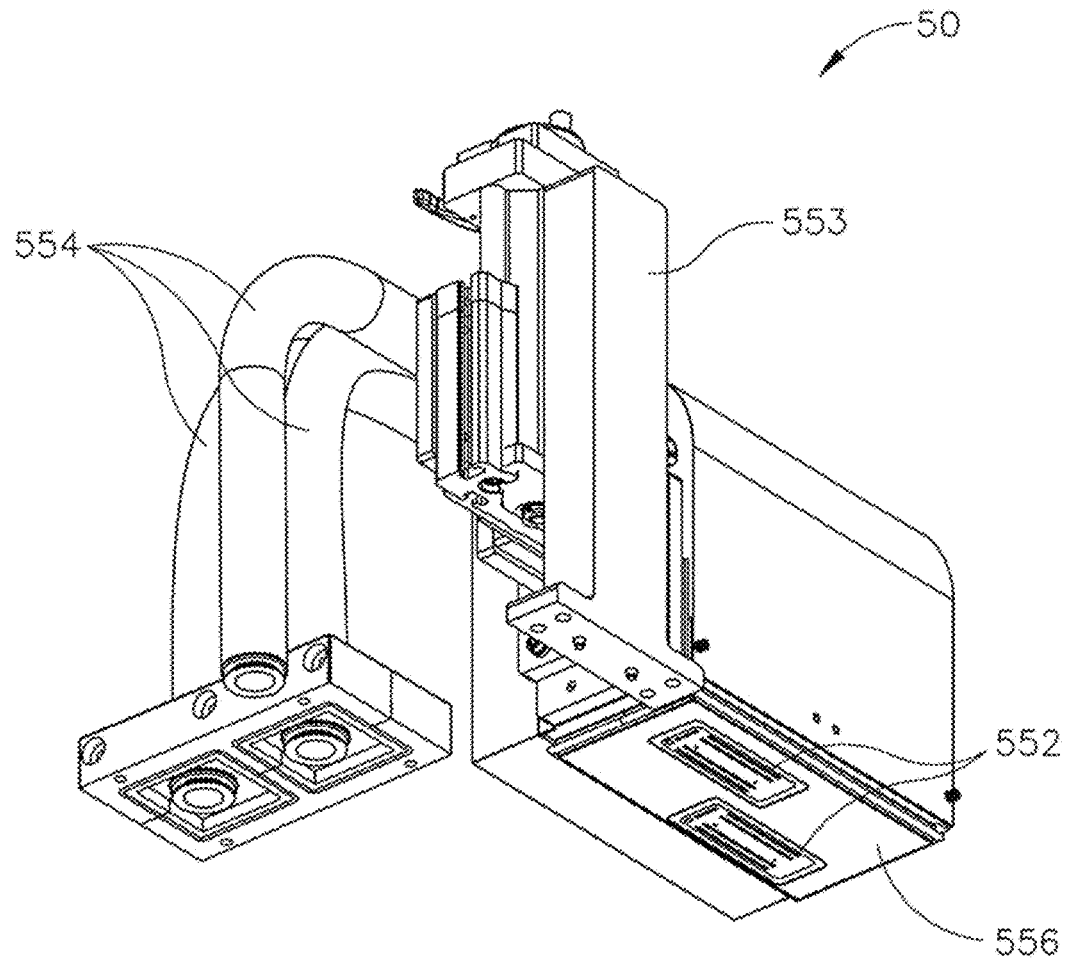
FIG. 10 illustrates a bottom perspective view of a liquid printing apparatus.

An example of a liquid printing apparatus is shown in FIGS. 10A and 10B. The liquid printing apparatus 50 includes a printer housing 551, a pair of printer nozzles 552 mounted on the bottom surface 556 of the printer housing 551. Each printer nozzle 552 consists of an elongated series of nozzle ports. The pair of printer nozzles 552 are positioned in parallel, staggered axially, and offset laterally, with the last nozzle port on one end of one nozzle 552 overlapping axially with at least one nozzle port on the other end of the other nozzle 552. The printing apparatus 50 also includes a support frame 553 and a lift mechanism 555 for vertically raising and lowering the housing 551 between a lowered position at which the bottom surface 556 and the printer nozzles 552 extend below the ceiling panel 33 of the containment housing 30 and into the containment zone, and a raised position in which the housing 551 and the bottom surface 556 are raised up above the containment housing 30 for accessing and removing the printer housing 551 from the containment housing.

Other non-limiting examples of printheads or printhead nozzles are described in U.S. Pat. Nos. 4,825,227, 4,875, 619, 4,883,219, 4,937,598, 5,659,346, 5,757,391, 5,781,212, 9,217,700, 9,381,154, 10,562,059, 10,850,236, 10,889,133, and 10,933,636, and US Patent Application Publication 2012/0092416, the disclosures of which are incorporated by reference in their entireties.

In some embodiment, a pattern of dispensed liquid onto a substrate or a mass of a powder material can be formed by dispensing liquid from selected jetting ports of a stationary nozzle to emit one or more curtains of dispensed liquid aligned in the plane of the print nozzle, and advancing the substrate or mass of powder material beneath the one or more curtains of dispensed liquid. The velocity of the advancing substrate and the selection of jetting ports for droplet emitting are controlled to emit droplets only from jetting ports directly above a lateral strip of the substrate or mass of powder material to be wetted. This process is well known in the art.

In some embodiments, an article can be a drug dosage form, wherein the construction material comprises a powder material, and the phase modification system can include a binding liquid printing system and a wetted powder material drying system.

In printing of a liquid onto either a deposition surface of a substrate, or a layer of powder or other construction material, the resolution and accuracy of the deposition of the print liquid is improved by limiting the path of flight of the liquid from the nozzle to the upper surface of the powder layer, the diameter or size of the liquid droplets, and the linear velocity of the expressed liquid droplets. Preferably, the substrate is controlled to a minimum clearance beneath the print nozzles of less than 2.5 cm (1 inch) or less, more typically less than 1 cm.

Non-limiting examples of a binding liquid that can be dispensed onto a layer of powder or other construction material are well known and are described in PCT Publications WO 2020/081561 (Aprecia Pharmaceuticals LLC) and WO 2021/211898 (Aprecia Pharmaceuticals LLC), the disclosures of which are incorporated by reference in their entireties.

<Auxiliary Active Agent>

In any of the embodiments described herein above, the system can further include a device, apparatus, or sub-system for storing, delivering, and/or depositing an auxiliary active agent, such as an API or medicament, onto a construction material or phase-modified construction material. An auxiliary active agent can be either a particulate material, or other solid material, or a liquid material or in a liquid form along with one or more solvents. In various embodiments, a quantity by mass or volume of an auxiliary active agent can be deposited onto a construction material (for example, an ingestible powder material) or onto a phase-modified construction material. An example of a device, apparatus, or sub-system for storing, delivering, and/or depositing an auxiliary active agent, such as an API or medicament, onto a construction material or phase-modified construction material is described in U.S. Pat. Nos. 8,252,234 and 8,101, 244 (both SmithKline Beecham Corporation), the disclosures of which are incorporated by reference in their entireties.

<Surface Modification>

In various embodiments, a process unit operation can provide surface modification of an article or an intermediate article. In various embodiments, a surface finishing apparatus can include a surface finishing body with a bottom finishing surface. The finishing surface is configured to extend a bottom finishing surface onto a powder layer, or a wetted powder layer within a depression, to alter or modify the surface roughness of one of the powder layers or wetted powder layers. In some embodiments, the finishing surface provides a consistent contour and texture to the top surface of the intermediate article and/or finished article. In some embodiments, the contour of the top surface can be rounded or slightly domed. The finishing surface can also provide a means for removing particles of a powder material that adheres to an upper portion of the depression sidewall. In some embodiments, the powder of the powder layer can be a dry, as-deposited or leveled layer of powder, while in other embodiments, the powder of the powder layer can be a wetted or partially wetted layer of powder.

In some embodiments, the finishing surface contacts the powder layer at portions elevated above a profile of the finishing surface, to reduce the elevated portions of the powder layer. The finishing surface is lowered in elevation until the profiled surface of the finishing surface contacts the entire upper surface of the powder layer, to form the upper surface of the powder layer a surface profile matching that of the finishing surface. In various embodiments, the finishing surface is lowered beyond the upper surface of the powder layer, to compress or compact the powder material within the powder layer. In various embodiments, the material of the surface finishing body, which forms the finishing surface, is a solid material made of a metallic or alloy, or a solid thermoplastic material. In preferred embodiments, the material of the surface finishing body resists or prevents adherence of either wetted or dry particles of the wetted or dry powder material. In various embodiments, the surface finishing body and the finishing surface can extend into the depth of a depression. Non-limited examples of solid thermoplastic material include, without limitation, polyethylene, and in particular ultra-high molecular weight polyethylene (UHMWPE, or just UHMW), nylon, and polypropylene.

In various embodiments, the surface finishing body can also be rotated around an axis of the surface finishing body and the finishing surface, and rotated through an arc or oscillated, or rotated at a rate, to promote the smoothness of the surface of the powder layer. In some embodiments, the surface finishing body can be rotated in one rotational direction, or in both rotational directions.

Figures 11A, 11B:
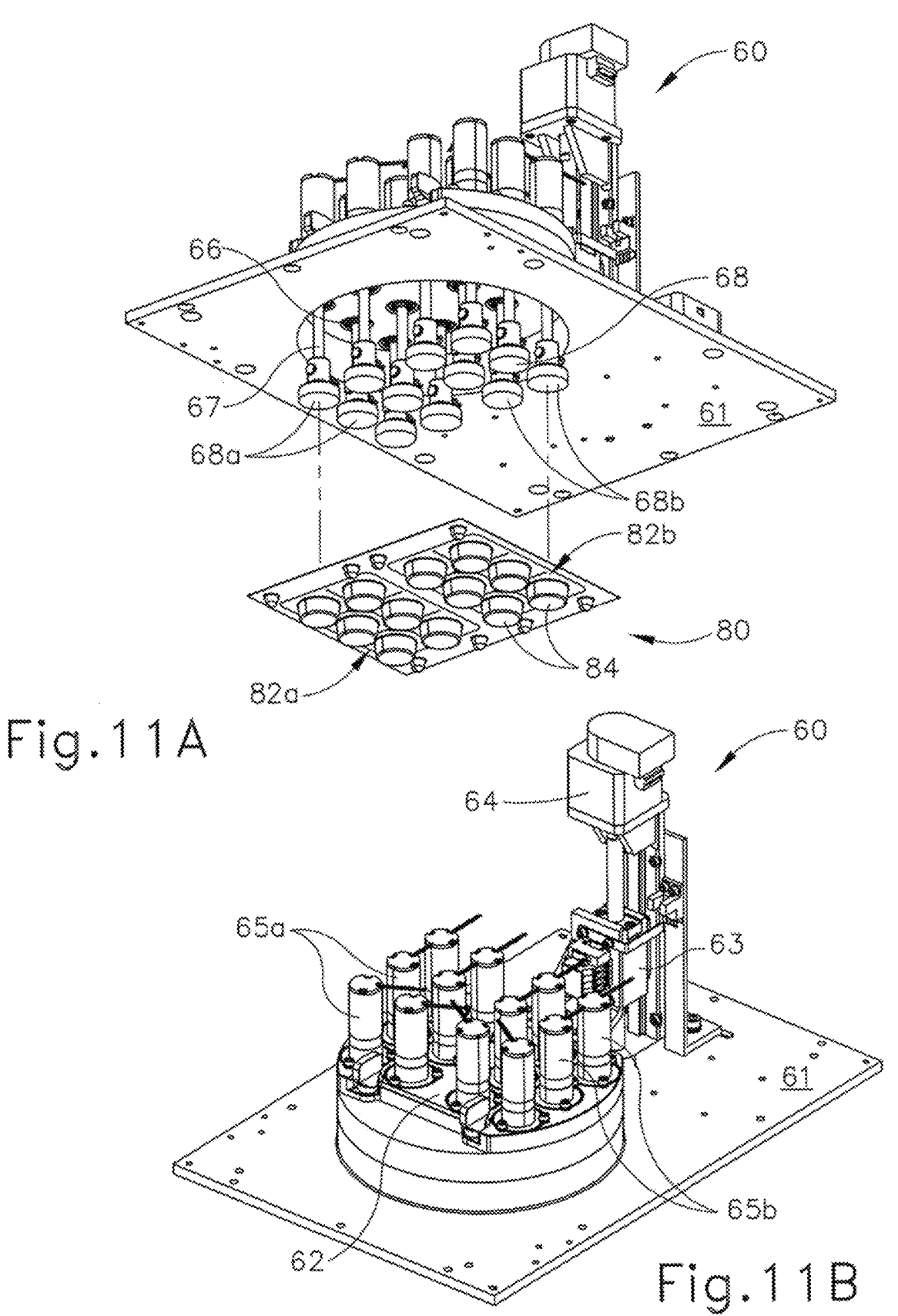
FIG. 11A illustrates a bottom perspective view of a surface finishing apparatus for top-surface finishing of articles formed on a substrate.
FIG. 11B illustrates a top perspective view of the surface finishing apparatus of FIG. 11A.

FIGS. 11A and 11B illustrate a surface finishing apparatus 60 useful for top-surface finishing of articles formed on a substrate, and specifically dosage tablets formed within the depressions 84 of blister cards 82 of a substrate 80. The surface finishing apparatus 60 includes a base 61, and a tamp manifold 62 comprising a plurality of tamps having a tamp stem 67 and a tamp head 68. The upper ends of the tamp stems 67 are actuated vertically by the corresponding plurality of solenoids 65 positioned on the tamp manifold 62 on the top surface of the base 61. The tamp stems 67 extend through openings 66 in the underside of the manifold 62. The base is configured for sealable attachment to and easy removal from the ceiling panels 33 of the containment housing, with the plurality of tamp stems 67 and tamp heads 68 extending through the open port 34*d* in the ceiling panel 33 of the containment housing 30 (see FIG. 2). A lift bracket 63 attached rigidly to the tamp manifold 62 is vertically moveable by a hoist or lift 64 to raise up the tamp manifold 62, the solenoids, and the tamp heads 68 upward and through the open port 34*d* in the ceiling panel, for removal, cleaning or repair. The plurality of tamp heads each have a head diameter and lower surface for extending at least partly into the upper part of a depression, and contacting the construction material, powder layer or wetted powder layer. As shown in FIG. 11A, the plurality of tamp heads 68 are arranged to provide a first plurality of six heads 68*a* arranged to register with the corresponding six depressions of first blister card 82*a*, and a second plurality of six heads 68*b* arranged to register with the corresponding six depressions of second blister card 82*b*.

<Fused Filament Fabrication>

Fused filament fabrication (FFF) is a three-dimensional printing (3DP) process that uses a continuous filament of a thermoplastic material. The filament is fed from a large spool through a heated extruding head that deposits molten thermoplastic onto a workpiece positioned on a worktable. Upon cooling, the thermoplastic hardens (undergoesphase change) into the finished form. The extruding head or the worktable, or both, are moved under computer control to define the printed shape layer-by-layer. In some embodiments the extruding head moves in the two lateral (x,y) dimensions to deposit a horizontal layer of thermoplastic, at a time; then the worktable or the extruding head is then moved vertically by a small amount to begin a new layer. The speed of the extruder head may also be controlled to stop and start deposition and form an interrupted plane without stringing or dribbling between sections. A wide variety of materials can be formed into a filament and extruded, including thermoplastics such as polylactic acid (PLA), acrylonitrile butadiene styrene (ABS), polyethylene terephthalate glycol (PETG), polyethylene terephthalate (PET), high-impact polystyrene (HIPS), thermoplastic polyurethane (TPU) and aliphatic polyamides (nylon).

A FFF apparatus can be positioned to extend the heated extruding head above the transport surface of the omnidirectional magnetic movement apparatus. In some embodiments, the FFF apparatus is configured to raise and lower vertically (in the +z direction) the heated extrusion head, and the substrate on which the molten thermoplastic material is deposited is moved in the x,y horizontal plane in fine, incremental movement under the control of both the extrusion/print operation (process unit operations) controller and the movement controller. Article are built by extruding a first (or subsequent) layer of the extruded thermoplastic, and then raising the heated extrusion heat an incremental height before extruding the next layer of the extruded thermoplastic on top of the first (or precedent) layer. In some embodiments, the heated extrusion head is vertically stationary and moves in the x,y horizontal plane, while the substrate on which the molten thermoplastic material is deposited can be moved vertically (in the +z direction).

In various embodiments, an active agent-containing article, for example a pharmaceutical dosage forms or active agent-containing medical device can be made in the process system with process unit operations that includes fused filament fabrication. One or more portions of the incremental volume of extruded thermoplastic material contains an active agent that is compatible with the molten temperature at which the thermoplastic material is melted and extruded from the heated extrusion head, thereby forming a pharmaceutical dosage form comprising one or more, including two or more active agents. Examples of dosage forms containing and active and made using FFF processing are described in International Patent Publications WO 2016/038356 (University of Central Lancashire), WO 2018/206497 (Pharmaprint), and WO 2020/240028, WO 2020/240029, WO 2020/240030, WO 2021/115887 and WO2021198308 (Dihesys Digital Health Systems GMBH), the disclosures of which are incorporated by reference in their entireties. A FFF printer device for this method is described in U.S. Pat. Nos. 6,070,107 and 10,259,164, the disclosures of which are incorporated by reference in their entireties.

In some embodiments, an intermediate or unfinished FFF-formed article can be formed, and a separate and predetermined mass or volume of an active-containing powder or active-containing liquid can be dispensed onto or into a cavity of the unfinished FFF-formed article to provide the resulting finished article with a dosage of the active.

<Electromagnetic Irradiation>

Several bands of the electromagnetic spectrum can be useful in performing numerous process unit operations, including X-rays, ultraviolet (UV), infrared (IR) and microwave wavelengths. Each of the wavelength spectrum can provide a useful process unit operation function. These EM irradiations can be produced by a variety of devices. Microwaves are produced by an electron tube called a magnetron, and can heat moisture in an article or intermediate form for phase change and evaporation processes. UV light (10 nm to 400 nm wavelength) is produced by lamps, light-emitting diodes (LEDs) and lasers, and is used for the polymerizing or curing of monomer resins for inks, coatings and adhesives, and for surface and transparent liquid (water) disinfection and sterilization. IR light, covering a broad wavelength range from about 0.78 to 1000 microns, is produced by lamps, light-emitting diodes (LEDs) and lasers, and can be used for heating compounds for evaporating and drying processes. In some embodiments, irradiation can be used to heat and raise the temperature of an energy-absorbing compound within a composition to provide in situ softening or melting of the compound to function as a binding material for the composition, for example, a thermoformable powder composition. Examples of processes and system can be found in U.S. Pat. No. 9,511,028 (J&J), U.S. Pat. No. 11,229,577 (Merck Patent GmbH), US Patent Application Publication US 2007/0238056 (DeGussa AG), US 2009/0060983 (J&J), US 2015/0333291 (TNO) and US 2019/0374471 (UCL Business PLC), and international Patent Publication WO 2015/143553 (Orthopaedic Innovation Centre, Inc), WO 2017/190994 (Merck Patent GmbH), and WO 2018/096363 (UCL Business PLC), the disclosures of which are incorporated by reference in their entireties.

In some embodiments, an article such as a tablet can be formed by spreading a powder material into one or a series of incremental layers, where the powder material includes a fusible material and an active ingredient, and spraying or jet printing a liquid comprising an energy absorbing material onto the powder in a predetermined pattern, such as the pattern of the tablet. The fusiable material is a material that melts and fuses upon heating, and then solidifies upon cooling, and can be one or a mixture of a sugar alcohol including such as mannitol, a polymer, polyvinyl pyrrolidone (PVP), and others. The energy absorbing material can be any material that absorbs IR, NIR, visible light, UV, or microwaves irradiation and converts the irradiation to heat, examples of which are water itself, carbon black, pigments, inorganic salts etc. The irradiation heats the energy absorbing material, melts at least partially the fusible material to fuse the powder layer. Once cooled, an integrated bound-powder layer is formed. Alternatively, the fusing material can be included within the liquid that is printed onto the powder layer. Examples of such a process are described in U.S. Pat. No. 11,229,577 and US Patent Application Publications 2007/0238056, 2019/0374471, 2021/0196572, 2021/0205176, and 2021/0213678, the disclosures of which are incorporated by reference in their entireties.

<Material Phase Change>

In various embodiments, a change in temperature of a construction material or an intermediate article can effect a change in the material from one phase (a liquid, a solid, or a gas) to a different phase, for example by heating or cooling a material that results in evaporation, sublimation, solidification, freezing, melting or condensation. A cooling (energy removal) of a vaporous compound or composition can result in condensing of the compound or a compound in the composition into liquid form (e.g., steam or water vapor into liquid water); or solidifying (freezing) of a liquid compound or a compound in the composition into a solid form (e.g., water into ice, or a molten thermoplastic polymer into a solid). A heating (energy input) of a liquid compound or composition can result in evaporating of the compound or a compound in the composition into a gaseous form (e.g., water or a solvent into a vapor); or melting of a solid compound or a compound in the composition into a liquid form (e.g., ice into water, or a solid thermoplastic polymer into a molten liquid, or a laser-sintered metal particle into a molten metal, and then solidifying back to a solid metal); or subliming water or moisture in a composition into a vapor (e.g., lyophilizing under sufficient vacuum conditions, or dyr ice).

Energy removal or energy input can be affected by any one or more of conduction, convection or irradiation.

In various embodiment, a chemical reaction upon a construction material or an intermediate article can effect a change in a phase change of the material. For example, monomeric and polymeric liquids, such as epoxy, silicones and other adhesives, can be polymerized and solidified using chemical reactants, for example, pH change, saponification, amination; or using irradiation with certain wavelengths of the EM spectrum, such as UV, IR, and microwaves.

<Evaporation and Drying>

The drying step of the wetted powder layer can be conducted after each wetted layer is formed, or after two or more layers, or after all the wetted layers have been formed, or after forming and surface finishing.

In some embodiments, the drying station can be constructed within the containment system, and a fabrication module can be moved within the containment system to the drying station for processing. In other embodiments, the fabrication module can be transferred out of the containment system, processed in a remote drying station, and returned as needed. A drying station constructed outside of the containment system isolates the wetted-layer drying and solvent handling systems of the drying station from the containment system of the dosage forming system.

A first aspect of the drying station is a means for moving a substrate that contains a wetted powder layer on one or more formation surfaces (for example, within the depression). In various embodiments, the substrate is separated from the carrier, and transferred to the drying station, either manually or mechanically. In some embodiments, the carrier with the affixed substrate is removed from the shuttle, either manually or mechanically, and transferred to the drying station, again either manually or mechanically. In other embodiments, the entire fabrication module is transferred to the drying station, either manually or mechanically.

The drying station includes a device for evaporating the water or other solvent of the printing liquid that is contained in excess in the wetted powder material. The evaporating device can employ one or more of infrared, microwave, ultrasonic energy, radiant heat, and convective (hot air) heating, to raise the vapor pressure of and evaporate the solvent, which can include water. In some embodiments, the surface temperature of a wetted powder material, during drying, can reach up to 90° C. or more.

The drying station also includes a solvent removal system for transporting the solvent vapors from the evaporating device to a solvent condensation and collection system. For printing liquids containing only water as a solvent, or minor amounts of organic solvents, the solvent vapors from the evaporating device can be vented to the atmosphere, for example, into a vent hood.

After the wetted powder material has been dried, the dried powder layer contained on or within the substrate can be returned to the containment system, for further processing of the dosage form. In various embodiments, the substrate is reaffixed to a carrier and/or shuttle (the same carrier and/or shuttle from which the specific substrate had been removed for drying), and transferred back to the transport surface and/or containment housing for further processing.

<Sterilization & Sanitizing>

A process system can include a system and a method for sterilization and/or sanitization of articles and objects within or introduced onto the transport surface or into the containment housing, including construction materials, processing materials, substrates, carriers, shuttles, transport modules, fabrication modules, and inspection, process and sampling equipment. Depending on the type of contaminant, the article being formed, and other processes performed within the process system, the sanitizing or sterilizing agent can be an EM spectrum emission or a chemical compound or composition(s). Non-limiting examples of a sanitizing or sterilizing agent can include UV light, for example, UV-C light, bleaches, peracids, and others.

<Article Inspection and Marking>

An embodiment of a process method or system of the present invention can include process analytical technology (PAT), a summary and examples of which are described at https://en.wikipedia.org/wiki/Process_analytical_technology, the disclosure of which is incorporated by reference in its entirety. The process method or system can include one or more inspection apparatus, inspection system, and inspection process for the one or more process unit operations and/or the one or more intermediate or final articles, to improve the control of the processing system and the quality of the intermediate or final articles. The inspection system can provide real-time monitoring of the processes, the equipment during operation, and the intermediate and final articles, and can include one or more cameras and other digital imaging devices, process parameter sensors, and intermediate and final article parameter sensors. The inspection system can provide real-time feedback, with and without process control, of the real-time monitoring system to the process unit operations controller(s), to improve control and efficiency of the processes and minimize or eliminate off-line quality control inspection and facilities. In some embodiments, the inspection system enables real time release of one or more final articles. Non-limiting examples of inspection apparatuses, inspection systems, and inspection processes are described in U.S. Pat. Nos. 8,252,234 and 8,101,244 (both SmithKline Beecham Corporation), the disclosures of which are incorporated by reference in their entireties.

In various embodiments, the process system can include visual sensors or cameras to intermittently or continuously monitor a volume of construction material deposited onto a substrate. A determination can be made of a mass of construction material deposited individually and in total into a cavity by the multiple of a determined or measured volume of the construction material and a known or determined density of the construction material.

In some embodiments, the process system can employ a PAT system that includes spectrographic sensors, a non-limiting example being a near IR sensor to intermittently or continuously monitor for the uniformity of material that is then deposited within one or more individual cavities for determining the accuracy and potency of a volume of construction material.

In some embodiments, the process system can employ a PAT system that includes sensors, a non-limiting example being a microwave resonance sensor to intermittently or continuously monitor for the density of material that is then deposited within one or more individual cavities for determining the mass of a volume of construction material.

In some embodiments, the process system can employ a PAT system that includes spectrographic and visual sensors and cameras to intermittently or continuously monitor for the positioning of construction material deposited and/or repositioned within one or more individual cavities for determining the accuracy of a dispensing devise to dispense a predetermined volume of construction material. In some embodiments, the PAT system can be used to monitor, evaluate and control a leveling process, as described herein, that moves a powdered construction material deposited within a cavity or depression to form a layer of the powder material having an even or flat upper surface.

In one embodiment, a PAT system and/or device can provide a means for detecting an outer surface, and in particular the outer upper surface, of a particulate or viscous material, or a shaped article, and determining a shape, texture, and dimensions in three-dimensional coordinates (hereinafter, referred to as "3D coordinates") thereof. In addition, the system and/or device can determine the 3D coordinates of an inside surface within a confined space of known or determined geometry (for example, a cavity of a blister card depression) of a substrate or other surface. From the 3D coordinates of the upper surface of the particulate or viscous material, or cavity surface of a substrate, the system can determine or calculate a real volume of deposited particulate material or other type of material, which may include liquids, suspensions, semi-solids or similar, within a cavity, by a difference in the volumes determined between the 3D coordinates of the upper surface of materials within a cavity both before and after the particulate material or other material has been deposited.

In some embodiments, the particulate material is a powder material and the process for forming an article is a binder jetting process in which a binding liquid is dispensed onto a layer of a powder material to form a wetted bound-powder material, and a subsequent dose or layer of powder material is deposited onto the upper surface of the wetted bound-powder material. The PAT system detects the 3D coordinates of the upper surface of the wetted bound-powder material within a cavity, and then the 3D coordinates of the upper surface of the powder material deposited onto the wetted bound-powder material. The upper outer surface of a deposited powdered material, or a wetted bound-powder material, can be planar and flat, or can be a contoured, with curves and slopes on the upper surface. A volume difference can be determined based on the respective 3D coordinates of the upper surfaces of the deposited powdered material and the wetted bound-powder material. A volume of a recently-deposited dose of powder material into a cavity can be determined by a difference between the determined volume of total material within the cavity before and after its depositing into the cavity.

Figure 12A:
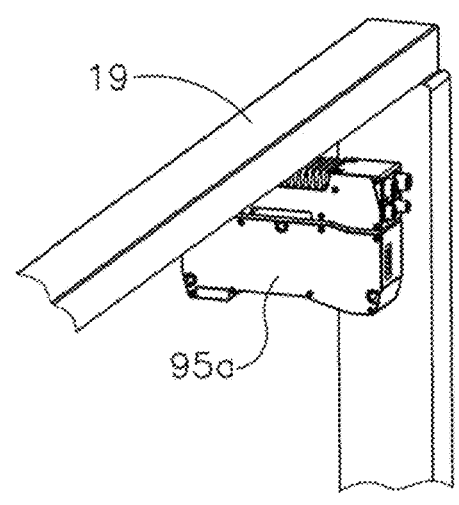
FIGS. 12A and 12 illustrate an imaging device for scanning the surface contours of a substrate and of construction material deposited within a depression of the substrate.
Figure 12B:
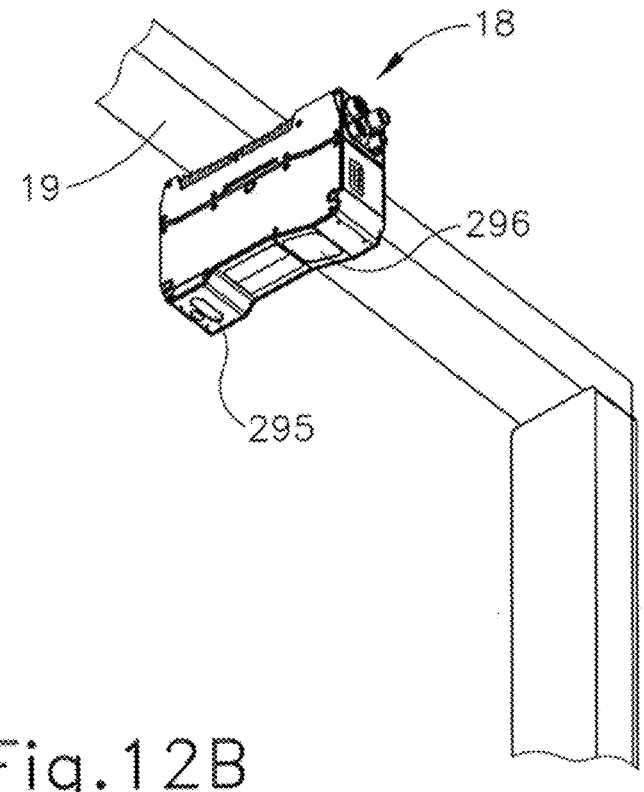

An example of a device for detecting the 3D coordinates of an upper surface of a powdered material within the space of the cavity is a three-dimensional (3D) laser camera. An example of a 3D laser camera 95a is shown in FIG. 1 and in FIGS. 12A and 12B. The 3D laser camera 95a is mounted on an overhead frame 19 vertically above the containment housing 30 for imaging of the containment zone and the fabrications modules through the transparent ceiling panel 33. An example of such a 3D laser camera is made by Cognex Corporation, for example model InSight® 3D-L4000 Series.

A 3D laser camera includes laser 295 (FIGS. 12A and 12B) illustrate a means for emitting a plane of laser light onto the contoured surface of the cavity, or a material within the cavity, as the case may be. A laser light detector 296 of the 3D laser camera views the contoured surface at a perspective angle to the laser plane, and captures an image that detects where the laser plane strikes the contoured surface, referred to as a laser stripe. The captured image of the laser stripe is then correlated to account for the perspective angle of the plane of the laser light relative to a true vertical plane, and for the perspective angle of the laser light detector relative to the plane of the laser light, to generate a corrected elevation profile of the laser stripe along the contoured surface.

When an empty depression of a blister card is scanned, each corrected elevation profile generated provides a true reference profile of the empty depression surface taken along the laser plane, and the cumulative series of corrected elevation profiles provides the 3D coordinates of the surfaces of the depression, including the 3D coordinates of the floor and sidewalls of the depression, and the top sheet of the blister card. Likewise, when a depression contains a powdered and/or wetted bound powder material and is passed under the 3D laser camera, each corrected elevation profile generated provides a true reference profile of the depression and powder material surfaces taken along the laser plane, and the corresponding cumulative series of corrected elevation profiles provides the 3D coordinates of the depression, the contoured surface of the powder material within the depression, and the top sheet of the blister card.

A volume under, or over, a contoured surface of the powder material can be determined by one of a number of calculation methods. In one generalized method, the width space between each incremental laser stripe is multiplied by an area under, or over, the curve of the incremental laser stripe to obtain an incremental volume, and the sum of the incremental volumes provide a cumulative volume of material under, or over, the 3D contoured surface of the powder material. By previously determining a total volume of material beneath a contoured surface of material within the cavity before depositing the powdered material, the volume of deposited powder material is determined by the difference with the volume beneath the deposited powder material. Similarly, by previously determining a total volume of space above a contoured surface of material within the cavity (up to the opening of the depression), before depositing the powdered material, the volume of deposited powder material is determined by the difference with the space within the cavity above the deposited powder material and up to the opening of the depression.

Once a volume of deposited powder material has been determined, a determination of the mass of the deposited powder material can be made by multiplying the volume by a density of the powder material. The density of the powder material can be determined by one or more methods, including continuous measurement by microwave resonance or similar, for example as described in U.S. Pat. No. 5,977,780, the disclosure of which is incorporated by reference in its entirety, or a predetermined density value based upon empirical data, which can be measured independently or simultaneously.

In one embodiment, the 3D coordinates of the contoured surface of the material can be divided into a regular matrix of unit areas in the two horizontal dimensions, and the elevation of each unit area can be defined by one, more or all elevation measurements detected within that unit area. The average elevation of the contoured surface of the material, depicted as a horizontal planar surface, is the average elevation of the total unit areas detected over the contoured surface of the material.

Figures 19A, 19B, 20A, 20B, 21A, 21B, 22A, 22B:
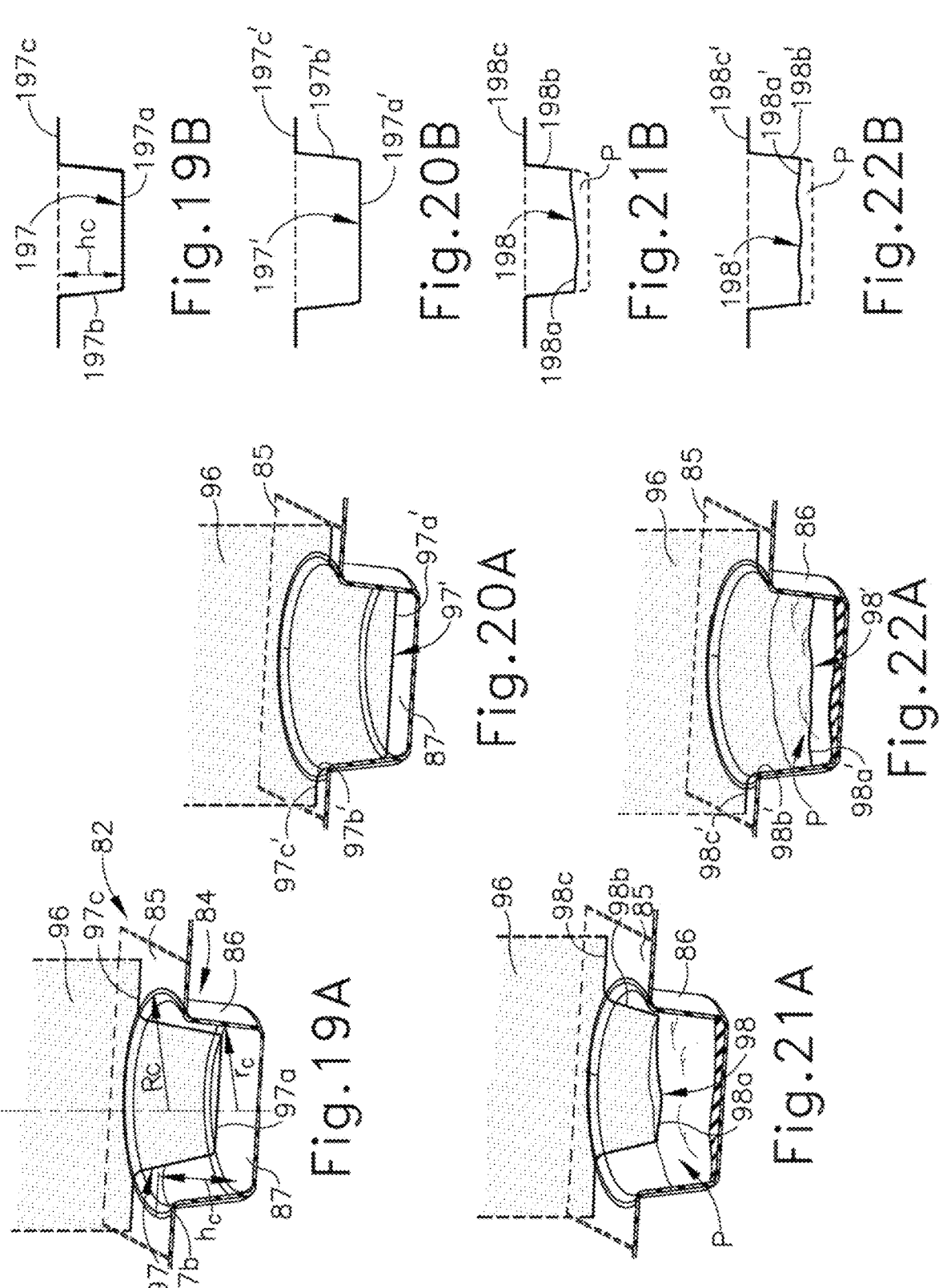
FIG. 19A illustrates in top perspective section view a typical depression in a blister card passing through a laser stripe plane to generate a first laser stripe image along the contoured surface of the blister card.
FIG. 19B illustrates a side sectional view of a corrected elevation profile of the contoured surface of the blister card determined from the laser stripe image generated in FIG. 19A.
FIG. 20A illustrates in top perspective section view of the blister card of FIG. 19A with the laser stripe plane passing through a second portion of the blister card, to generate a second laser stripe image along the contoured surface of the blister card.
FIG. 20B illustrates a side sectional view of a corrected elevation profile of the contoured surface of the blister card determined from the laser stripe image generated in FIG. 20A.
FIG. 21A illustrates in top perspective section view a partially-filled depression in the blister card of FIG. 19A, passing through the laser stripe plane to generate a laser stripe image along the contoured surface of the blister card.
FIG. 21B illustrates a side sectional view of a corrected elevation profile of the contoured surface of the blister card with the partially-filled depression, determined from the laser stripe image generated in FIG. 21A.
FIG. 22A illustrates in top perspective section view of the blister card of FIG. 20A with the laser stripe plane passing through a second portion of the blister card with the partially-filled depression, to generate a laser stripe image along the contoured surface of with the partially-filled depression.
FIG. 22B illustrates a side sectional view of a corrected elevation profile of the contoured surface of the partially-filled depression of the blister card, determined from the laser stripe image generated in FIG. 22A.

In a non-limiting example, a detection apparatus and method can be used during an article formation process, to determine the volume of an incremental dose or layer of powder material that has been deposited within one or more cavities of a blister card. As shown in FIG. 19A, a typical depression 84 in a blister card 82 has a slightly-tapered sidewall 86 and a flat bottom floor 87, to provide a circular cavity in the shape of a truncated cone. The dimensions of the blister cavity, including a reference depth hc of the base floor, a lower cavity radius re of the floor 87, and an upper cavity radius Rc of an upper opening of the depression 84 in the sheet 85 of the blister card 82, can be determined by 3D scanning method described above. As a blister card passes through a stationary laser plane 96 emitted by the laser 295 of the 3D laser camera 95*a*, each blister depression 84 is exposed to the laser plane 96, including the upper surface of the sheet 85, sidewall 86, and floor 87 of the blister card 82, and an imaging component of the 3D laser camera (for example, imaging camera 95 shown in FIG. 1), consisting of a laser light detector 296, captures a sequence of multiple images of the laser stripe exposed onto the blister card 82 and each depression 84. FIG. 19A shows a first laser stripe 97 exposed along a first lateral portion of the blister depression, including portion 97*a* along the floor 87, portions 97*b* along the inside walls, and portions 97*c* along the sheet 85, and FIG. 20A shows a second laser stripe 97' exposed along a second lateral portion of the blister depression, including portion 97'*a* along the floor 87*a*, portions 97'*b* along the inside walls, and portions 97'*c* along the sheet 85 of the depression 84. The PAT system then generates a corresponding sequence of corrected elevation profile of the laser stripe along the contoured surfaces. Two of the corrected elevation profiles, corresponding to the two captured images of the laser stripes 97 and 97', are a first corrected elevation profile 197 shown in FIG. 19B, and a second corrected elevation profile 197' shown in FIG. 20B.

The PAT system uses the sequence of corrected elevation profiles to generate 3D coordinates of the surface features and contour of the cavity of the depression 84, from which the PAT system can calculate or determine an initial volume V0 of the empty depression 84, using the floor 87 as a first reference distance, representing a base elevation h0, and the upper surface of the sheet 85 of the blister card 82 as a second reference elevation, representing an upper elevation hmax.

After a powder material has been deposited in and/or leveled within a circular cavity of a depression 84, the partially-filled depression 84 can be passed again through the stationary laser plane 96, exposing the upper surface of the sheet 85, a portion of the sidewall 86, and the upper surface of the layer of powder material P disposed within the cavity of the depression 84 to the laser plane 96. The imaging component of a 3D laser camera captures a new sequence of multiple images of the laser stripe as the same blister card 82 and each partially-filled depression 84 passes incrementally below and through the laser plane 96 FIG. 21A shows a first laser stripe 98 exposed along a first lateral portion of the partially-filled blister depression, including portion 98*a* along the floor 87, portions 98*b* along the inside walls, and portions 98*c* along the sheet 85, and FIG. 22A shows a second laser stripe 98' exposed along a second lateral portion of the partially-filled blister depression, including portion 98'*a* along the floor 87*a*, portions 98'*b* along the inside walls, and portions 98*c*' along the sheet 85 of the depression 84. The PAT system then generates a corresponding sequence of corrected elevation profile of the laser stripe along the contoured surfaces of the partially-filled depression. Two of the corrected elevation profiles, corresponding to the two captured images of the laser stripes 98 and 98', are a first corrected elevation profile 198 shown in FIG. 21B, and a corrected elevation profile 198' shown in FIG. 22B.

The PAT system uses the sequence of corrected elevation profiles to generate 3D coordinates of the surface features and contour of the partially-filled depression 84, from which the PAT system can calculate or determine an initial volume $V_0$ of the empty depression 84, using the floor 87 as a first reference distance representing a base elevation $h_0$, and the upper surface of the sheet 85 of the blister card 82 as a second reference elevation representing upper elevation hmax.

The PAT system uses the new sequence of corrected elevation profiles to generate 3D coordinates of the surface features and contour of the partially-filled depression, including the exposed portions of the depression and the layer of powder material P disposed within the cavity of the depression 84. The PAT system determines an average elevation of the contoured surface of the powder material (average upper surface elevation, hp), which can be depicted as a horizontal planar surface, based on an average of the corrected elevation profile elevations of the upper surface of the layer of powder material P, or a portion thereof.

A volume of the powder material P can be calculated based on an equation for the volume ($V_{tc}$) of a truncated cone of formula (1):

$$V_{tc} = (1/3) * \pi * \Delta h * (r^2 + r*R + R^2), \tag{1}$$

where: Δh is the distance difference between a bottom planar surface and a top planar surface of the truncated cone, r is the radius of the bottom planar surface of the truncated cone, and R is top planar surface of the truncated cone.

An empty depression of a commercial blister card has an elevation of the floor of the depression $h_0$ and of the top edge of the depression wall hr, an outside angle θ of the depression wall from horizontal, a radius $r_0$ of the floor of the depression, and the radius Rr of the top edge of the depression. The dimensions and physical parameters of a depression of a blister can be measured using the present scanning system, or are predetermined from the fabrication process for the blister card itself. Knowing the outside angle θ and either of radius $r_0$ or radius Rr of outside angle θ, or both the radii $r_0$ and Rr, the detected total depth of the empty depression enables determination of the empty volume above the floor of the depression to the top edge.

After depositing a first dose of powder material on the floor of the empty depression, and optionally though preferably after leveling the powder material to a first incremental layer of powder, an average elevation of the contoured surface of the dose or incremental layer of powder is detected as described above, and designated the average upper surface elevation, hp, of the powder. A powder layer radius $r_{p1}$ can also be estimated. Knowing both the outside angle θ and either of radius $r_{p1}$ or radius Rr, or knowing the radii $r_{p1}$ and Rr, the detected average upper surface elevation of the first incremental layer of powder enables determination of the volume of the first incremental layer of powder. In one method, the average upper surface elevation of the first incremental layer of powder is the bottom planar surface for calculating the empty volume above the first incremental layer, and the volume of the first incremental layer of powder is the difference with the empty volume of the depression. In another method, the average upper surface elevation of the first incremental layer of powder is the top planar surface for calculating the volume of the first incremental layer of powder above the floor of the depression.

After printing binder liquid on the first incremental layer of powder, an average upper surface elevation of the first layer of wetted powder can optionally be detected and determined.

After depositing a second dose of powder material on the first layer of wetted powder, and optionally though preferably after leveling the powder material to the second incremental layer of powder, an average elevation of the contoured surface of the second dose or incremental layer of powder is detected as described above, and designated the average upper surface elevation, hp, of the second layer of powder. A second powder layer radius $r_{p2}$ can also be estimated. Knowing the outside angle θ and either of radius $r_{p2}$ or radius Rr, or the radii $r_{p2}$ and Rr, the detected average upper surface elevation of the second incremental layer of powder enables determination of the volume of the second incremental layer of powder, by either of the methods described above. The procedure and determination of the volumes of the successive incremental layer of powders proceeds in the same manner.

The detected elevation measurements and other dimensions of the blister depressions such as upper edge radius, floor radius and wall angle of the depressions, can be automatically and instantaneously sent to a controller operating one or more software systems; for example, KAX Group software ProaXesS, for using the generated 3D coordinates of the surface features to calculate the average upper surface elevation of the powder layers, and the volumes beneath, or above, the calculated average upper surface elevation of the incremental powder layers.

In various embodiments, the controller determines the average upper surface elevations and volumes of the powder layers using the entire scanned surface of the deposited or leveled powder. In some embodiments, the controller uses an area of not less than 20%, more typically not less than 50%, and preferentially not less than 75% of the scanned surface of the deposited or leveled powder. In other embodiments, the controller selects a single, or two or more, target areas that are not less than 20%, more typically not less than 50% and preferentially not less than 75% of the scanned surface of the deposited or leveled powder. In some embodiments, the selected area of the scanned surface of the deposited or leveled powder used to calculate the average upper surface elevation is an area of about 25 square millimeters ($mm^2$) or more, selected from a predetermined position on the scanned surface of the deposited or leveled powder. Depending on the total area (size) of the blister depression, the area of the selected area can be from 25 $mm^2$ to about 100 $mm^2$, the selected area representing not less than 20%, more typically not less than 50%, and preferentially not less than 75% of the scanned surface of the deposited or leveled powder.

<Material Placement>

An embodiment of the process utilizes one or more measuring devices, for example, short wave IR cameras to monitor the quality and accuracy of print fluid deposition.

The PAT system can include a sub-system for monitoring and assessing the effectiveness of liquid dispensing processes. The sub-system can include a non-contacting spectral imaging camera configured to use one or more, in series or parallel, bandpass filters. In some embodiments, the device precisely detects and records location data of individual dispensed or printed liquid droplets and/or the deposit pattern formed from a plurality of droplets deposited onto a substrate or construction material. The PAT system can then compare that location data in real-time to a printing image and/or concentration specification used by the processing system to control the droplet dispensing rate and pattern, and amount of one or more API compounds deposited in the one or more individual cavities during article formation. The sub-system provides a means for measuring, recording and reporting on a continuous basis the quality and consistency of a prescribed printing process. The camera system can incorporate intelligent data processing algorithms, including where appropriate artificial intelligence, to assess and determine if an article has passed the inspection, or has failed inspection and thus requires re-working within the process or quarantining.

In various embodiments the aforementioned means for measuring, recording, and reporting on a continuous basis the quality and consistency of a prescribed printing process may consist of an integrated shortwave infrared (SWIR) imaging sensor. The SWIR sensor may operate in, but not limited to, the 550-2500 nanometer (nm) range, and typically the 1,050-2500 nm range, and more typically the 1,400-1650 nm range, a zone of light waves above the visible and NIR ranges. The surface of a material being processed can be illuminated with a light in the SWIR range of a known wavelength and intensity, either emitted from a separate SWIR light source or the SWIR sensor device itself. Depending on the composition of the material on or near the surface (SWIR wavelengths can penetrate into the depth of many materials), certain of the emitted SWIR light waves are absorbed by the compounds of the composition, and in combination with bandpass filters, an image may be constructed based on the SWIR light waves reflected by the target object and absorbed by the SWIR sensor. The image can be interpreted to identify the location of a material or composition, and a component or components of the material. In one non-limiting example, in a process where an aqueous binding liquid is dispersed as a multiplicity of droplets onto a surface of a powder material disposed within a blister cavity, the SWIR imaging sensor can monitor the effectiveness of a liquid dispensing process to dispense a known volume of the binding liquid on a predetermined target area. A control system can interpret the actual dispensing pattern and compare the same to the predetermined target area, and direct the processing system to take subsequent action.

In various embodiments, a SWIR imaging sensor can determine that a liquid dispensing process has failed to dispense droplets of a liquid from one of the dispensing nozzles (also referred to as jets), for example, due to a clogging of the jet, which can result in an unprinted portion of the expected print pattern of the liquid that the liquid dispensing system was programmed to take, leaving an unprinted area on the construction material. In a binder jetting process, a series of wetted bound-powder layers may have unintentional overlapping lines of unwetted or weakly wetted powder However, as a result of the detected error in the actual dispensing pattern, the processing system can be programmed to take one or more further processing steps or re-processing steps to avoid an ill-effect of the dispensing error being expressed in the processed article.

In one example, upon detection of a dispensing error, the control system can generate a new command to print a correction pattern of liquid only in the unprinted area, using a printing nozzle(s) that is operating properly, thus dispensing liquid onto the previously missing area and correcting the printed area to match the originally commanded print pattern.

In another example, the process system can be programmed to command the conveying system to pass the fabrication module, and the substrate and the construction material (powder material) thereon, beneath the array of printing nozzles along altered, laterally-offset paths with a different set of the print nozzles to print the predetermined target area on subsequent layers of powder material. In this process, if a jet becomes blocked and cannot dispense the binding liquid as instructed, the PAT system will recognize the linear pattern of missing liquid in wetted powder surface, but the altered, laterally-offset path is taken when the next layer of powder material is printed while shifting the missing printed area to a different position in the wetted bound-powder layer, which staggers the line of missing liquid laterally in the series of incrementally wetted bound powder layers.

In addition, once the line of unprinted construction material is detected, the printing program can be commanded to dispense additional binding liquid from a nozzle or the two nozzles adjacent to the malfunctioning jet, to place additional liquid in the near vicinity of the unprinted line of powder material, which can migrate laterally into and fill the powder material with sufficient liquid to sufficiently bind together the powder material and avoid the ill-effect of the dispensing error. Alternatively, the processing system can command the liquid dispensing system to deposit a larger volume of liquid in subsequent liquid-printed patterns along the line or area observed to have a missing amount of liquid as detected by the SWIR image sensor, thereby compensating for the previous layer's missing binding liquid.

In another example, when a line of unprinted construction material is detected, the process system can be programmed to command the conveying system to pass the fabrication module, and the substrate and the construction material (powder material) thereon, beneath a different row printing nozzles, in the array of printing nozzles, to avoid passing the area of the construction material to be printed beneath the clogged or blocked jet, until the clogged jet can be cleaned or cleared or replaced.

Alternatively, the system may be programmed to determine that, based on the printed liquid pattern detected by the SWIR imaging camera, a failure of the print system has occurred of such significance that further processing should be stopped, either to repair or replace the print nozzles, and restore correct operation conditions, or to quarantine the articles under construction.

<Finished Product Qualification>

In various embodiments, a control or PAT process can include an article aesthetic assessment method comprising a step of acquiring a multiplicity of digital images of a processed article or one or more intermediate forms of the article. The multiplicity of images can be classified as one or more classes of article (or intermediate form) images, the classes of images selected from the group consisting of acceptable images and unacceptable images, and the unacceptable images including at least one of rework images and quarantine images. Pre-defined and stored images of articles (for example, dosage forms) of acceptable quality are accumulated and assembled to the class of acceptable images. Pre-defined and stored images of articles (for example, dosage forms) that are not of acceptable quality are accumulated and assembled to the class of non-acceptable images. The non-acceptable images can be further classified as rework images and quarantine images, based on whether the article of the image could be reworked to acceptable quality, or could not be reworked and required quarantining. The method also includes a step of using a multiplicity of the acceptable images to create an algorithm that can distinguish a real-time article image as between an acceptable image or a non-acceptable image. The step can further include a step of using a multiplicity of the rework images to create an algorithm that can distinguish a real-time article image as either a rework image or not a rework image, or alternatively, either a rework image or a quarantine image. The process includes a step of acquiring a digital image of an article in real-time, and a step of analyzing the real-time article image with one or more algorithms to distinguish the live article image as at least one of an acceptable image, an unacceptable image, a rework image and a quarantine image. The process includes a step of further processing a real-time article based on the analysis of its real-time article image, wherein if the real-time article image is determined to be an acceptable image, the real-time article proceeds to a subsequent processing step; if the real-time article image is determined to be a rework image, the real-time article form proceeds to a rework processing step in which the one or more prior processing steps performed on the article are repeated; and if the real-time article image is determined to be a quarantine image, the article proceeds to a quarantine processing step in which the real-time article is removed from the process system and quarantined. The article aesthetic assessment method can be built from a database of images that is continually updated with additional images of articles are produced by the process system having an outer surface of acceptable quality and appearance, to continually reduce false negatives or false positives over time as articles are produced with the processing system.

In various embodiments a two-dimensional (2D) camera imaging system, for example a Cognex In-sight 9000 series camera, can be used to inspect the finished product after all processing has been completed. In some embodiments, the 2D camera can image a surface of a construction material or a processed construction material (for example, a wetted bound-powder layer), and determine a surface quality of the upper surface layer of the bound powder matrix, using the article aesthetic assessment described above.

In various embodiments, the aforementioned two-dimensional camera imaging system can be installed and used for monitoring, for example though without limitation, a top surface quality of a processed article. The control system can be programmed to take subsequent processing action, depending on the result of the assessment made by the 2D camera imaging system. If the 2D camera, for example, determines that the image of the top surface of the processed article is a non-acceptable image and a rework image, the process control system can command re-processing (re-working) of the processed article back through a top surface smoothing/tamping unit operation, and then re-imaging the top surface of the reworked article to inspect and determine if the non-acceptable surface finish has been corrected. The process control system can be configured to command a reprocessing of the processed article one or more times until satisfactory results are achieved, or quarantined. Alternatively, if the 2D camera imaging determines that the image of the top surface of the processed article is a quarantine image, the process control system can command the article to be quarantined. A determination that processed articles are being reworked and/or quarantined excessively can be identified, the control system can halt further processing operations until the system operation is inspected, and corrective action taken.

<Unloading of Completed Articles>

In various embodiments, following the formation of an article upon or within a substrate, the article is then removed from the substrate for further processing, including packaging. The removal of an article from a substrate can be performed within the processing system, or over the transport surface of the magnetic movement apparatus, and/or within the containment system, or can be performed at a remote site or system.

In various embodiments, the substrate can provide a portion of the packaging for the article, in which case the article remains in the substrate and is further processed, including by further addition of a construction material and/or phase modification, which can include drying, and/or packaged. For example, at the completion of the dosage formation within or upon the formation surface, the fabrication module can be moved to an unloading station within the magnetic movement system. In some embodiments, the substrate with the formed article disposed within its formation surface, such as a blister tray loaded with dosage forms, is removed from the transport module, either manually or mechanically, and more specifically from the carrier of the transport module.

In mechanical removal embodiments, a device separates and raises the loaded substrate from the carrier, and transports the separated, loaded substrate to an area outside the process system, and more specifically, to a substrate or blister inspection apparatus, and then to a substrate or blister sealing apparatus, for sealing the dosage forms within the depression from the environment, for storage and transportation.

Figure 17A:
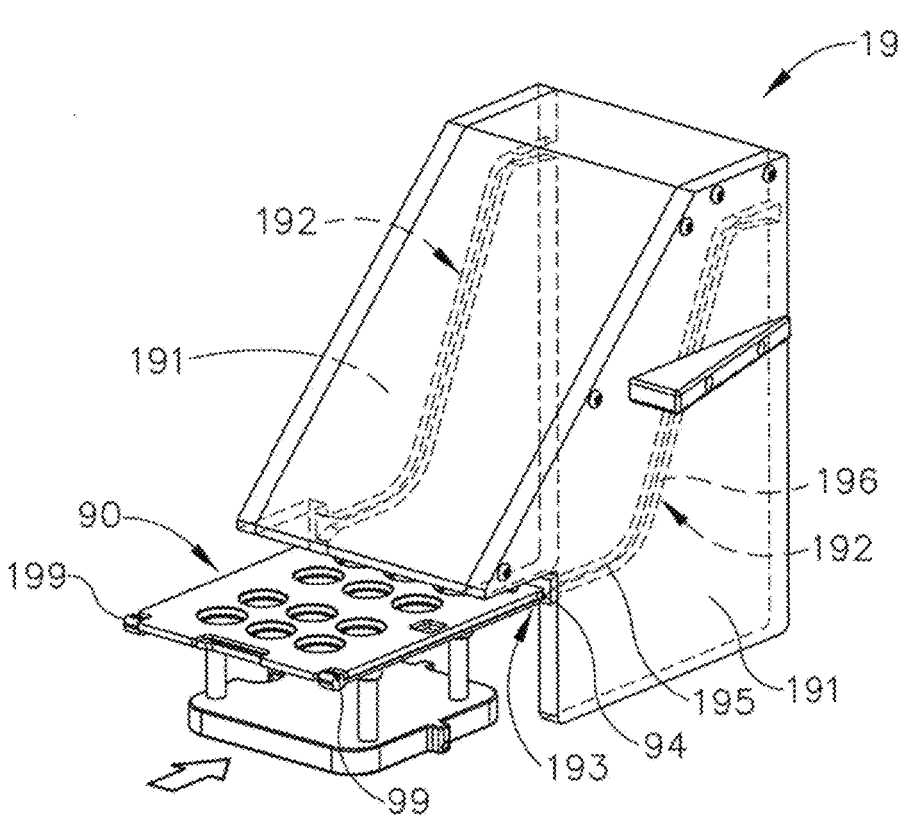
FIG. 17A illustrates in perspective view a mask-raising device for raising and removing a mask from a fabrication module.
Figure 17B:
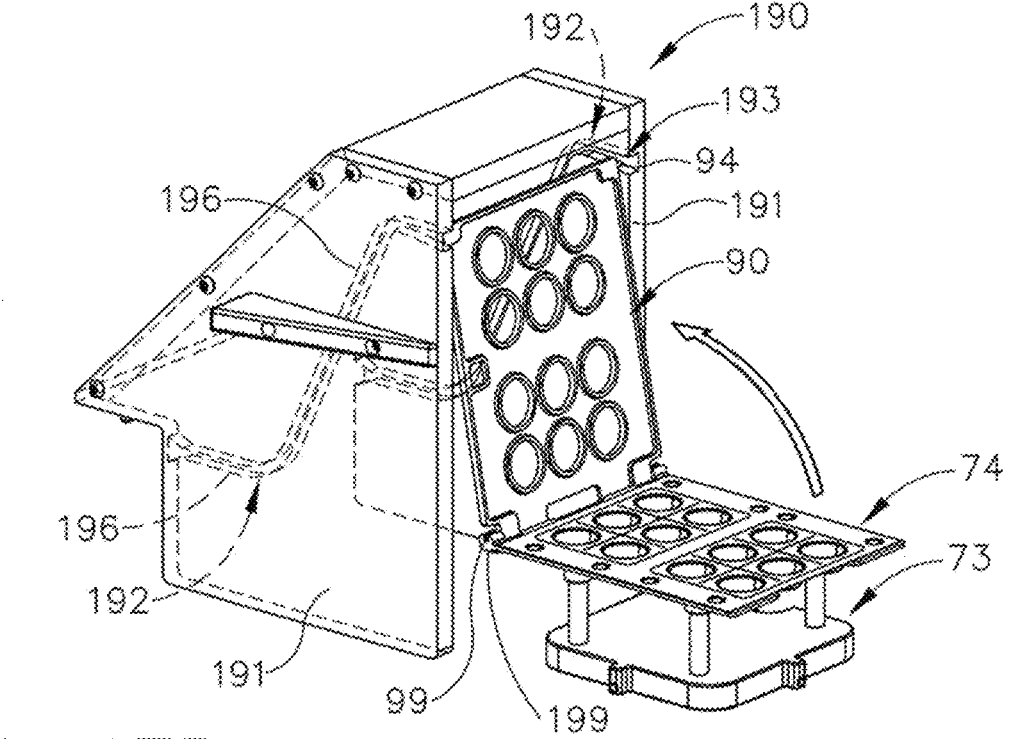
FIG. 17B illustrates in perspective view the fabrication module of FIG. 17A, with the mask raised in a hinged manner by the mask-raising device.

In another embodiment, after finished articles have been formed on the substrate (for example, a blister card with dosage forms formed within the depressions), the fabrication module is controlled to exit the containment zone through a mask-raising device 190 positioned at the transport opening 36 of the containment housing. The mask-raising device 190 provides a vestibule in which the mask 90 of a fabrication module can be raised up off of the substrate 80 and the nest 74 of the fabrication module 70, and removed manually or mechanically. As shown in FIG. 17A, the mask-raising device 190 has a pair of side walls 191 forming the vestibule, spaced apart laterally to allow the fabrication module to pass therebetween in close, non-contacting clearance with the side walls 191. The side walls 191 each have a narrow groove 192 formed into an inner surface, in a mirror-image pattern. Each fabrication module 90 can have a pair of pins 94 (FIG. 6) on opposite sides of a forward end of the mask 90, extending laterally outward from the sides of the mask 90 and beyond the lateral sides of the nest 74. Each groove 192 has an entry 193 at a leading edge of the side wall at an elevation that aligns with the pins 94 of the mask 90. As the fabrication module 70 enters the vestibule, the pin 94 of the mask 90 enters into and passes along a horizontal portion 195 of the groove 192, and is guided along a curve in the groove to a second angled portion 196, angled at about 45-75 degrees from horizontal. As pins 94 ride up the angled portion 196, the leading end of mask 90 is raised up and off the nest 74. The mask is thereby controllably and completely raised in a hinged manner off of the blister card, thereby exposing, as shown in FIG. 17B, the blister card for inspection, and manual or automated removal of the blister card from the carrier and subsequent processing or handling. Inspection of the blister card, including the finished dosage forms can include an inspection of the surface finish for flaws or defects, as described herein. Upon removal of the one or more blister cards, the carrier can be manually or automatically reloaded with a new blister card and the hinged mask element controllably lowered to a position where it covers the newly placed blister card.

<Packaging and Sealing>

After the final dosage is formed, the substrate with the completed one or more dosage forms disposed within the depressions of the blister sheet, moves to a blister card inspection device and subsequently to a sealing and cutting device. Sealing and cutting of blister sheets is well known in the art, and can be constructed within the containment system, so that the sealed blister sheets are formed within the containment system, or transferred out of the containment system, and sealed and cut in a packaging system outside of the containment system.

<Restoration Devices>

The invention also includes restoration devices that can clean or repair the depositing mechanism of the depositing device, or the phase modification mechanism of the phase modification device, to restore their performance, while the depositing device or phase modification mechanism or device is in-place. In one non-limiting example, a print nozzle cleaning device comprises a nozzle cleaning shuttle and a nozzle cleaning substrate fixed to the nozzle cleaning shuttle, which can pass under the printing nozzles, with the nozzle cleaning substrate configured to wipe and clean the printing nozzle, to restore their printing performance.

Figures 13, 14, 15:
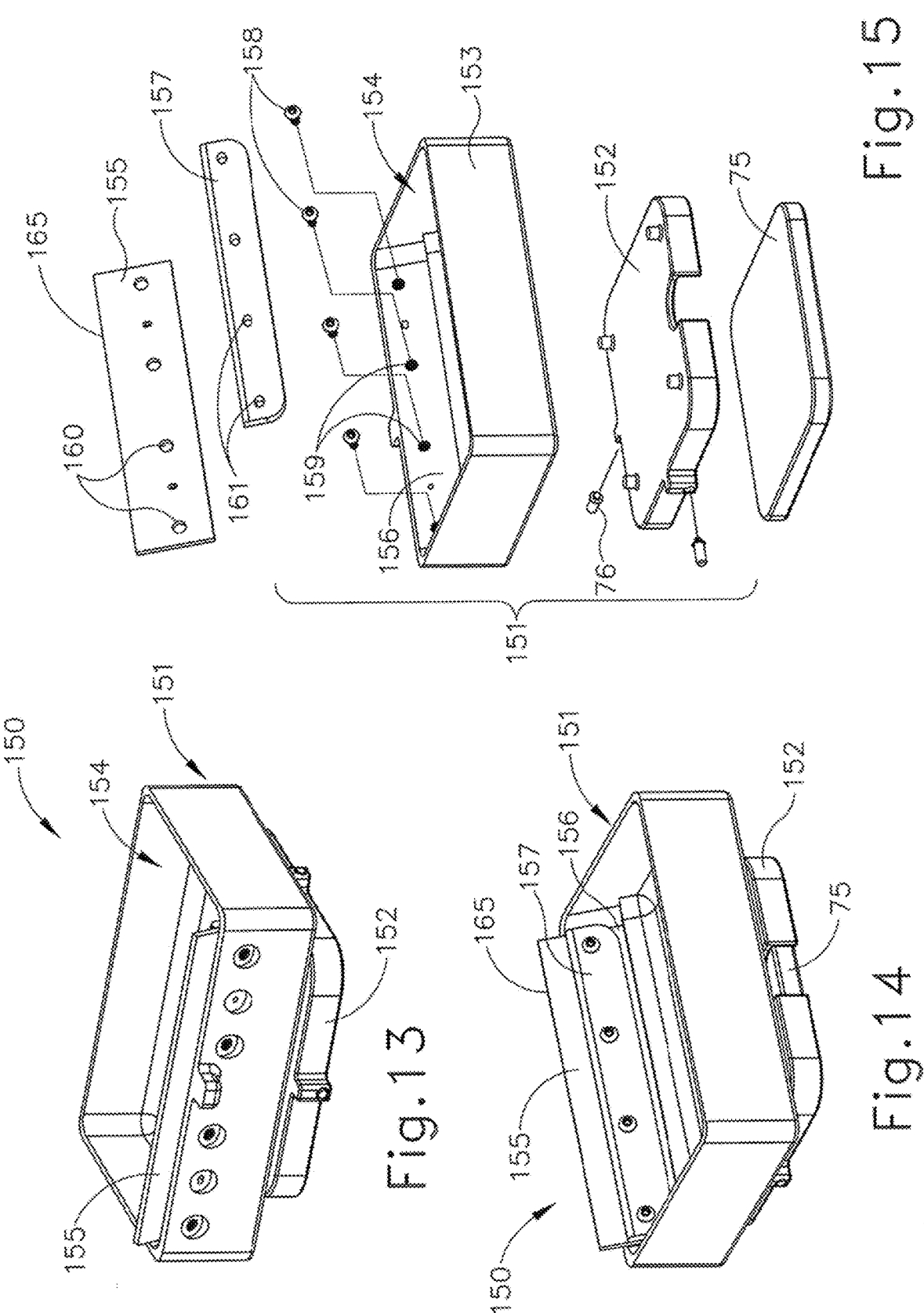
FIG. 13 illustrates in top, front perspective view a print nozzle cleaning device, for use with a shuttle.
FIG. 14 illustrates in top, rear perspective view the print nozzle cleaning device of FIG. 13.
FIG. 15 illustrates an exploded view of the elements of the print nozzle cleaning device of FIG. 14.

An embodiment of a print nozzle cleaning device 150 is illustrated in FIGS. 13-15. The device 150 includes a transport module consisting of a nozzle cleaning carrier 151 and a nozzle cleaning blade 155, and a shuttle 75 (as described elsewhere herein) that provides movement of the nozzle cleaning device 150 over the process surface 16. Nozzle cleaning carrier 151 has a base 152 that has a planar cavity within which the shuttle 75 exactly fits, and a frame 153 for securing the nozzle cleaning substrate(s) 155. The base 152 is oriented onto the shuttle 75 with one or more securements, such as threaded screws 76 that pass through positioned holes in a sidewall of the base 152 and impinge against the sides of the shuttle 75. The frame 153 consists of an open-topped container having a container volume 154 of a volumetric capacity sufficient to receive and contain a volume of printing liquid that may remain within the printer housing 551 and printer nozzles 552 when the liquid printing apparatus 50 is being serviced or changed out, or to receive the volume of printing liquid that may be dispensed from the printer nozzles 552 during the cleaning procedure. The frame 153 also includes a sidewall 156 slanted upwardly and outwardly at a predetermined angle, and a securing plate 157 The slanted sidewall 156 has a plurality of threaded holes 159, which register with a plurality of through holes 161 in the securing plate 157, and with a plurality of through holes 160 in the nozzle cleaning blade 155. The nozzle cleaning blade 155 is secured to the slanted sidewall 156 by passing securement screws 158 through the holes 161 in the securing plate 157 and holes 160 in the nozzle cleaning blade 155, and threading securement screws 158 into the threaded holes 159 in the slanted sidewall 156, as illustrated in FIG. 15.

In the illustrated embodiment, the nozzle cleaning blades 155 has an upper edge 165 along the length, and is made of a resilient, elastomeric material, which can include natural or synthetic rubber or silicone, typically having a low durometer that gives the material flexibility. The upper edge 165 engages the nozzles of the printhead(s) to wipe or squeegee away any material that could accumulate on the nozzles and interfere with or block the dispensing of liquid droplets and/or streams. The design and construction of the frame 153 provides the upper edge 165 of the nozzle cleaning blade 155 with an elevation sufficient for the tip of the upper edge 165 to deflect slightly upon engagement with the printer nozzles 552 when the print nozzle cleaning device 150 is magnetically levitated above the process surface 16 by the process movement apparatus 20. As the print nozzle cleaning device 150 moves beneath the printer housing 551, with the sidewall opposite the slanted sidewall 156 leading in a direction transverse to the length of the printing nozzles 552, the tip of the upper edge 165 rubs along the printer nozzles 552. To prevent the deflected tip of the upper edge 165 from flinging any liquid or debris when the tip passes and clears the last printer nozzle 552, the height of levitation of the print nozzle cleaning device 150 can be slightly reduced as the blade disengages from the printing nozzles, to reduce the contact and deflection of the tip of the upper edge 165 against the printer nozzles 552.

In another example, a surface finishing cleaning device comprises a shuttle and one or more tamp head cleaning substrates fixed to the surface finishing cleaning shuttle, which can pass under a surface finishing apparatus (for example, surface finishing apparatus 60 shown in FIGS. 11A and 11B), with the surface cleaning substrate configured to wipe and clean a finishing surface of the tamp heads of the surface finishing apparatus, to remove any debris and restore their finishing surface.

Figures 16A, 16B, 16C:
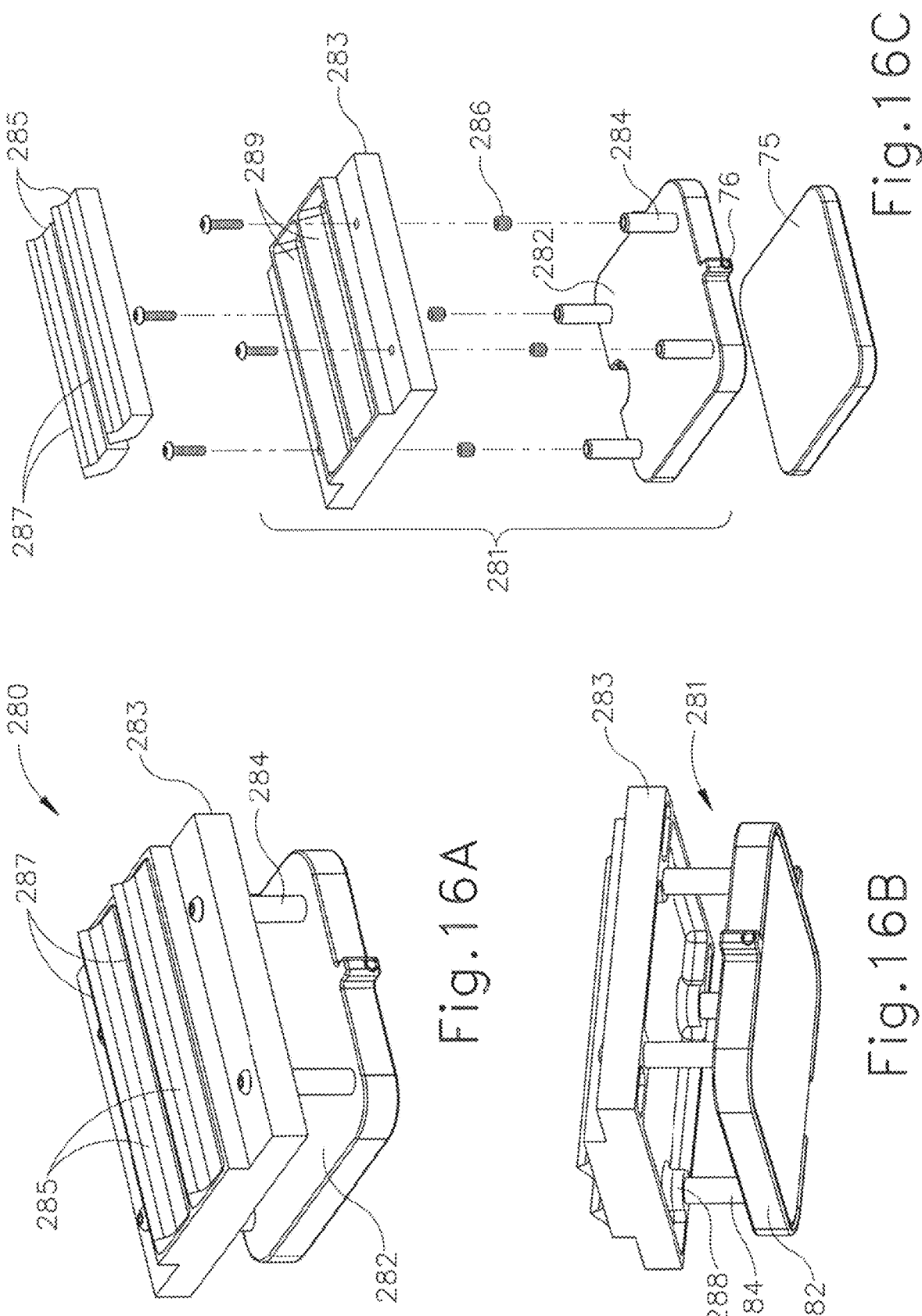
FIG. 16A illustrates in top, front perspective view a finishing surface cleaning device, for use with a shuttle.
FIG. 16B illustrates in bottom, front perspective view the finishing surface cleaning device of FIG. 16A.
FIG. 16C illustrates an exploded view of the elements of the finishing surface cleaning device of FIG. 16A.

An embodiment of a surface cleaning device 280 is illustrated in FIGS. 16A through 16C. The surface cleaning device 280 includes a transport module consisting of a cleaning carrier 281 and a cleaning substrate 285, and a shuttle 75 (as described elsewhere herein) that provides movement of the surface cleaning device 280 over the process surface 16. The cleaning carrier 281 has base 282 that has a planar cavity within which the shuttle 75 exactly fits, and a frame 283 for securing the cleaning substrate(s) 285. Base 282 is oriented onto the shuttle 75 with one or more securements, such as threaded screws 76 that pass through positioned holes in a sidewall of the base 282 and impinge against the sides of the shuttle 75. Frame 283 includes a pair of elongated rectangular pockets 289 shaped for receiving the cleaning substrates 285, and support retainers 288 consisting of short hollow cylinders. Four support posts 284 extend vertically from the four corners of the base 282 into the support retainer 288 of the frame 283, to provide the frame 283 with sufficient height for the cleaning substrate(s) 285 to engage the bottom surface of the tamp heads 68 of the surface finishing apparatus 60. Each support post 284 has a spring 288 between it and the support retainer 288 to provide flexibility and some "give" when the cleaning substrate 285 passes beneath the surface finishing apparatus 60 or other equipment within the containment zone. Frame 283 is secured to the posts 284 of the base 282 with a fastener, such as a threaded screw.

In the illustrated embodiment, a pair of cleaning substrates 285 include an elongated rectangular body that fits into the pockets 289, and a blade 287 that tapers to an edge along the length. The cleaning substrate is made of a resilient, elastomeric material, which can include natural or synthetic rubber or silicone, and typically has a low durometer that gives the material flexibility. The upper edge of the blade(s) 287 engage the bottom surfaces of the tamp heads 68 of the surface finishing apparatus 60, to wipe or squeegee away any construction or processing material or other debris that may have accumulates on the bottom surfaces of the tamp heads 68 that could interfere with the smoothing or other finishing of the surface of the powder layer.

EXAMPLES

A process system for making a solid dosage form is provided, like that shown in FIG. 1 and described herein. The system includes a process movement apparatus consisting of an omnidirectional magnetic movement apparatus, having a stator formed by twenty-four (24) tile segments, each segment being a square of approximately 1 foot square, which are arranged 2 tiles wide by 12 tiles long, and a thin stainless-steel plate placed over the stator of the process movement apparatus, having a rectangular area of 4 feet wide and 13 feet long. A containment zone formed by a containment housing having a transparent ceiling panel and transparent sidewalls made of Lexan® (polycarbonate) placed onto the stainless-steel plate and laterally centered over the stator. The containment housing has a width of 3 feet, a length of about 10 feet, and a height of about 5 inches in height, and has an air inlet opening at a forward end. A HEPA filter apparatus, illustrated as element 18, is position and sealed into the upper surface of the ceiling panel 33, with the air inlet of the HEPA filter apparatus 18 extending through an open port 34c (FIG. 2) in the ceiling panel 33. The HEPA filter apparatus is positioned and supported above the ceiling panel upon an equipment support 15c elevated by a pair of support brackets 14c.

A plurality of fabrication modules is movable under the control of the omnidirectional magnetic movement system to the process unit operation stations positioned at or over the transport surface enveloped by the containment housing. An example of the fabrication module is shown in FIGS. 4-6 and described herein.

Example 1

A process facility 10, shown in FIG. 1, provided process unit operation stations and processing systems that included a pair of powder dosators 40a, 40b, a pair of liquid printing apparatuses 50, and a pair of surface finishing apparatuses 60. As shown in FIG. 3, a first powder dosage station was positioned over stator tile segment B1, and a second powder dosage station was positioned over stator tile segment A1. The first and second powder apparatuses 40a, 40b were position and sealed into the upper surface of the ceiling panel 33, with its powder discharge extending through an open port 34b in the ceiling panel, for discharging the powder within the depressions of the blister cards.
<Pat Stations>

A first liquid printing apparatus 50a at first printing station was positioned over stator tile segment A3, and a second liquid printing apparatus 50b at second printing station was positioned over stator tile segment A7. The first and second liquid printing apparatuses 50a, 50b were positioned and sealed removably into the upper surface of ceiling panel 33, with their printing nozzles extending through an open port 34a in the ceiling panel.

A first surface finishing apparatus 60a at first finishing station was positioned over stator tile segment(s) A5-A6, and a second surface finishing apparatus 60b at second finishing station was positioned over stator tile segment B7. The first and second surface finishing apparatuses 60a, 60b were positioned and sealed removably into the upper surface of the ceiling panel 33, with its finishing surfaces extending through an open port 34d in the ceiling panel.

A first imaging device 95a at inspection station was positioned over stator tile segment B4. The imaging device 95a is positioned above containment housing 30 for imaging of the blister cards and construction material through the transparent ceiling panel 33. The imaging device 95a is a Cognex 3D camera that can detect the position of the peripheral surface of a powder material within a depression of a blister card for estimating the volume of powder contained within a depression.

A second imaging device 95b is positioned at a second inspection station, positioned over stator tile segment B4. The imaging device 95b is positioned above containment housing 30 for imaging of the blister cards and build powder and binder liquid through the transparent ceiling panel 33. The imaging device 95b is a SWIR camera that detects the position and concentration of a binding liquid applied onto a layer of a build powder in a depression of a blister card for identifying the pattern and concentration of the binder liquid, and specification for water and/or one or more solvents contained therein. The processing controller system receives the images captured by the imaging device 95b and can perform a real-time analysis of the accuracy of the printing operations.

A third imaging device 95c is positioned at a third inspection station, positioned over stator tile segment A8. The imaging device 95c is positioned adjacent to the second liquid printing station at stator tile segment A7, for imaging of the blister cards, build powder and binder liquid through the transparent ceiling panel 33. The imaging device 95c is a SWIR camera that detects the position and concentration of the secondary or finishing binding liquid applied onto a topmost layer of a powder in a depression of a blister card for identifying the pattern and concentration of the binder liquid, and specifically for water and/or one or more solvents contained therein. The processing controller system receives the images captured by the imaging device 95b and can perform a real-time analysis of the accuracy of the printing operations.

A fourth imaging device 95d is positioned at a fourth inspection station, positioned over stator tile segment B10. The imaging device 95d is positioned outside the containment zone, at the entrance for detecting and inspecting the fabrication modules as they are moved into and out of the containment housing 30. The imaging device 95d is a 2D imaging device or camera that can be used to image an identification marker on the fabrication module and the substrate (blister card) for monitoring, identifying, monitoring, and controlling the movement and unit operations performed on the substrate within the containment zone. The 2D imaging device 95d also captures images of the empty substrate (blister card) entering the containment zone, and the processed substrates with finished dosage forms exiting the containment zone, and can communicate the images to the control system where a real-time analysis of the finished dosage for accuracy of the printing operations.
<Blister Card and Fabrication Module>

In a remote forming station or facility, substrate film blanks were thermoformed into the substrate having the first and second six-depression blister cards within the blister frame. The blister forming step also included a printing of a unique identification code, such as a lot number or QR code, onto both the top surface and bottom surface of the blister sheet, and onto the bottom surface (underside) of the base of each depression. The unique 2D bar code of the blister card mounted on the fabrication module (as shown in FIG. 6) was scanned through the window 189 in the hinged mask 90 by the 2D imaging device 95d and entered into data storage of a process unit operations controller prior to the fabrication module entering the containment zone.

The process system included processors to control the processing of six fabrication modules at a time, each according to a build program, with the fabrication modules moving asynchronously through the several and various process unit operations until each build program was completed. The process system can proceed with a single fabrication module, or with up to 10, or up to 15, or up to 30, fabrication modules simultaneously. One each of the six newly formed and identified substrates were positioned onto a corresponding nest of a carrier that was affixed to a uniquely-identifiable shuttle, forming six fabrication modules. An operator placed the first fabrication module 70a (see FIG. 3) onto a loading zone positioned on the transport surface, above one of the tile segments of the omnidirectional magnetic movement apparatus located outside the containment housing (for example, B7) and scanned using the 2D camera 95d at the fourth inspection station the unique identification barcode of the first substrate (blister card) into the process unit operations controller. The movement controller of the omnidirectional magnetic movement apparatus detected that the shuttle of the first fabrication module was positioned in the loading zone, and confirmed to the process unit operations controller that a uniquely identifiable shuttle was correctly positioned in the loading zone, which associated the unique identification code of the first substrate with the uniquely-identifiable shuttle. The process unit operations controller notified the operator that the first fabrication module had been properly identified and informed the operator that the first fabrication module could be moved into the containment system, under the control of the movement controller.
<Asynchronous Movement and Unit Operation Processing>

The movement controller moved the fabrication module (the shuttle with its affixed carrier and substrate) through the air inlet opening and into the containment housing at tile segment(s) A8-B8. The first fabrication module, under the control of both the process unit operations controller and the movement controller, moved first to the 3D imaging device 95a to detect, assess and determine the volume within each of the empty blister depressions.

The first fabrication module then moved to the first liquid printing station at stator tile segment A3. The first fabrication module was properly positioned and oriented at an initial registry position by the movement controller, which initiated a controlled linear movement at programmable (and in some embodiments, constant) linear velocity along a longitudinal axis toward stator tile segment A4, thereby passing the plurality of depressions 83 of the substrate directly beneath of the jetting nozzles of the first liquid printing apparatus 50. The controlled movement of the shuttle of the fabrication module include incremental and/or continuous linear movement in the horizontal plane, including rotation of the fabrication module around the vertical axis, to maneuver the fabrication module from one process unit operation to the next process unit operation, while maneuvering simultaneously and independently the other five fabrication modules (70b-70f, FIG. 3) through the various process unit operations, from station to station, and through the same transport surface and containment space, without contact or collision, or undue delays or "traffic jams", with the other fabrication modules. Under the control of the process unit operations controller, and in accordance with the dosage printing program, a proper pattern of printing liquid was deposited as a preliminary binding liquid layer onto the inside bottom surface of each depression of the blister substrate.

The first fabrication module then moved to the first powder dosage station that was positioned over stator tile segment B1, and was properly positioned and oriented at an initial registry position by the movement controller. Under the control of the process unit operations controller, and in accordance with the dosage printing program, a predetermined volume of powder material was dispensed by a dosator 40, shown in FIGS. 8A and 8B, and deposited into each depression of the blister substrate, over top of the preliminary binding liquid layer, as a first deposit of powder.

After depositing of the volume of powder material, the first fabrication module 70a then moved to the vibration leveling device 55 at adjacent position at tile segment A2. The vibration leveling device 55, as described herein, had voice-coil actuators (VCA) disposed vertically above the transport surface 16. When the first fabrication module was positioned beneath the voice-coil actuators, vertically-extending probes 56 from the actuators extended down and contacted the mask 90 of the carrier 72 (see FIG. 4), and transmitted vibration at a frequency of about 40 Hz and a 1-volt amplitude to the nest 74, directly to and through the mask 90 and to the blister card 82 disposed thereunder. The vibrating of the blister cards 82 formed the first powder deposited in the depression into a layer of powder having a uniform thickness and an even, level upper surface within the depression. Alternatively, the fabrication module and its blister card can be vibrated during the powder deposition at the first powder dosage station, utilizing the vibration forces employed in the dosator 40 for effecting free-flow of powder material into and through the dosator, to deliver a dose amount of powder material within the depression that has a level surface.

Optionally, or in addition to leveling provided in the vibration leveling device 52 at the leveling station, the movement controller of the omnidirectional magnetic movement apparatus can actuate the movement stator to cause the first fabrication module, through the magnetic forces on the shuttle, to vibrate (for example, at a frequency of about 40 Hz at about a 1-volt amplitude), each vibration cycle consisting of a small-angle rotation (pitch) through the longitudinal axis of the shuttle, which can cause the carrier and the substrate to vibrate until the substantially uniform layer of the first powder deposited into the cavity has been formed within the depressions of the blister card.

The first fabrication module then moved, under the control of both the process unit operations controller and the movement controller, back to the 3D imaging device 95a to detect, assess and determine the volume remaining within each of the empty blister depressions above the first leveled uniform layer of powder material.

The first fabrication module, under the control of both the process unit operations controller and the movement controller, was then moved to the first liquid printing station that was positioned over stator tile segment A3, and was properly positioned and oriented at an initial registry position by the movement controller. The movement controller then initiated a controlled linear movement at constant linear velocity, preferably of 0.25 meters/second (m/s) or less, along a longitudinal axis toward stator tile segment A4, thereby passing the plurality of depressions of the substrate, which contained a first uniform layer of powder, directly beneath of the jetting nozzles of the first liquid printing apparatus.

Under the control of the process unit operations controller, and in accordance with the dosage printing program, a proper pattern and quantity of printing liquid was deposited onto the first uniform layer of powder, thereby wetting the same and forming a first wetted powder layer within each depression of the blister substrate.

The first fabrication module was moved to the first inspection station that was positioned over stator tile segment B4, and one or more images of the upper surface of the fabrication module were taken by the SWIR imaging device 95b to detect and assess the volume and distribution of the layer of wetted powder material within the blister depressions, and to detect the location or accuracy of the printed liquid droplets deposited onto the first layer of powder in forming the wetted powder layer.

The first fabrication module then moved, under the control of both the process unit operations controller and the movement controller, back to the 3D imaging device 95a to detect, assess and determine the volume remaining within each of the empty blister depressions above the first layer of wetted powder material.

The first fabrication module then moved (under the control of both the process unit operations controller and the movement controller) back to the first powder dosage station (or to the second powder dosage station) that was positioned over stator tile segment A1 if another fabrication module is already positioned at the first powder dosage station), and repeated the depositing of a second predetermined volume of powder material over top of the first wetted powder layer in each depression, as a second deposit of powder, and the second deposit of powder was leveled into a second uniform layer of powder had been done for the first deposit of powder. The first fabrication module then moved back to the 3D imaging device 95a to detect, assess and determine the volume remaining within each of the empty blister depressions above the second leveled uniform layer of powder material.

The first fabrication module was then moved to the first liquid printing station (or to the second liquid printing station that was positioned over stator tile segment A7 if another fabrication module was already positioned at the first liquid printing station, though this would be rare since the processing through the first liquid printing station proceeds rapidly). The first fabrication module moved at the constant linear velocity, preferably of 0.25 m/s or less, along a longitudinal axis to pass the plurality of depressions of the substrate, which contain the second uniform layer of powder, directly beneath of the jetting nozzles of the first liquid printing apparatus, and in accordance with the dosage printing program, a proper pattern and quantity of printing liquid for the second build layer was deposited onto the second uniform layer of powder, thereby wetting the same and forming second wetted powder layer within each depression of the blister substrate.

The first fabrication module was moved again to the inspection station and one or more images of the upper surface of the fabrication module were taken by the SWIR imaging device 95b to detect and assess the location or accuracy of the printed liquid droplets deposited onto the second layer of powder in forming the wetted powder layer.

The first fabrication module repeated the cycle of moving over the transport surface and through the process equipment to build and assess four additional wetted powder layers, by cycling through the first powder dosage station (or the second powder dosage station), leveling, detection and determine of the volume remaining within each of the empty blister depressions above the leveled layer of powder material at the 3D imaging device, printing liquid onto the second uniform layer of powder, and inspection of the wetted powder layers for location and accuracy of the printing liquid.

After the final layer of powder material was deposited, leveled, and inspected by the 3D imaging device to determine of the volume remaining within each of the empty blister depressions above the final, leveled layer of powder material, the first fabrication module moved, under the control of both the process unit operations controller and the movement controller, to a first surface finishing station that was positioned over stator tile segment(s) A5-A6, and was properly positioned and oriented at an initial registry position by the movement controller. The tamp heads of a surface finishing apparatus, for example as shown in FIGS. 11A and 11B and described herein, are lowered down onto the dry, leveled and uppermost layer of powder to both smoothen and shape the upper surface with a slightly-domed rounded contour.

The first fabrication module then moved to a finish printing station at stator tile segment A7, and was properly positioned and oriented at an initial registry position by the movement controller. The movement controller then initiated a controlled linear movement at constant linear velocity, preferably of 0.25 meters/second (m/s) or less, along a longitudinal axis toward stator tile segment A8, thereby passing the plurality of depressions of the substrate, which contained the fully-formed, wetted dosage form, directly beneath of the jetting nozzles of the second liquid printing apparatus. Under the control of the process unit operations controller, and in accordance with the dosage printing program, a first portion of a quantity and pattern of a finishing liquid was deposited onto the top surface of the fully-formed dosage form, to form a first layer of finish coating (which be a different or the same composition as the binder liquid applied by the first liquid printing apparatus). The first fabrication module was moved to a third inspection station and one or more images of the upper surface of the fabrication module were taken by the SWIR imaging device 95b to detect and assess the location or accuracy of the printed liquid droplets of the finish coating deposited onto the final, shaped layer of powder material.

The first fabrication module was then returned to the same finish printing station, three more times under the control of the process unit operations controller, and in accordance with the dosage printing program, three additional portions of the quantity and pattern of the finishing liquid were deposited onto the top surface of the fully-formed dosage form, to form the remaining layers of finish coating (which be a different or the same composition as the binder liquid applied by the first liquid printing apparatus). The first fabrication module then moved again to the third inspection station and the SWIR imaging device 95c to detect and assess the location or accuracy of the printed liquid droplets of the last finish coating deposited.

The first fabrication module, with the final printed and finished dosage forms within the depressions, then moved to a second surface finishing station, similar again to the apparatus shown in FIGS. 11A and 11B, at stator tile segment B7, and was properly positioned and oriented at an initial registry position by the movement controller. Under the control of the process unit operations controller, and in accordance with the dosage printing program, the two sets of surface finishing bodies (UHMWPE) of the surface finishing apparatuses were lowered while slowly rotating into contact with the upper surface of the uppermost wetted powder layer, within a depression, to lessen the surface roughness of upper finished surface of the dosage form. When finished, the rotating finishing bodies are slowly raised from the finished surfaces.

The first fabrication module having the blister substrate with the twelve finished, fully-formed, wetted-powder dosage forms, under the control of both the process unit operations controller and the movement controller, was moved out through the transport opening 36 in the containment housing 30 and outside the containment zone to the fourth inspection station, at tile segment B10, where the fourth 2D imaging device 95d acquires one or more images of the upper finished surface of the built dosage forms to detect and assess the appearance and texture of the upper surfaces of the built dosage forms. The barcode of the blister card is also scanned by the 2D imaging device 95d into the process unit operations controller. The movement controller of the omnidirectional magnetic movement apparatus also has detected the same uniquely-identifiable shuttle, and the process unit operations controller confirms that the shuttle remains associated the same unique identification code of the first substrate. The process unit operations controller then notified the operator that the dosage form building of the first fabrication modules were properly identified and that the first fabrication module was ready to be moved manually to a dosage form drying system, to evaporate the excess water and solvent within the wetted dosage form.

The other five fabrication modules, each with respective uniquely printed identification markings on the substrate and associated with respective uniquely-identifiable shuttles, were run through the same process unit operations as for the first fabrication module, each fabrication module being processed asynchronously through the same process unit operation stations with the other fabrication modules of the six-module batch.

A drying operation was initiated after all six of the fabrication modules in the batch had been processed out of the containment housing at the unloading station. Optionally, a drying operation could be affected to each loaded substrate of the fabrication module independently as the fabrication module had been processed out of the containment housing. The respective substrates (blister trays) fully loaded with the wetted dosage forms were removed (lifted) from the carrier and passed through the drying system. After drying, the loaded blister tray was separated from the nest of the carrier, and further processed including film sealing of the blister tray and packaging.

The modular design of the processing system of this example can be used for development, simulation, testing, experimentation, and similar activities on a small scale, and the dosage-forming equipment or modules of equipment used are deployable in pilot and commercial-scale manufacturing. This modularity allows thorough and systematic testing and development of the process and operating conditions of these equipment and equipment module, before installing the same equipment and modules of equipment into a GMP-rated pilot or manufacturing facilities. The modularity of the equipment and modules of equipment can also be withdrawn from a GMP-rated pilot or manufacturing facility, and placed into the processing facility for dynamic simulation of the process on the smaller scale to aid in processing adjustments and trouble-shooting of process anomalies, before returning the same equipment or module of equipment to the pilot or manufacturing facility.

Example 2: Mask Removal Vestibule

In a second example, the system and operation of Example 1 was used to form the first fabrication module having the blister substrate with the twelve finished, fully-formed, wetted-powder dosage forms. In this example, a mask-raising device 190, as shown in FIGS. 1 and 17A and 17B, was positioned at the transport opening 36 of the containment housing. The mask-raising device 190 provided a vestibule in which the mask 90 of a fabrication module can be raised up off of the substrate 80 and the nest 74 of the fabrication module 70, and removed manually or mechanically. As the forward end of the mask 90 entered the vestibule opening between the pair of side walls 191, the pair of pins 94 of the mask 90 entered at the elevation of the narrow grooves 192 on inner surface of the vestibule, and as the fabrication module proceed forward through the vestibule, the pins 94 of the mask 90 passed upward along the curve in the groove to pivot the mask 90 up off of and away from the blister card. As the pins 94a ride up the horizontal portion 195, the leading end of mask 90 is raised up and off the nest 74 and exposing the blister card to the 2D imaging device 95d for reading of its barcode and inspection and assessment of the appearance and texture of the upper surfaces of the built dosage forms.

Example 3: Active-Loading Tablet System

An active-loading tablet system is constructed using an omnidirectional magnetic movement apparatus for movement of transport modules to and between a group of process unit operation stations for forming tablet having a dosage of an active agent.

Figure 18:
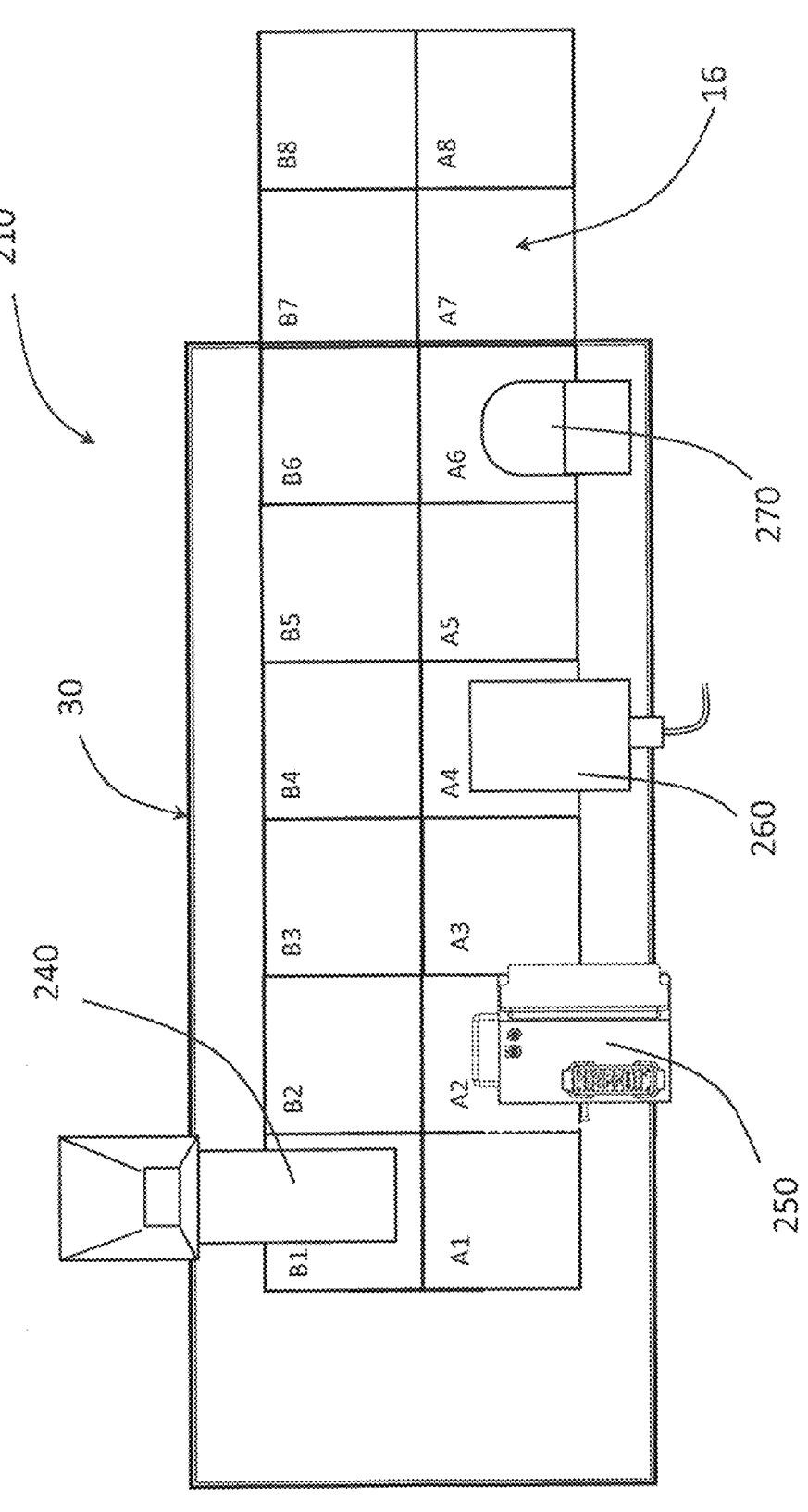
FIG. 18 illustrates in plan view a process system that includes a transport surface, a containment system, and several process unit operation systems positioned within the containment system and above the transport surface for forming a tablet form.

The active-loading tablet system 210 is shown in a plan layout in FIG. 18 to include a stator transport surface, a containment system, and the group of process unit operation stations that includes a base tablet supply system 240, an active agent dispensing system 250, a drying system 260, and an optional coating system 270, each system stationed above some portion of stator transport surface 16 of the omnidirectional magnetic movement apparatus, and/or within the containment housing 30. The base tablet to be used in the active-loading tablet system 210 can be preformed by other manufacturing means, such as a compressed tablet making system, and supplied to base tablet loading system 240 of the active-loading tablet system 210.

In this example, the base tablet is a pre-formed compressed tablet. The tablet includes a first-side face and an opposite second-side face, and a peripheral edge. At least one of the side faces, though in this example both of the side faces, have a concave depression in the side face that extends partly-inwardly from slightly inboard of the peripheral edge toward the center planar of the tablet. The active agent is in the form of a liquid active agent consisting of a liquid composition comprising the active agent with one or more solvents or diluents.

A base tablet arranging and dispensing system 240 is positioned over a tablet arrangement station located at stator tile segment B1. The base tablet arranging and dispensing system 240 includes a loading container or hopper containing base tablets in communication by gravity feeding into a loading chute that delivers base tablets into a holding system. The base tablet dispensing system has an upper inlet end disposed outside (and above) the containment housing 30, and a tablet dispensing end that extends through a sealable port (not shown) in the ceiling panel of the containment system. The base tablet dispensing system includes an arrangement device to position a pre-determined plurality of the base tablets within a horizontal plane, and into predetermined arrangement or array, for example, a 3×4 or 4×6 array, with fractional portions (for example halves or quarters) or all of the tablets equidistantly spaced in a rectangular pattern. In this example, the array includes two sets of six base tablets, arranged and dimensioned as shown in FIG. 6. The base tablet dispensing system also includes a tablet placing means for lowering vertically and placing the arranged base tablets onto an upper surface of a substrate, preferably the substrate having an array of concave depressions of the same dimensions and arrangement as the arrangement device, so that each base tablet in the arrangement device is placed into a corresponding (array position) depression of the substrate. In this example, the substrate is a blister substrate, as described herein, disposed and oriented by a carrier element of a transport module, such as shown in FIGS. 4 and 6, to provide a fabrication module that employs the shuttle for controllably moving the transport module over the stator of the omnidirectional magnetic movement apparatus. The fabrication module, under the control of both the process unit operations controller and the movement controller, moves first to the tablet arrangement station beneath the dispensing means of the base tablet arranging and dispensing system 240, where one of a predetermined plurality of the base tablets is deposited into each respective depression of the blister substrate.

An active agent dispensing system 250 provides for the addition of a liquid dose of an active agent to each of the deposited base tablets on the blister substrate, and includes real-time monitoring, feedback and adjustment of the dispensing of the liquid active agent onto each base tablet. The active agent dispensing system has an upper end disposed outside the containment system for receiving one or more supply units of the liquid active agent, and a liquid dispensing end that extends through a sealable port (not shown) in the ceiling panel of the containment housing 30.

The liquid dispensing end includes one or more dispensing modules for dispensing a pre-determined or desired mass or volume quantity of an active agent onto at least the first-side face of the base tablet. Each dispensing module can be connected to a respective active agent supply unit installed at the upper end of the dispensing system 250. A supply unit can be a replaceable cartridge, container or canister that is easily inserted in, or connected to, the upper end of the dispensing system. The use of more than one dispensing module provides for increased speed and efficiency in dispensing of the liquid dose of active agent, and/or adding different active agents to a base tablet without need for cleaning or replacing the module, such as, for example, in layering or on opposing outer surfaces through reprocessing the carrier tablet back through the active agent dispensing system. Each dispensing module includes a pump with an inlet connected in liquid communication with a supply unit and with an outlet connected in liquid communication with one or more dispensing nozzles. In this embodiment, the pump outlet is in liquid communication with a plurality of dispensing nozzles disposed in an array that is the same as the predetermined array as the substrate. The pump is preferably a metering, positive displacement pump, for example, a peristaltic pump, a rotary gear pump, or other pump type that can provide the same degree of accuracy and speed) that can dispense variably a predetermined mass or volumetric quantity, including as little as a single droplet, of the liquid active agent through the dispensing nozzle, under control of the control system. An example of the active agent dispensing system 250 is described in U.S. Pat. No. 8,252,234, the disclosure of which is incorporated by reference in its entirety.

A fabrication module with the base tablets deposited within each depression of the blister substrate, is move under the control of both the process unit operations controller and the movement controller to a dispensing station beneath the active agent dispensing system, and is positioned and oriented relative to the one or more dispensing nozzles. An example of the fabrication module is illustrated in FIGS. 4-6 and described herein. When using a single dispensing nozzle, the fabrication module is controlled to position a depression, and the base tablet contained therein, directly beneath the single dispensing nozzle, by movement of the module under the control of the movement controller. The pump is then activated to dispense the predetermined quantity of liquid active agent into the first-side face of the position base tablet. The fabrication module is then similarly moved under control to position a next depression for the dispensing of the liquid active agent, and the pump is again activated to dispense the predetermined quantity of liquid active agent into the first-side face of the position base tablet. The positioning of the fabrication module and the dispensing of liquid active agent continues until liquid active agent has been applied to each base tablet, thereby forming active-loaded tablets.

When using an array of dispensing nozzles, the fabrication module is positioned to arrange the plurality of depressions in registry with the array of dispensing nozzles, to simultaneously dispense liquid active agent through the dispensing nozzles and onto the corresponding array of base tablets.

In some embodiments of a base tablet, the loaded liquid active agent can partially or completely soak or migrate into the solid matrix of the base tablet, while in other embodiments, the liquid active agent can form a pool of liquid within a concave, first-side face of the loaded tablet.

When the liquid active agent is a liquid composition with one or more solvents, a drying system 260 is used to evaporate excess solvent from the loaded tablets. The drying system 260 is positioned over a drying station located at stator tile segment A4. The drying system has a drying apparatus or drying monitors. The drying apparatus provides heat and optionally air flow to the active-loaded tablets to evaporate excess solvent and leave a solidified or immobile film of the active agent on the first-side face of the loaded tablet and/or partially migrated into the tablet. The drying system 260 is integrated into the containment housing, it can optionally be disposed outside the containment housing 30 but accessible with the omnidirectional magnetic movement apparatus, by conveying fabrication modules with the loaded tablets out of the containment zone to a remote drying system under the control of both the process unit operations controller and the movement controller. The drying apparatus can have any one or a combination of infrared (IR), a convection, conduction, and/or microwave heating. The drying system 260 can include sensors to detect conditions, for example, the surface temperature of the tablets, moisture content on the surface of the tablets.

After drying of loaded tablets is completed, additional quantities of the same or a different liquid active agent can be applied to the same tablets. The fabrication modules with the dried tablets can be moved under the control of the process unit operations controller and the movement controller back to the active agent dispensing station 250 for applying another quantity of liquid active agent, and to the drying system 260 for evaporation of solvent, as needed.

After the quantity or quantities of liquid active agent have been loaded onto the tablet and optionally dried, a coating system 270 positioned over a coating station located at stator tile segment A6. The coating system 270 applies a coating over the loaded quantity of active agent in the tablet to prevent abrasion and the resulting loss of any active agent during normal handling of the tablet. The coating can be a sealant, and can provide a uniform appearance for the pharmaceutical product by hiding or disguising the applied liquid dose. The coating system 270 preferably has a pad-printing device positioned within a coating source and a coating dryer. The pad printing device transfers the coating to the upper surface of the loaded tablet, and is advantageous because of its efficient transfer of a coating to the loaded tablet without waste, e.g., no overspray. Coating system can be incorporated into the containment system, by extending the pad printing device through a sealable port in the upper surface of the containment system, to provide a coating station where a fabrication module with the base loaded tablets within each depression of the blister substrate, is moved under the control of the process unit operations controller and the movement controller to a coating station beneath the coating system, and is positioned and oriented relative to the pad-printing device. The fabrication module is controlled to position in turn each depression, and the loaded tablet contained therein, directly beneath and in registry with the pad-printing device, for applying a coating of the coating material onto the first-side face of a loaded tablet, and then re-positioned to a next depression, until coating material has been applied to each loaded tablet, to form coated tablets.

Because the instant application is a continuation application, to the extent any amendments, characterizations, or other assertions previously made (in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

The invention claimed is:

1. A process system for making an article or for processing of materials or components of an article, comprising:
   i) an omnidirectional magnetic movement apparatus comprising a planar transport surface, and a stator disposed on an underside of the transport surface and comprising a plurality of actuation coils that exert a primary magnetic field through the transport surface in response to a controlled current through an actuation circuit;
   ii) one or more fabrication modules, each fabrication module comprising
      a) at least one shuttle comprising a planar body and one or more magnetic components that respond to the primary magnetic field exerted by the plurality of actuation coils to levitate and transport the at least one shuttle omnidirectionally above and over the transport surface, including in a horizontal plane in an x-y direction to a specified x-y position and orientation,
      b) a carrier comprising a lower portion fastened or secured to a surface of the at least one shuttle, and an upper portion, and
      c) at least one substrate attached or secured to the upper portion of the carrier for fixing the at least one substrate onto the at least one shuttle, the at least one substrate comprising one or more formation surface;
   iii) a containment system including a containment housing to provide a containment zone above the transport surface of the omnidirectional magnetic movement apparatus, the containment housing comprising a ceiling having one or more sealable openings to provide access to the one or more fabrication modules within the containment zone; and
   iv) an article forming unit system comprising one or more unit operation equipment positioned within the one or more sealable openings in the ceiling of the containment housing above the transport surface, the one or more unit operation equipment comprising:
      a) a depositing device positioned within one of the one or more sealable openings of the containment housing above the transport surface, the depositing device configured for placing a construction material consisting of particulate or powder material onto the one or more formation surface of the at least one substrate when the one or more fabrication module is positioned at a deposition position of the transport surface beneath the depositing device; and
      b) a phase modification device positioned within one of the one or more sealable openings of the containment housing above the transport surface, the phase modification device configured for forming at least a portion of the placed particulate or powder material into an intermediate or finished article on or within the one or more formation surface of the at least one substrate when the one or more fabrication modules is positioned at a phase modification position of the transport surface beneath the phase modification device; and
   v) a movement controller for sending a controlled current through one or more of the plurality of actuation coils to control the levitation and transportation of the at least one shuttle of the one or more fabrication modules, for positioning and orienting the at least one substrate and the one or more formation surface thereof beneath or relative to one or more unit operation equipment.

2. The process system according to claim 1 wherein the movement controller is configured to include one or more steps of transporting the one or more fabrication modules asynchronously between at least the deposition position and the phase modification position, for forming the intermediate or finished article.

3. The process system according to claim 1 wherein the transport surface is a rectangular area including a central area and a peripheral area, and the peripheral area has a width dimension that is at least a width of the one or more fabrication modules, and the central area has a width dimension that is at least a width of the one or more fabrication modules.

4. The process system according to claim 1 wherein the at least one substrate consists of a blister card, and the one or more formation surface comprises a plurality of depressions arranged in an array on the blister card.

5. The process system according to claim 4 wherein the system further includes a means for leveling of the placed particulate or powder material within the plurality of depressions to a uniform thickness.

6. The process system according to claim 4 wherein the one or more unit operation equipment further includes a construction material leveling device or a surface finishing apparatus, and the process system further includes one or more additional processing devices selected from the group consisting of a drying device, a substrate loading device, a substrate unloading device, and a combination thereof.

7. The process system according to claim 6 wherein the one or more unit operation equipment further includes a surface finishing apparatus for surface finishing an upper surface of the placed construction material or the intermediate or finished article on or within one or more of the plurality of depressions of the blister card when the at least one shuttle is positioned at a surface finishing position on the transport surface.

8. The process system according to claim 4 wherein the process system further includes a deposition sensing device for detecting a uniformity of distribution of the placed particulate or powder material within one or more of the plurality of depressions of the blister card.

9. The process system according to claim 4 wherein the depositing device comprises a powder dosator configured for depositing simultaneously and separately the particulate or powder material into the plurality of depressions arranged in the array on the blister card, wherein the particulate or powder material comprises an ingestible powder material that comprises an active agent selected from the group consisting of an API, a biologically-active material, a medicament, and a combination thereof; and the phase modification device comprises a means for dispersing a binding liquid that forms the ingestible powder material into a bound-powder material comprising an interconnected matrix of the ingestible powder material that is porous and rapidly orodispersive, and the article consists of a solid dosage form.

10. The process system according to claim 9, wherein the binding liquid comprises a solvent, and the means for dispensing the binding liquid comprises a liquid printer for printing of the binding liquid onto an upper surface of the particulate or powder material to form a wetted powder layer within the plurality of depressions of the blister card of the one or more fabrication modules.

11. The process system according to claim 1, wherein the process system further comprises one or more cleaning modules comprising a) at least one second shuttle comprising a planar body and one or more magnetic components that respond to the primary magnetic field exerted by the plurality of actuation coils to levitate and transport the at least one shuttle omnidirectionally above and over the transport surface, and b) at least one cleaning substrate configured for cleaning of a contaminated device or contaminated equipment of the article forming system.

12. The process system according to claim 1, wherein the containment housing comprises a sidewall, the sidewall having one or more transport openings to provide entry, egress, or both entry and egress for the one or more fabrication modules into and out of the containment zone.

13. The process system according to claim 12, wherein a vertical height of the ceiling of the containment housing is sufficient to allow movement of the one or more fabrication modules over the transport surface and beneath the one or more unit operation equipment that penetrate the ceiling of the containment housing.

14. The process system according to claim 13, wherein the containment housing further comprises one or more airflow openings to allow outside air selected from the group consisting of ambient air, conditioned gases or conditioned air, to pass into the containment zone and through the containment zone as process air.

15. The process system according to claim 14, further comprising an air handling and filtration system that includes an air processing apparatus configured to draw outside air into the containment zone and the process air through the containment zone.

16. The process system according to claim 12, wherein the containment housing further comprises one or more airflow openings to allow outside air selected from the group consisting of ambient air, conditioned gases or conditioned air, to pass into and through the containment zone as process air, and an open port to allow the process air to pass out of the containment zone.

17. The process system according to claim 16, further comprising a particulate filtration apparatus configured to draw the outside air through the one or more airflow openings and into the containment zone, and to draw the process air through the containment zone and out through the open port of the containment housing and into the particulate filtration apparatus.

18. The process system according to claim 13, wherein a ratio of an average vertical height of the containment housing to an area of the containment housing is 0.1 cm/m$^2$ to 100 cm/m$^2$.

19. The process system according to claim 18, wherein the ratio of the average vertical height of the containment housing to width of the containment housing is 0.5 cm/m to 20 cm/m.

20. The process system according to claim 1 wherein the at least one shuttle further levitates and transports above and over the transport surface in a vertical direction in a z axis.

21. The process system according to claim 5 wherein the means for leveling of the placed particulate or powder material comprises a means for vibrating the blister card, the vibrating means comprising a vibration leveling apparatus configured to vibrate the blister card with an amplitude and frequency to transform the particulate or powder material placed into the plurality of depressions of the blister card into a layer of the particulate or powder material with a level upper surface.

22. The process system according to claim 21 wherein the vibration leveling apparatus includes one or more voice coil actuators to generate vibrations that are passed onto the blister card to effect movement of the particulate or powder material disposed with the depressions.

23. The process system according to claim 22 wherein the vibration leveling apparatus includes a rigid probe that transmits the vibrations from the voice coil actuator into the blister card.

24. The process system according to claim 10 wherein the process system further comprises a print nozzle cleaning device comprising a nozzle cleaning shuttle, a nozzle cleaning carrier secured to the nozzle cleaning shuttle and having a frame for securing a nozzle cleaning blade made of a resilient, elastomeric material and comprising an upper edge to wipe and clean a printing nozzle of the liquid printer.

25. The process system according to claim 1 wherein the movement controller is configured to position and orient the one or more fabrication modules at one or more of the deposition position beneath the depositing device and the phase modification position beneath the phase modification device, while levitated above the transport surface.

26. The process system according to claim 9 wherein the depositing device comprises multiple powder dosators, each powder dosator configured for depositing a different predetermined dose amount of the particulate or powder material into the plurality of depressions on the blister card.

27. The process system according to claim 5 wherein the movement controller is configured to oscillate, vibrate, or oscillate and vibrate the shuttle of the one or more fabrication modules at a frequency and magnitude to form the placed particulate or powder material into a layer of particulate or powder material having the uniform thickness and substantially even, level upper surface within the plurality of depressions.

* * * * *